(12) United States Patent
Thomas et al.

(10) Patent No.: US 9,310,281 B2
(45) Date of Patent: Apr. 12, 2016

(54) AUTOMATED PELLETIZED SAMPLE BLOTTING APPARATUS AND METHODS

(71) Applicant: QIAGEN GAITHERSBURG, INC., Gaithersburg, MD (US)

(72) Inventors: Bradley Scott Thomas, Timonium, MD (US); Brian Austin Self, Monkton, MD (US); Eric Schneider, Catonsville, MD (US); Franklin Regan, Baltimore, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 316 days.

(21) Appl. No.: 13/657,623

(22) Filed: Oct. 22, 2012

(65) Prior Publication Data
US 2014/0112842 A1    Apr. 24, 2014

(51) Int. Cl.
*G01N 1/28* (2006.01)
*G01N 35/02* (2006.01)

(52) U.S. Cl.
CPC ............... *G01N 1/28* (2013.01); *G01N 1/2813* (2013.01); *G01N 35/026* (2013.01); *G01N 2001/282* (2013.01)

(58) Field of Classification Search
None
See application file for complete search history.

(56) References Cited

U.S. PATENT DOCUMENTS

| | | | |
|---|---|---|---|
| 3,050,239 A | 8/1962 | Williams, Jr. | |
| 3,625,485 A | 12/1971 | Adler | |
| 4,164,449 A | 8/1979 | Dorn et al. | |
| 4,168,233 A | 9/1979 | Anderson | |
| 4,438,068 A | 3/1984 | Forrest | |
| 4,472,357 A | 9/1984 | Levy et al. | |
| 4,484,907 A | 11/1984 | Sheeran, Jr. | |
| 5,149,408 A | 9/1992 | Perlman | |
| D356,232 S | 3/1995 | Armstrong et al. | |
| 5,525,298 A | 6/1996 | Anami | |
| 5,846,493 A | 12/1998 | Bankier et al. | |
| 6,045,494 A | 4/2000 | Toyama | |
| D445,907 S | 7/2001 | Monks | |
| 6,796,195 B2 | 9/2004 | Povey et al. | |
| 6,846,455 B1 | 1/2005 | Carney et al. | |

(Continued)

FOREIGN PATENT DOCUMENTS

| | | |
|---|---|---|
| DE | 19730445 | 1/1999 |
| EP | 0 312 252 | 4/1989 |

OTHER PUBLICATIONS

Entire patent prosecution history of U.S. Appl. No. 13/657,633, filed Oct. 22, 2012, entitled, "Automated Pelletized Sample Decanting and Methods."

(Continued)

*Primary Examiner* — Jill Warden
*Assistant Examiner* — Julie Tavares
(74) *Attorney, Agent, or Firm* — RatnerPrestia

(57) ABSTRACT

An automated sample tube blotting system having one or more rotating grippers, a supply of absorbent material, a transporter, and an absorbent material removal mechanism. Each rotating gripper has a respective holder configured to selectively mate with a respective interface on a tube strip, and the one or more rotating grippers are rotatable between a first position in which the tube strip is upright and a second position in which the tube strip is inverted. The transporter is configured to move the rotating gripper in a lateral direction from a starting location to a location above the absorbent material, and in a vertical direction towards and away from the absorbent material.

8 Claims, 36 Drawing Sheets

(56) References Cited

U.S. PATENT DOCUMENTS

| | | |
|---|---|---|
| 7,297,485 B2 | 11/2007 | Bornarth et al. |
| 7,523,649 B2 | 4/2009 | Corey et al. |
| 7,543,480 B2 | 6/2009 | Africk et al. |
| 7,575,865 B2 | 8/2009 | Leamon et al. |
| D608,013 S | 1/2010 | Coulling et al. |
| 7,674,434 B2 | 3/2010 | Sakal et al. |
| 7,739,911 B2 | 6/2010 | Panetta |
| D621,521 S | 8/2010 | Nuotio |
| 7,838,296 B2 | 11/2010 | Corey et al. |
| 7,930,066 B2 | 4/2011 | Eliuk et al. |
| 8,021,629 B2 * | 9/2011 | Sando et al. ............... 422/505 |
| 8,231,830 B2 | 7/2012 | Wakamiya et al. |
| 8,272,255 B2 | 9/2012 | Halverson et al. |
| 8,273,706 B2 | 9/2012 | Pappin et al. |
| 8,282,895 B2 | 10/2012 | Miller et al. |
| 8,288,520 B2 | 10/2012 | Eder et al. |
| 2002/0108857 A1 | 8/2002 | Paschetto et al. |
| 2005/0037485 A1 | 2/2005 | Rodgers et al. |
| 2005/0074360 A1 | 4/2005 | DeWalch |
| 2005/0112783 A1 * | 5/2005 | Evans et al. ............... 436/518 |
| 2006/0078463 A1 | 4/2006 | Shea et al. |
| 2008/0031774 A1 | 2/2008 | Magnant et al. |
| 2008/0247914 A1 | 10/2008 | Edens et al. |
| 2009/0205979 A1 | 8/2009 | Bekki et al. |
| 2009/0221059 A1 | 9/2009 | Williams et al. |
| 2010/0066109 A1 | 3/2010 | Pedrazzini |
| 2010/0129789 A1 | 5/2010 | Self et al. |
| 2011/0206643 A1 | 8/2011 | Fulga et al. |
| 2012/0163117 A1 | 6/2012 | Guidry, Jr. et al. |

OTHER PUBLICATIONS

Non-Final Office Action mailed May 27, 2015 for U.S. Appl. No. 13/673,633.
International Search Report for PCT International Application No. PCT/US13/65864 dated Feb. 24, 2014.
International Search Report for PCT International Application No. PCT/US2013/065853 dated Mar. 5, 2014.
Entire patent prosecution history of U.S. Appl. No. 13/657,633, filed Oct. 22, 2012, entitled, "Automated Pelletized Sample Decanting Apparatus and Methods."
Entire patent prosecution history of U.S. Appl. No. 13/657,637, filed Oct. 22, 2012, entitled, "Sample Processing Apparatus and Methods."
International Search Report for PCT International Application No. PCT/US13/065864 dated May 7, 2015.
International Search Report for PCT International Application No. PCT/US13/065853 dated May 7, 2015.
International Search Report for PCT International Application No. PCT/US13/065865 dated May 7, 2015.
Notice of Allowance mailed Oct. 6, 2015 for U.S. Appl. No. 13/657,637.
Office Action mailed Dec. 4, 2015 for U.S. Appl. No. 13/657,633.
"Hybrid Capture 2 High-Risk HPV DNA Test", Digene Corporation, 2004, pp. 1-22.
International Search Report for International Application PCT/US2013/65865 mailed Jan. 14, 2014.
Notice of Allowance for U.S. Appl. No. 13/657,633 dated Feb. 17, 2016.

\* cited by examiner

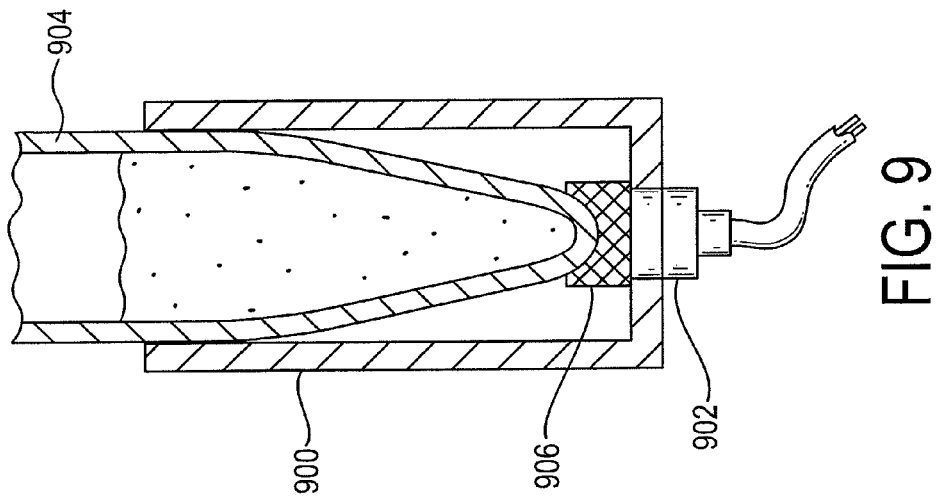
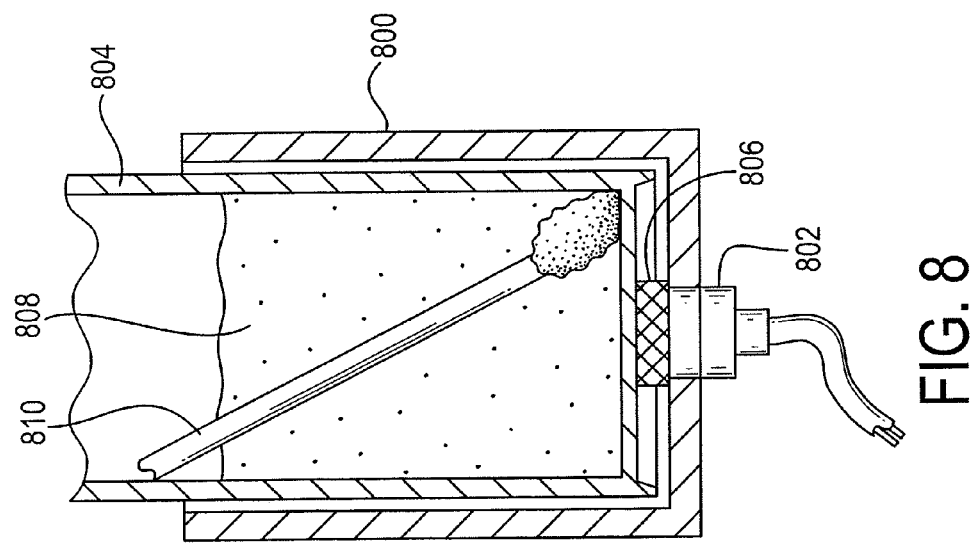

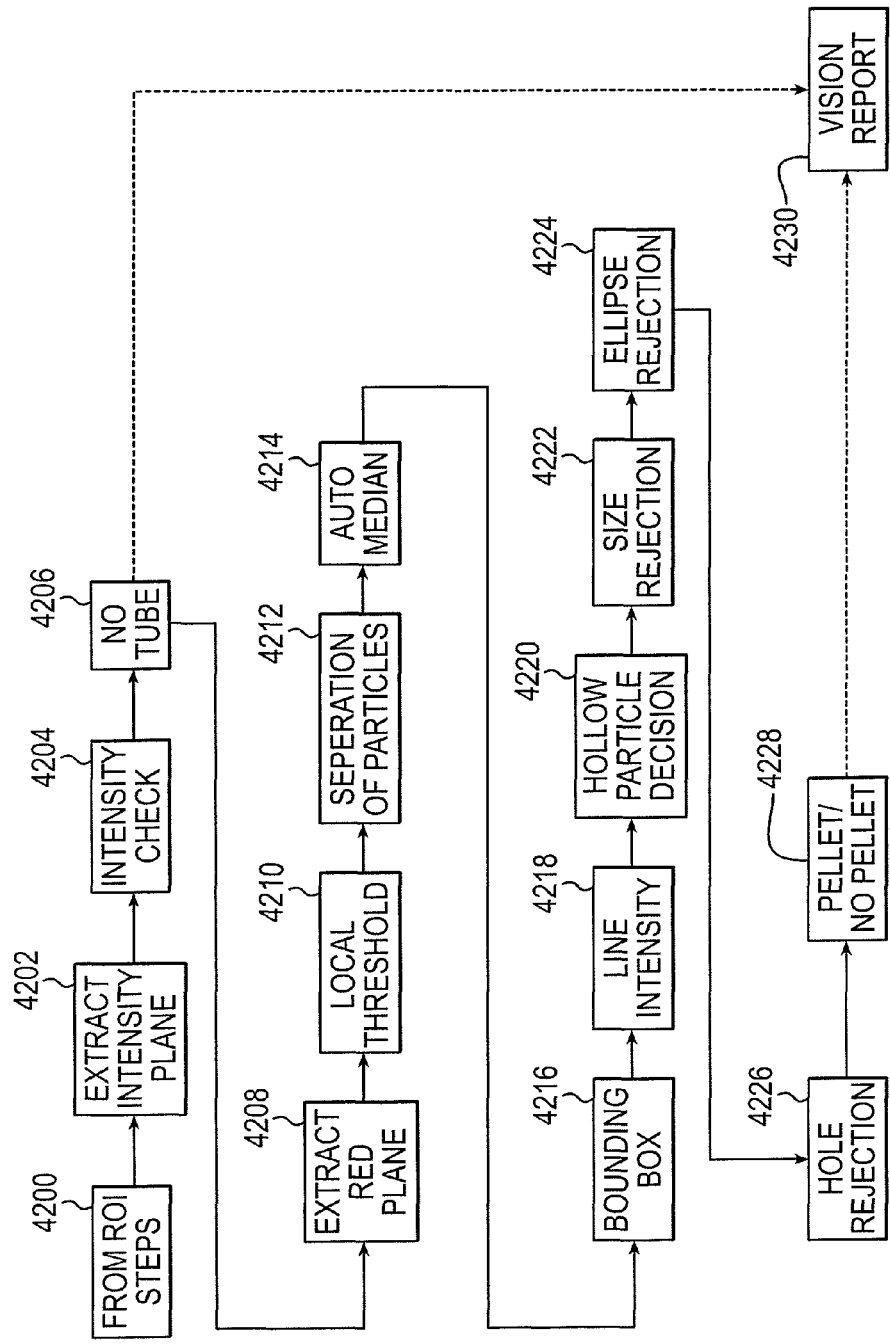

AUTOMATED PELLETIZED SAMPLE BLOTTING APPARATUS AND METHODS

BACKGROUND OF THE INVENTION

1. Field of the Invention

The present invention relates to automated systems and methods for preparing samples, such as biological samples. Particular exemplary embodiments relate to processing samples used to determine the presence or absence of human papillomavirus or other conditions.

2. Description of the Related Art

A wide variety of processing protocols are used in many different fields of art. Processing protocols are created and followed to help make sure similar items are processed the same way. The use of protocols helps provide consistent processing results and, where the results are not consistent, ensures that the differences are not attributable to variances caused by the processing itself.

Processing protocols are particularly important in the field of analytical biological science, in which biological samples are taken from a subject and processed to diagnose medical conditions, such as the presence or absence of a pathogen or viral infection. In many cases, it can be difficult, burdensome, uncomfortable, or even painful to obtain a sample from the subject, and therefore a high value is placed on taking great care with handling and testing the sample to prevent the need for multiple sample collection procedures. It is also may be desirable to perform as many tests as possible on the sample, and therefore the sample may need to be processed into multiple different sample aliquots to be tested using multiple different protocols. As a result, it is desirable to process as little of the sample as possible, to permit retests and alternative tests of a single collected sample. The desire to use smaller portions of each sample can place even stricter boundaries or requirements on sample processing protocols.

In some cases, analytical protocols may be regulated by government entities. For example, some testing protocols must be approved by the United States Food and Drug Administration before they can be introduced into commercial use. In such cases, the protocol must be followed not only as a matter of sound scientific principles, but also to stay within the scope of government-regulated activities.

One exemplary sample processing protocol is the QIAGEN Hybrid Capture® 2 ("HC2") nucleic acid hybridization assay. This protocol is used primarily for detecting human papillomavirus ("HPV") infections. The HC2 assay is an in vitro assay, in which RNA probes are hybridized with target DNA, the RNA:DNA hybrids are captured onto a solid phase, and the captured RNA:DNA hybrids are detected with multiple antibodies conjugated to alkaline phosphatase (a.k.a., signal amplification). The particular chemical and biological details of this process are known in the art and need not be detailed herein. The HC2 assay may be performed manually or through a combination of manual and automated processes. The manual sample preparation protocol for the HC2 assay includes a series of manual steps, which include (in general terms): reagent preparation, sample mixing/aliquoting, pelleting/decanting, denaturing, and transfer. The process begins with a sample collected from a subject and contained in a vial of preservative fluid (e.g., PreservCyt® or SurePath™). The details of the manual HC2 protocol steps, as performed on PreservCyt® samples, follow.

The reagent preparation step begins by adding 5 drops of indicator or dye to a denaturation reagent ("DNR") causing the DNR to turn dark purple. Next, the specimen transport medium ("STM") and DNR are combined in a 2:1 ratio and mixed by vortexing.

The sample mixing/aliquoting step is performed by vigorously shaking the PreservCyt® solution vial by hand or using a vortex mixer at maximum speed setting. Immediately after mixing, a volume of the PreservCyt® specimen solution is pipetted and delivered to the bottom of a conical sample processing container. The container is polypropylene, and may be a 10 milliliter Sarstedt conical tube or a 15 milliliter VWR or Corning brand conical tube.

The pelleting/decanting step involves a number of substeps. First, a predetermined amount of sample conversion buffer (e.g., 0.4 milliliters added to 4.0 milliliters of specimen for 1-2 tests per sample for samples in PreservCyt® media) is added to the processing tube, and then the tube is capped and thoroughly mixed using a vortex mixer with a cup attachment. Next, the tube is centrifuged in a swinging bucket rotor at 2,900 (±150)×g for 15 (±2) minutes. Following centrifuging, the operator visually verifies that a pink/orange cell pellet is present in the bottom of the tube. Even if no pellet is detected, the protocol continues, a pellet that is too small to see can still provide a positive test result (however, if there is no visible pellet, a negative test result might be dismissed as a false negative, and such an indeterminate result may require further testing). Next, the supernatant is carefully decanted by inverting the tube and gently blotting (approximately 6 times) on absorbent low-lint paper towels until liquid no longer drips from the tube. Each blot is done on a clean area of the towel. During blotting, the operator observes the tube to ensure that the cell pellet does not slide down the tube.

The denaturing step also includes a number of substeps. The step begins by adding a volume of the STM/DNR mixture (prepared in the reagent preparation step) to the pellet (e.g., 150 microliters of a 2:1 mixture of STM and DNR per 4 milliliter sample). Next, the pellets are resuspended by vortexing the tube. The operator may individually vortex the tube, or vortex it with other tubes on a MST Vortexer 2 machine. In either case, the tube is vortexed for at least 30 seconds at the highest speed setting. If the pellet is difficult to resuspend, it may be vortexed an additional 10-30 seconds or until the pellet floats loose from the bottom of the tube. After vortexing, the tube is placed in a rack, and the rack is placed in a 65° (±2°) Celsius water bath (with sufficient water to cover the liquid in the tube) for 15 (±2) minutes. Next, the tube is removed from the water bath, the exterior is dried, and the tube is vortexed again for 15-30 seconds (or, if it is vortexed on a MST Vortexer 2, for 1 minute) at the highest speed setting. After the second vortexing, the tube is again placed in a rack that is placed in a 65° (±2°) Celsius water bath (with sufficient water to cover the liquid in the tube) for 30 (±3) minutes. Following the second water bath tubes that were vortexed on a MST Vortexer 2 are vortexed once again at maximum speed for 10 seconds. Denaturing occurs during the first and second water bath steps.

The final step is to transfer the prepared specimen for hybridization. In this step, the operator pipettes 75 microliters of the prepared specimen into the bottom of an empty well in a hybridization microwell plate (e.g., a 96 well hybridization plate). After the microwell plate is loaded with specimens and calibrators or quality control samples, the plate is transferred to an automated or manual system for further processing to assess whether the sample is infected with a number of different HPV types (e.g., types 16, 18, 31, 33, 35, 39, 45, 51, 52, 56, 58, 59 and 68).

The foregoing HC2 protocol is just one example of a sample processing protocol that is used in conjunction with a sample assay process. Other protocols, and particularly manual protocols for preparing a sample in anticipation of further processing or evaluation, are known in the art. In some cases, the protocol is a regulated protocol that is indicated only for particular uses, and should be followed as closely as possible to maintain regulatory compliance.

Many sample processing protocols are specifically designed to be performed partially or entirely by hand. In some cases, the manual steps comprising the protocol may not be readily performed by an automated system. For example, the foregoing HC2 sample preparation protocol includes a number of steps particularly suited to manual operation (e.g., pellet observation, decanting, denaturing). These processes may not be readily-amenable to automated processing of multiple samples. Furthermore, where the protocol is regulated, it may be difficult to simulate the manual steps in an automated environment. Still further, even where a manual protocol is converted to an automated process, there may remain a question of whether the two processes are truly comparable, as numerous innocuous-seeming deviations from the protocol that are required by the automated process may, in fact, substantially affect the final results.

The conversion of manual protocols to automated processes can present many challenges, and numerous unforeseen issues often arise. Such issues require novel and unique solutions to ensure that the automated process is truly comparable to an existing manual protocol.

SUMMARY

In one exemplary embodiment, there is provided an automated sample tube blotting system having one or more rotating grippers, a supply of absorbent material, a transporter, and an absorbent material removal mechanism. Each rotating gripper has a respective holder configured to selectively mate with a respective interface on a tube strip, and the one or more rotating grippers are rotatable between a first position in which the tube strip is upright and a second position in which the tube strip is inverted. The transporter is configured to move the rotating gripper in a lateral direction from a starting location to a location above the absorbent material, and in a vertical direction towards and away from the absorbent material.

The recitation of this summary of the invention is not intended to limit the claims of this or any related or unrelated application. Other aspects, embodiments, modifications to and features of the claimed invention will be apparent to persons of ordinary skill in the art in view of the disclosures herein.

BRIEF DESCRIPTION OF THE DRAWINGS

A better understanding of the exemplary embodiments may be understood by reference to the attached drawings, in which like reference numbers designate like parts. The drawings are exemplary and not intended to limit the claims in any way.

FIG. 8 is a cutaway side view of a first exemplary ultrasonic sample adequacy detector.

FIG. 9 is a cutaway side view of a second exemplary ultrasonic sample adequacy detector.

FIG. 42 is a flowchart of an exemplary process for determining the presence of a pellet in an image such as shown in FIG. 38.

DETAILED DESCRIPTION

The exemplary embodiments described herein relate to automated sample preparation apparatus and methods, and an exemplary embodiments relate particularly to apparatus and methods used to automate the manual sample preparation steps associated with the HC2 protocol. However, it will be understood that embodiments of the invention can be used to prepare other kinds of sample. For example, the combination of pipetting, mixing, incubation, centrifugation, and decanting is applicable to DNA extraction, concentration, and purification as a front end to enzyme-linked immunosorbent assays ("ELISA"), non-amplified probe tagging or sandwich assays, and target amplification assays. The exemplary processing modules described herein may be readily modified to include additional equipment that might be necessary to perform alternative processes. For example, a processing module may be reconfigured to include magnetic bead binding, plate washing, and multiple optical detection devices.

Figure 1:
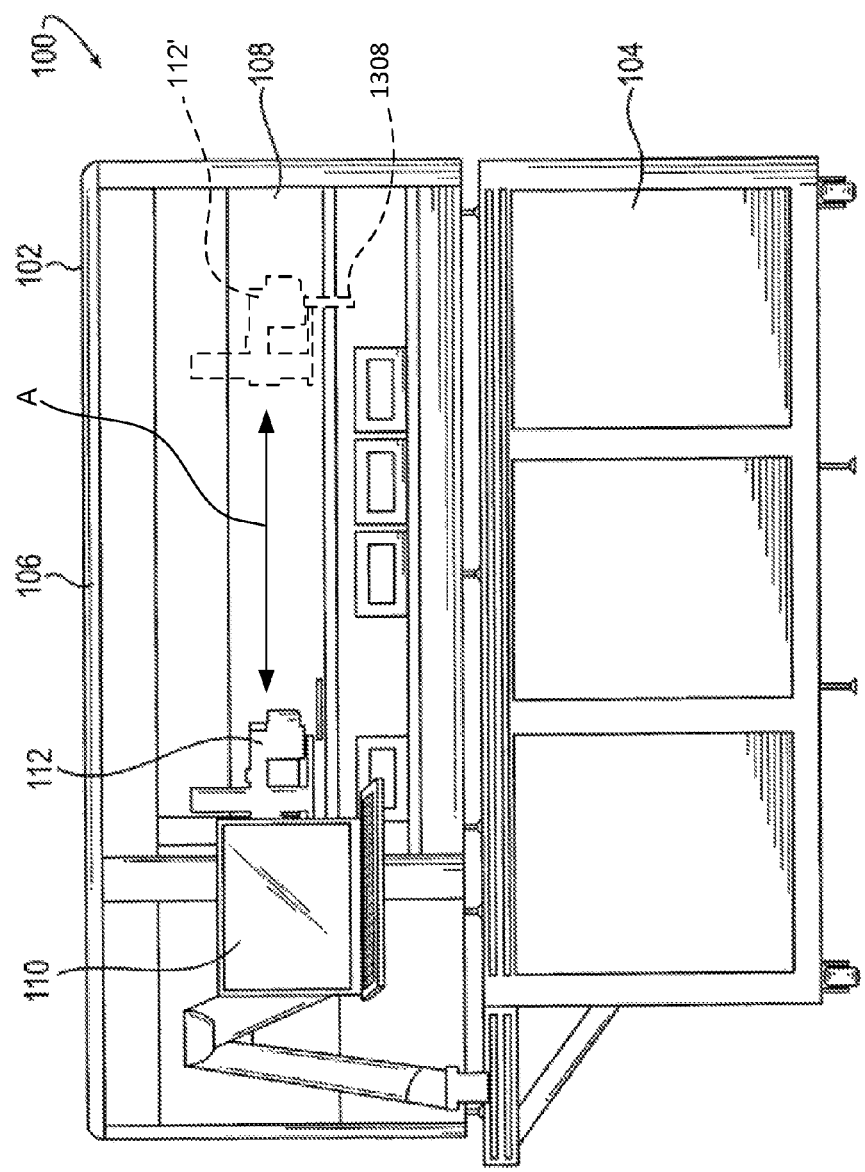
FIG. 1 is a front view of an exemplary sample preparation apparatus.

Referring to FIG. 1, an exemplary embodiment of an automated sample preparation apparatus 100 is illustrated. In general terms, the apparatus 100 includes a processing module 102 that may be mounted on a stand 104. The processing module 102 may contain some or all of the operating parts, storage facilities for supplies, and so on. The stand 104 may include additional components, such as a power supply, reagent supplies, consumable supplies, and the like. The stand 104 also may provide a mounting point to align and attach external components that are part of the processing module 102 (e.g., computer hardware, centrifuges, vision systems, etc.). The stand 104 may be incorporated into the processing module 102 to form a large processing module 102, but alternatively the processing module 102 may be operationally independent of the stand 104 so that the processing module 102 can be used as a table-top unit. The processing module 102 preferably includes a housing 106, having one or more openable covers, such as a transparent front panel 108. Suitable lockout systems may be provided to prevent operation when the housing 106 is open. The apparatus 100 may also include a computer processing unit, which may be integrated into the processing module 102, located in a remote or separate processor such as an external computer 110, or distributed over a network of communicating processors. The computer processing unit may be operatively connected to a variety of robotic devices located in the processing module 102, such as pipettors 112, transport mechanisms, heaters, optical equipment, shakers, barcode readers, and the like. FIG. 1 shows the pipettors 112 moved to a second position 112' as shown by arrow A.

Figure 2:
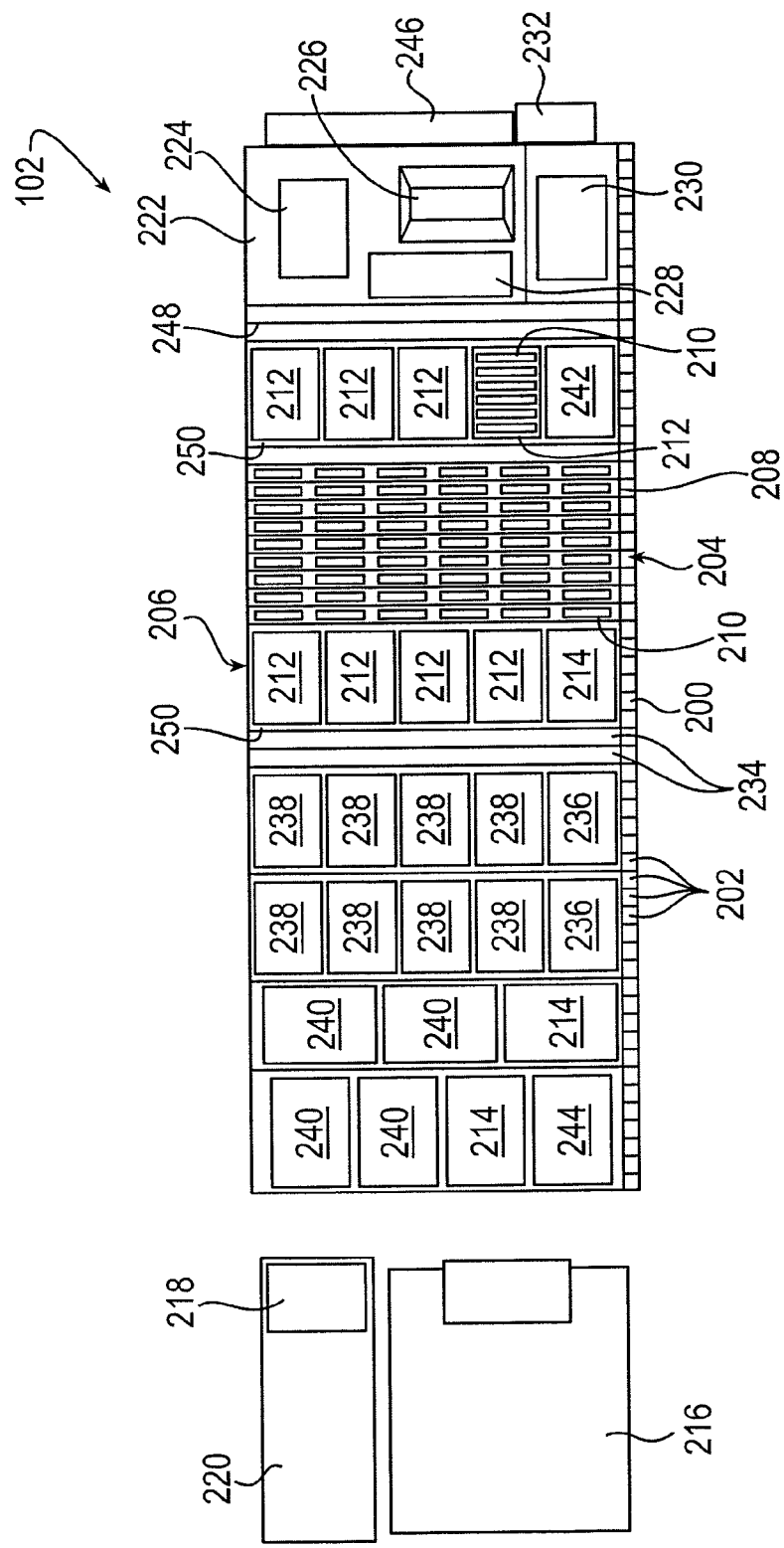
FIG. 2 is a schematic plan view of an exemplary processing module.

Referring to FIG. 2, an exemplary processing module 102 is illustrated in schematic plan view. The processing module 102 may be assembled, in whole or in part, on a flat platform 200 comprising a number of uniformly-shaped and uniformly-distributed lanes 202 that extend from the front 204 of the module 102 to the back 206 of the module (for clarity, only some of the lanes 202 are marked by reference number 202). The lanes 202 may include physical dividers, mounting racks, mounting holes, and other features to permit installation, removal, replacement, and possibly rearrangement, of various working parts of the processing module 102. Such automated system platforms 200 are known in the art and need not be described further herein.

The processing module 102 of FIG. 2 is configured for automated processing of samples in an automated equivalent to the manual HC2 protocol. However, other uses are envisioned for this or other configurations of a processing module 102.

The processing module 102 includes a number of tube strip racks 208 in which tube strips 210, such as the embodiments described subsequently herein, are provided. Each tube strip 210 includes a plurality of tubes, and each tube may contain a separate specimen for processing. Tube strips 210, or individual tubes in a tube strip 210, also may contain calibrators or quality controls (or no sample). For purposes of this description, the contents of each tube will be considered to be a "sample" regardless of whether its contents are a patient's specimen, a calibrator, a quality control, or nothing at all. In this embodiment, each tube strip 210 has four tubes, each tube strip rack 208 can hold up to six tubes strips 210. Nine tube strip racks 208 are illustrated, but eight racks 208 or other numbers of racks 208 may be provided. The tube strip racks 208 may be provided in adjacent lanes 202, or otherwise distributed.

Tube strip holders 212, such as those described subsequently herein, are also provided in the processing module 102. The tube strip holders 212 are configured to hold one or more tube strips 210 for transport through the processing module 102, and during further processing steps. In this example, there are eight tube strip holders 212, and each can hold six tube strips 210. Thus, each tube strip holder 212 can hold up to twenty-four samples. The tube strip holders 212 may be provided next to, or on either side of, the tube strip racks 208. For example, four tube strip holders 212 may be provided on each of two platforms mounted to the lanes 202 located on either side of the tube strip racks 208.

The processing module 102 also may include one or more mixing devices, such as orbital shakers 214. The orbital shakers 214 may include a heater or chiller to heat or cool the samples in the tubes. The orbital shakers 214 or other mixing device may be any device suitable for mixing the contents of the tubes, and preferably is able to mix the tubes without removing them from the tube strip holders 212. For example, the orbital shakers 214 may be Hamilton Heater Shakers available from Hamilton Robotics of Reno, Nev. The orbital shakers may be operated at room temperature (i.e., no heating), or at a predetermined temperature controlled by heating elements coupled to the shakers (e.g., a resistance coil or the like). Multiple orbital shakers 214 may be provided for simultaneous, separate, processing of multiple tube strip holders 212. The shown orbital shakers 214 each hold a single tube strip holder 212.

One or more centrifuges 216 may be provided in or with the processing module 102. In the exemplary embodiment, a centrifuge 216 is provided adjacent one end of the platform 200. The centrifuge 216 may be mounted on the platform, but (like the other components described herein) this is not required. In the shown embodiment, the centrifuge 216 is connected to the processing module 102 independently of the platform 200, which may assist with supporting the large weight of the centrifuge 216, and isolating the centrifuge 216 during operation. An example of a centrifuge that may be used is the HiG™ centrifuge available from BioNex Solutions, Inc., of Sunnydale, Calif.

The processing module 102 also may include one or more vision inspection stations 218. The vision inspection station 218 may be located in a camera enclosure 220 having one or more cameras and one or more light sources. If necessary, the camera enclosure 220 may be closable to prevent ambient light from interfering with the procedures carried out by the vision inspection station 218. One exemplary vision inspection station 218 may be provided in the STAR Line of products from Hamilton Robotics of Reno, Nev. Other sample inspection devices, such as turbidity meters and the like, may be used in other embodiments.

A decanting station 222 also may be provided in the processing module 102. The decanting station 222 may comprise a system adapted to decant fluid from the sample tubes. An exemplary embodiment of a decanting station 222 is described in detail subsequently herein. As shown in FIG. 2, the decanting station 222 may include a retainer 224 to hold a tube strip holder 212 while individual tube strips 210 are removed and decanted. The decanting station 222 also includes a decant waste well 226 to receive the supernatant decanted from the tubes. The decanting station 222 may also include a gripper parking location 228 to receive grippers used in the decanting process or other processes.

A tube strip lid holder 230 may be provided to hold a supply of one or more tube strip covers, such as those described subsequently herein. If a separate gripper or gripping tool is used to manipulate the tube strip covers, it may be stored in a cover gripper parking location 232.

The processing module 102 may include one or more liquid supplies, such as reagent reservoir racks 234. The reagent reservoir racks 234 may be slidably mounted on the platform lanes 202 for ease of removal and refilling. The reagent reservoir racks 234 may include any reagent or combination or reagents used for the processing steps conducted by the processing module 102. For example, each reagent reservoir rack 234 may have five 50 milliliter reservoirs. The contents of the reservoirs may vary, and may include transport media, denaturation reagents, sample conversion buffers, and the like. In other embodiments, liquid supplies may be provided in bottles or other containers located elsewhere in operative association with the processing module 102. For example, liquid supplies may be provided in the stand 104 and connected by hoses to dispensers (not shown) in the processing module 102.

Pipette tip storage units 236, 238 may be provided to supply disposable pipette tips. In the example shown, there are two 5-milliliter pipette storage units 236 that each hold 24 tips, and eight 1-milliliter pipette storage units 238 that each hold 96 tips. Other numbers and variations of pipette storage arrangements may be used in other embodiments, and these may be omitted if they are not necessary, or replaced with other disposable supply units.

The processing module 102 also may include heating units 240, such as heated water baths or the like. The heating units 240 may be configured to heat the individual tube strips 210, individual tubes (if used instead of tube strips 210), or tube strips 210 that are mounted in tube strip holders 212. In a preferred embodiment, the heating units 240 may have heat distribution features configured to help uniformly heat tube strips 210 that are mounted in tube strip holders 212. One example of a heat distribution feature is described subsequently herein, but variations of the shown example, or other devices, may be used in other embodiments of processing modules 102. If desired, the heating units 240 may also be equipped to mix the contents of the tubes during the heating process. For example, the heating units 240 may comprise Hamilton Heater Shakers available from Hamilton Robotics of Reno, Nev. Such units may be modified or used in their original form.

The processing module 102 may be configured to hold one or more output plates 242, such as typical 96-well plates. The output plates 242 may be used to store processed samples, or to hold the samples in advance of further processing. For example, the sample plates 242 (which are sometimes be referred to as "hybridization" plates) may be configured for subsequent manual or automated performance of additional steps to complete the HC2 protocol. In the embodiment of FIG. 2, the output plates 242 may be mounted on a sliding rack 250 along with one or more (in this case, four) tube strip holders 212. This allows simultaneous loading of tube strip holders 212 and output plates 242. Conveniently, the parts may be arranged so that the number of samples that are held in the tube strip holders 212 equals the number of wells in the output plate (in this case, the number is ninety-six). In this way, the entire rack 250 can be removed when processing is complete, and reloaded with empty tube strip holders 212 and an output plate 242 to quickly and efficiently prepare for a new processing run.

The output plates 242 may be covered by a lid. The lids may be provided with the output plates 242 when the output plates 242 are loaded into the processing module 102, or a supply of lids may be provided in the processing module 102. The processing module 102 may include a lid holder 244 that holds a supply of lids, or provides a place to store each output plate's lid as the output plate 242 is being filled.

The processing module 102 may include other features, such as a tip eject station 246 to receive used pipette tips, or other waste chutes or containers for disposables. Another feature may be an additional tube strip rack 248 that holds additional empty tube strips 210. The empty tube strips 210 may be placed in the tube strip holder 212 to balance the centrifuge 216 if a tube strip holder 212 is processed without a complete set of sample-filled tube strips 210.

The various samples containers, consumables and supplies may be loaded by opening the cover 108 or other access doors. However, in a more preferred embodiment, at least some of these may be accessible through one or more uncovered openings. For example, the tube strip racks 208 and reagent reservoir racks 234 may be accessed through an opening under the bottom edge of the cover 108, to permit removable and replacement to allow continuous resupply during operation.

A suitable robotics system may be provided in the processing module 102 and configured and programmed to conduct the processing steps described herein. For example, automated pipetting and material handling systems, such as the pipettors, autoloaders, iSWAP microplate grippers, and CORE grippers in the STAR Line of robotics provided by Hamilton Robotics of Reno, Nev., may be used to pipette fluids and transport tube strips 210 and tube strip holders 212 throughout the processing module 102. Pipette control systems that use one or more sensors or algorithms to detect clots or otherwise monitor aspiration properties also may be used for any of the pipetting steps described herein. Other features, such as safety locks, lights, ventilation or seals, consumable supplies, and the like, may be included in or with the processing module 102, as desired for the particular application.

It will be understood that the various components may be rearranged, such as by swapping locations or stacking them on vertically-displaced decks. Other embodiments also may use different numbers of processing stations and different numbers of supplies and samples, and the like. Other variations and modifications will be apparent to persons of ordinary skill in the art in view of the present disclosure.

Figure 3:
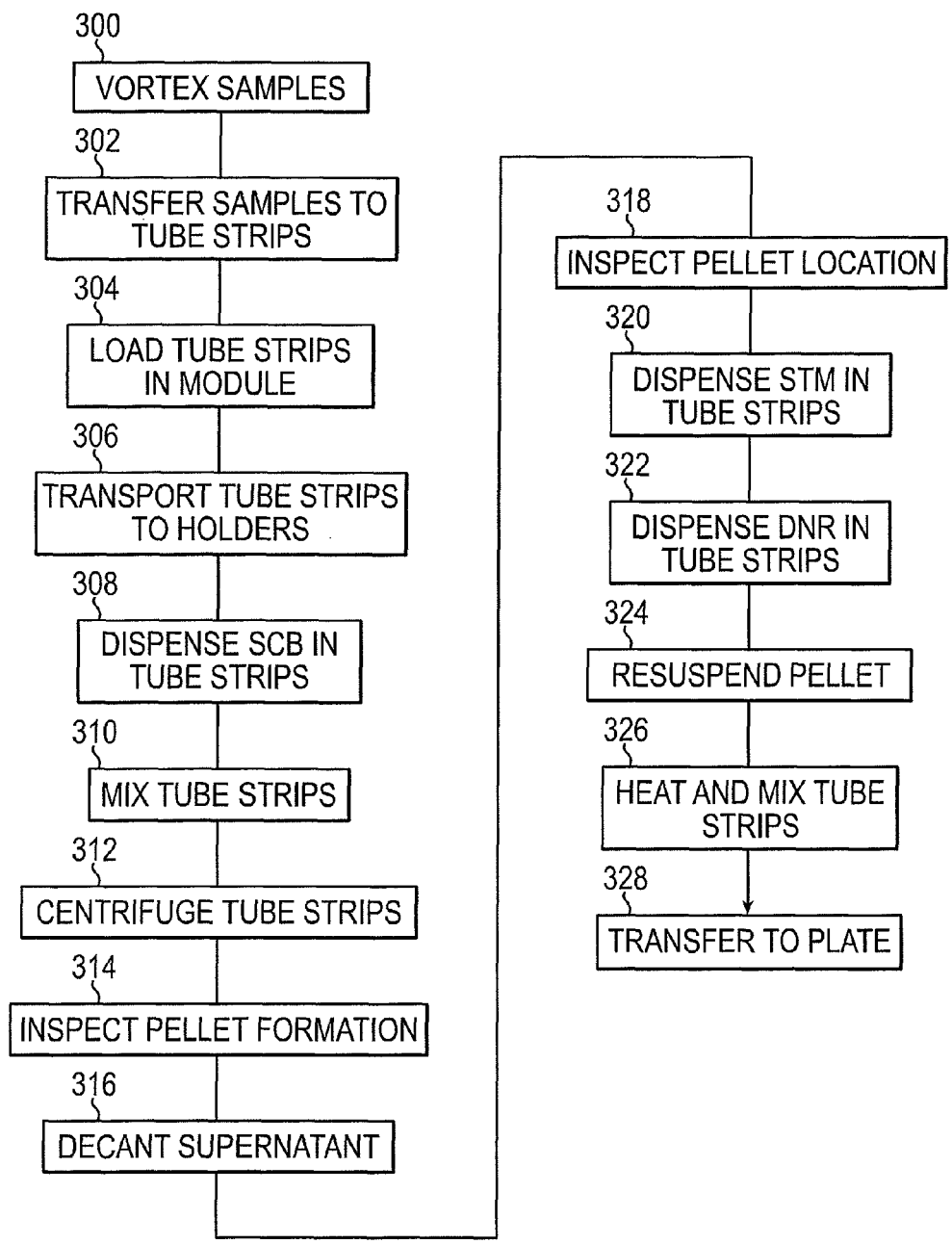
FIG. 3 is a flowchart of exemplary process steps for operating a sample processing module.

FIG. 3 illustrates an exemplary process that may be performed, at least in part, by a processing module 102 such as the exemplary embodiment of FIG. 2. In this embodiment, the process is an automated equivalent of a manual HC2 processing protocol. Before the process begins, an operator may manually add 5 drops of indicator or dye to a denaturation reagent ("DNR") causing the DNR to turn dark purple. This is the same as the conventional manual HC2 protocol. At step 300, the operator resuspends one or more samples provided in individual containers (e.g., sample collection tubes), either by hand or by using a conventional table-top vortex mixer. The samples may be provided in any kind of sample vial or container. In the case of HPV testing, individual patient samples are often provided in PreservCyt® vials available from Hologic, Inc. of Marlborough, Mass. Such PreservCyt® vials are commonly used to collect cervical samples, and each vial includes a sample from a single patient and a preservative liquid. Other common sample formats include the SurePath™ format from Becton, Dickinson and Company of Franklin Lakes, N.J., and others.

Next, in step 302, the operator manually aliquots a 4 milliliter specimen from each sample into a respective tube of a tube strip 210. This manual step may be done using the same method that the HC2 protocol indicates for manually transferring the sample to a sample processing container. Next, in step 304 the operator loads the filled tube strips 210 into the tube strip racks 208, and loads the tube strip racks 208 into the processing module 102. In the embodiment of FIG. 2, the operator can load enough tube strips 210 to fill two 96-well output plates 242, but other capacities may be used. The operator may continue loading tube strips 210 after processing begins, in order to provide enough samples to fill additional output plates 242. Steps 300 and 302 may be performed manually, but in other embodiments some or all of these steps may be performed by another processing system that operates outside the processing module 102, or in the processing module 102 itself.

Next, in step 306, the processing module 102 transports the tube strips 210 to a tube strip holder 212. The tube strips 210 may be manipulated by any suitable transport mechanism, such as the transport grippers described subsequently herein. It will be appreciated that step 306 may alternatively be performed after step 308 described below, in which case the Sample Conversion Buffer ("SCB") would be dispensed into the tube strips 210 before they are loaded into the tube strip holder 212.

In step 308, the processing module 102 activates one or more pipettors, such as a ganged group of four or eight pipettors, to withdraw conventional HC2 protocol SCB from the reagent reservoirs 234, and dispense the SCB into the samples contained in the tube strips 210. The processing module 102 can operate the pipettors and other devices using any control system, such as an internal or external processor. In keeping with the manual HC2 protocol, 400 microliters of SCB may be dispensed into each tube, but other volumes may be dispensed in other embodiments. The pipetting process may also include moving the pipettors to a disposable pipette tip supply, such as a 5-milliliter pipette storage unit 236, moving the pipettor to engage disposable tips before withdrawing the SCB, and moving the pipettor to deposit the used pipette tips into the tip eject station 246 after dispensing the SCB. In other embodiments, this or other fluid deposition steps may be performed by dispensers or other devices that are plumbed directly to fluid reservoirs, to minimize the need to use disposable pipette tips or increase processing speed.

In step 310, each tube strip holder 212 is transported to an orbital shaker 214, where the samples in the tubes are mixed. Any suitable transport mechanism may be used for this step and for other transport steps described herein. In an exemplary embodiment, the tubes are mixed at room temperature by operating the orbital shaker 214 for 30 seconds at 800 rpm on a 3 millimeter orbit.

Next, in step 312, the tube strip holder 212 is loaded into the centrifuge 216 and centrifuged at 2,900 gravities for 15 minutes. The centrifuging step is expected to cause the samples in the tubes to create cell pellets at the bottom of each tube.

To verify that a pellet has formed in each tube, in step 314 the processing module 102 loads the tube strip holder 212 into the vision inspection station 218. Here, the tubes are visually inspected, preferably all at one time, to evaluate whether a pellet has formed in each tube. In the shown embodiment, verification may be performed using a camera below the tubes, and a light above the tubes, but a reverse arrangement or other arrangements or detecting devices may be used. If there is no pellet, a record is made of the tube lacking a pellet, and the process continues. The visual image generated in step 314 may be printed or electronically stored for future reference. Step 314 may be omitted in an alternative embodiment. For example, the HC2 protocol calls for checking the presence of the pellet after centrifuging, but does not necessarily modify the remaining process depending on the outcome of this inspection; thus, for an automated version of the HC2 protocol, step 314 may optionally be omitted.

In step 316, the tube strip holder 212 is transported to the decanting station 222, where it is placed on the retainer 224 for storage during the decanting process. In the exemplary embodiment, the decanting process may be performed by sequentially removing each tube strip 210 from the tube strip holder 212, inverting the tube strip 210 to decant the supernatant from each tube into the decant waste well 226, turning the tube strip 210 upright, and replacing it in the tube strip holder 212. The tube strips 210 may be decanted by devices such as those described elsewhere herein, or by other mechanisms. For example, two pipette channels may be used to pick up decanting grippers from the gripper parking location 228, and the pipette channels and decanting grippers may be used to rotate the tube strip 150 degrees to decant the fluid. The rotation speed, rotation angle, and decanting time may be adjusted to obtain the results desired for the particular application. In an alternative embodiment, the tube strips may remain in the tube strip holder 212 during step 316, in which case the retainer 224 may be omitted. For example, the decanting process may be replaced with an aspiration step, in which the tube strips 210 remain upright, and supernatant is removed by aspiration.

Immediately after decanting, it may be desirable to blot the tube strips 210 to help remove any fluid that remains in or on the tubes. An example of a blotting system is described below. Such a process step is not required in all embodiments.

Following decanting and replacing the tube strips 210 to the tube strip holder 212, in step 318 the tube strip holder 212 is returned to the vision inspection station 218. In this step, the vision inspection station 218 is operated to verify that the pellet remains in each tube. If a pellet is missing, a record is made of the tube lacking the pellet, and the process continues. The visual image generated in this step may be printed or electronically stored for future reference. Following inspection, the tube strip holder 212 is moved to its original location (e.g., on sliding rack 250), or to an intermediate holding location.

Next, in step 320, the processing module 102 operates the pipettors to load pipette tips, such as disposable 1 milliliter tips from one of the 1-milliliter pipette storage units 238, withdraw HC2 protocol Specimen Transport Medium ("STM") from the reagent reservoirs 234, dispense the STM into the samples contained in the tube strips 210, and eject the used pipette tips into the tip eject station 246. In one embodiment, a volume of 100 microliters of STM is dispensed into each tube, but other volumes may be used in other embodiments.

In step 322, the processing module 102 essentially repeats step 318, but in this step it withdraws HC2 protocol Denaturation Reagent ("DNR") from the reagent reservoirs 234, and dispenses the DNR into the samples in the tube strips 210. In one embodiment, a volume of 50 microliters of DNR is dispensed into each tube, but other volumes may be used in other embodiments. Steps 318 and 320 may be reversed or performed simultaneously in other embodiments.

In step 324 the tube strip holder 212 is moved to a room-temperature orbital shaker 214 to resuspend the pellets in the tubes. The orbital shaker 214 is operated for two minutes at 1,250 rpm on a 3 millimeter orbit. If necessary, a cover, such as the covers described below, may be placed on the tube strip holder 212 prior to this mixing step to prevent cross-contamination during the mixing process.

Next, in step 326, the tube strip holder 212 is moved to a heater-shaker 240 and the samples in the tube strip holder 212 are heated and periodically mixed. If a cover is not already on the tube strip holder 212, one may be installed prior to heating. In an exemplary embodiment, the samples are heated to 65° (±2°) Celsius for 15 minutes, mixed (while still heating) at 1,250 rpm on a 3 millimeter orbit for 30 seconds, heated for another 30 minutes, and mixed at 1,250 rpm on an orbit of 3 millimeters for 10 seconds. The target temperature is maintained for the entire heating and mixing process, yielding a total incubation time of approximately 45 minutes and 40 seconds.

In step 328, the tube strip holder 212 is transported to its original location, such as the sliding rack 250, or moved to an intermediate holding station. The processing module 102 removes the cover from the tube strip holder 212 using any suitable gripper or transport mechanism, and stores or disposes of the cover. In order to prevent cross-contamination caused by condensation or liquid clinging to the cover, the cover may be removed by lifting it straight up from the tube strip holder 212. The processing module 102 also removes the lid from the output plate 242 (if one is provided) and places it on the lid holder 244. Next, the pipettors pick up tips (e.g., 1-milliliter tips) and transfer 75 microliters of sample from each tube to an empty well in the output plate 242. It may take several tube strip holders to completely fill the output plate 242. For example, one output plate 242 may receive samples from four tube strip holders 212. Some of the output plate 242 wells may be loaded with controls or other non-sample contents. Once the output plate 242 is filled or deemed to be sufficiently filled for further processing, the lid is replaced on the output plate 242. Once it is filled, the output plate 242 may be immediately removed from the processing module 102, or stored in the processing module 102 for a period before it is removed.

To reduce processing times, the processing module 102 may have multiple essentially identical processing devices or equipment that are operated at the same time to process different samples. For example, the processing module 102 may have four heater-shakers 240 to process four tube strip holders 212 at the same time or in close succession.

The process described with reference to FIG. 3 may also include any number of intermediate steps, such as steps taken to track samples or to ensure processing stability. For example, barcodes may be provided on the tube strips 210 and tube strip holders 212, and these barcodes may be read periodically to track sample locations. Also, the processing module 102 may be programmed to run a predetermined number of specimens as a batch to ensure that all necessary supplies and reagents are available to completely process all of the specimens without interrupting the run. However, if the number of specimens is less than the available output volume (e.g., if 192 wells are available on two output plates 242, but there is only room to load 96 samples at a time), the processing module 102 may be programmed to allow more samples to be loaded during operation to fully utilize the output capacity.

Figure 4:
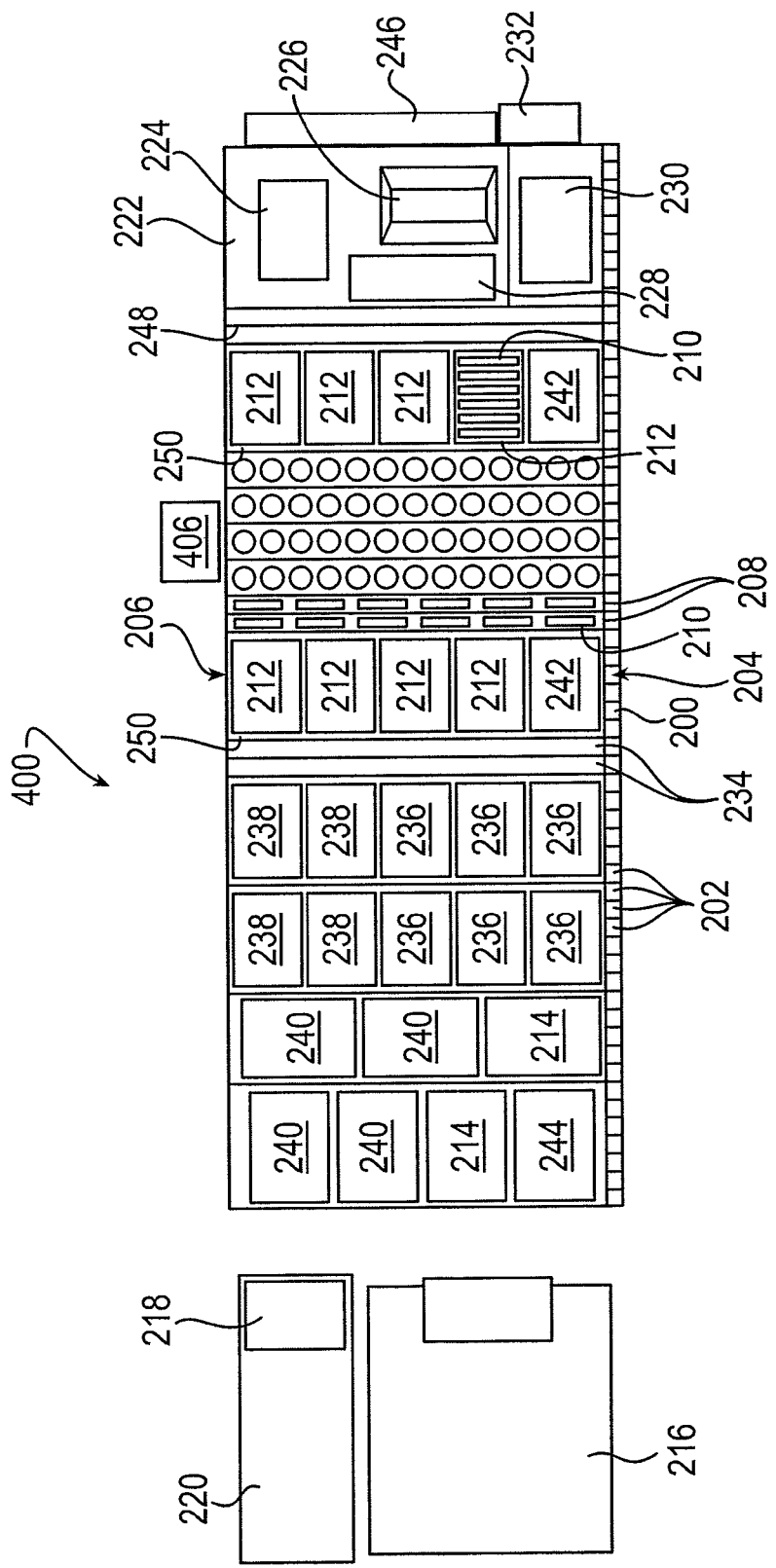
FIG. 4 is a schematic plan view of another exemplary processing module.

FIG. 4 illustrates another exemplary processing module 400. Processing module 400 may have a number of elements in common with the embodiment of FIG. 2, and such parts are designated by the same reference number. The embodiment of FIG. 4 may be a deviation of the embodiment of FIG. 2, and in a preferred embodiment a single set of equipment can be assembled as shown in FIG. 2 or as shown in FIG. 4. The use of sliding racks and the like may facilitate such conversion by allowing simple moving, removal and replacement of parts. Suitable reprogramming of the apparatus can be done along with the conversion, either automatically or manually. For example, the processing module 400 may be switched by an operator into an alternative, pre-programmed operating mode, or the replacement parts may be coded (e.g., by radio frequency identification tags or barcodes) to automatically indicate to the processing module 400 that a change has been made and/or that reprogramming to a different operating mode may be required. If the system is configured to recognize the parts and their locations, the system may automatically switch operating modes upon recognizing a known arrangement of parts, and may transmit an error message if the arrangement is not recognized.

The processing module 400 of FIG. 4 differs from the embodiment of FIG. 2 primarily in the replacement of a number of tube strip racks 212 with vial racks 402. The vial racks 402, which may be racks that slide into the platform lanes 202, are each configured to hold one or more sample vials 404. In this case, seven tube strip racks 212 are removed, and replaced by four vial racks 402. In this example, each vial rack is capable of holding up to twelve sample vials 404, yielding a maximum of forty-eight sample vials 404. Other numbers of racks and vials may be used in other embodiments. Other modifications, as compared to the embodiment FIG. 2, include the removal of the empty tube strip rack 248, and moving the right-hand sliding rack 250 to make room for the vial racks 402.

The embodiment of FIG. 4 facilitates a modified operation mode in which samples are provided to the system in individual sample vials 404. This is in contrast to the embodiment of FIG. 2, in which specimens are provided to the apparatus pre-dispensed into tube strips 210. The sample vials 404 may be any suitable sample vial. For example, in the case of HPV testing, the sample vials 404 may comprise one or more varieties of PreservCyt® or SurePath™ vials.

The vial racks 402 may hold the sample vials 404 in any suitable fashion. For example, each vial rack 402 may have a plurality of vial wells in which the sample vials 404 are dropped before sliding the vial rack 402 into the processing module 400. Such wells may be vertical or tilted at an angle, such as an angle between 5° and 20° from vertical (e.g., 10° from vertical may be suitable for some typical sample vials 404), to facilitate pipetting of the contents from the sample vials 404. The wells also may be mounted to tilt during the pipetting process. The wells may have openings or slots through which barcodes on the sides of the sample vials 404 can be read before, during, or after insertion of the vial rack 402 into the processing module 400. The sample vials 404 may be provided in the vial racks 402 with their caps removed, or a decapping/recapping unit may be integrated into the processing module 400 to remove and replace the vial caps during processing. If desired, the vial racks 402 may include features, such as shakers or the like, to suspend the samples.

Where individual sample vials 404 are processed by the processing module 400, it may be desirable to provide features and systems to evaluate the adequacy of the sample for further processing or the need for corrective processing. For example, a sample adequacy system in the form of a turbidity instrument or ultrasonic testing instrument 406 may be provided to determine whether the sample has sufficient cell count to warrant further processing. A preliminary check of this sort can avoid unnecessary processing, which can save on reagent cost and processing time, and also prevent the recording of a false negative result. An example of an ultrasonic sample adequacy detection system is described subsequently herein. This or other sample adequacy detection devices may be incorporated anywhere in the processing module.

As noted above, processing module also may include pipette control systems to detect clots or otherwise monitor aspiration properties. This may be particularly desirable where the samples are provided as an original, unprocessed biological sample, such as in a PreservCyt® or SurePath™ vial. Such samples may include tissue, clots, and other features that might inhibit proper pipetting.

Figure 5:
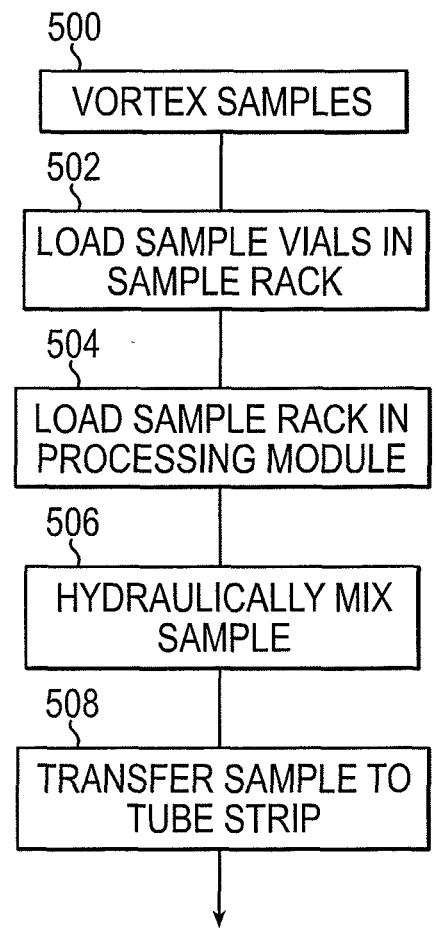
FIG. 5 is a flowchart of exemplary process steps for operating a sample processing module.

FIG. 5 is an exemplary process for operating processing module 400. In step 500, the operator vortexes (e.g., in a vortex mixer at its maximum setting) or vigorously shakes each sample vial 404 to resuspend the sample. Next, in step 502, the operator loads each sample vial 404 into a sample rack 402, and, if applicable, orients any barcode or other computer-readable indicator so that it can be read as the sample rack 402 is inserted into the processing module 404. Next, in step 504 the operator loads the sample rack 402 into the processing module 400. After processing begins, the operator may remove sample racks 404 that have been processed, and replace them with filled sample racks 404, to provide continuous operation to process a large number of specimens. The foregoing steps may be performed manually or by another processing system that operates outside the processing module 400.

In step 506, the processing module 500 operates the pipettors to load pipette tips, such as 5-milliliter disposable pipette tips, and hydraulically mix the contents of each sample vial 404. Hydraulic mixing may be performed, for example, by drawing a volume from of each sample vial 404 into the pipette tip expelling the volume back into the sample vial 404. This may be repeated one or more times to obtain the desired mixing results. In alternative embodiments, shakers or other devices may be used to mix the samples.

Following mixing, in step 508 the processing module 500 operates the pipettors to transfer a volume of each sample, such as 4 milliliter aliquot, to a respective tube in a tube strip 210. A clot detection system or other algorithm may be used to determine whether sample is properly pipetted, and such algorithm may include a process to retry pipetting if a failure condition is detected. If a failure is detected and cannot be overcome, the processing module 400 may associate a record of the failure with the particular sample vial 404. The same pipette tip that was used for hydraulic mixing is used to transfer the sample. Used tips are disposed in the tip eject station 246. If a clot is detected on the outside of a pipette tip it may drip and contaminate the instrument or samples. In this scenario the tip can be placed into the sample vial 404 and left there to prevent cross-contamination. Steps 506 and 508 can be performed simultaneously on a number of samples using a ganged pipettor. If adjacent sample tubes 404 on the sample rack 402 are spaced apart by a different distance than adjacent tubes in the tube strip 210, it may be desirable to use a pipettor assembly with variable channel spacing to accommodate the different spacings.

The foregoing process also may include manually adding 5 drops of indicator or dye to the HC2 DNR causing the DNR to turn dark purple, as done in the manual HC2 protocol. This step may be performed at any time prior to the DNR being used in the remaining process steps. This step also may be automated into the processing module's functions.

Following step 508, the tube strips 210 are processed, such as described above, to convert the specimens and transfer them to output plates 242. For example, step 508 may be followed by step 305 (dispensing SCB into the tube strips 210), and the remaining steps until the specimens are transferred to plates in step 328.

Figure 6:
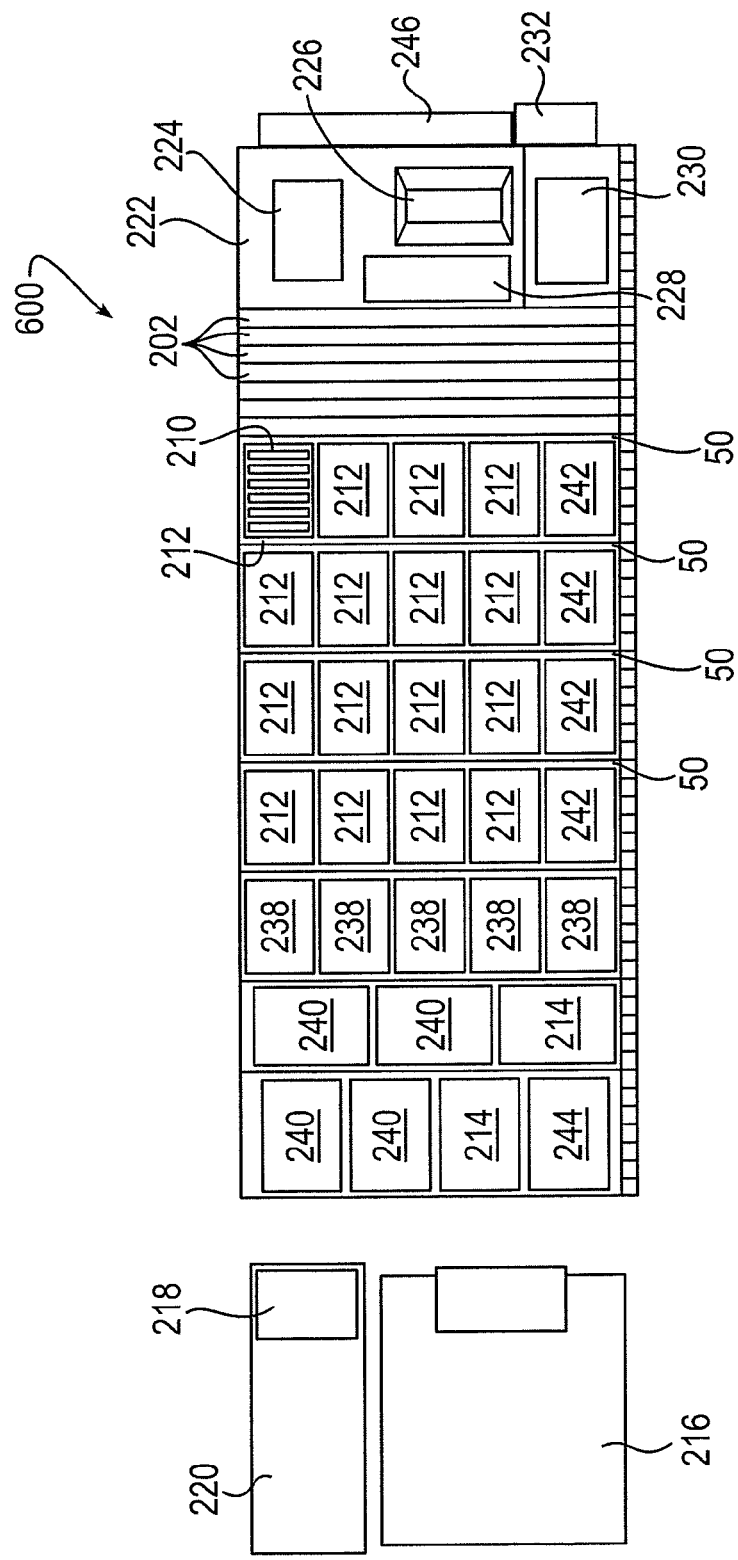
FIG. 6 is a schematic plan view of another exemplary processing module.

FIG. 6 shows another embodiment of a processing module 600. This embodiment may be a separate construction, or a modification of the earlier-described processing modules 102, 400. The embodiment of FIG. 6 is configured to start the process with samples provided in tube strips 210 that are already loaded into tube strip holders 212. For example, the tube strip holders 212 may contain tube strips 210 that were previously processed through step 326 of FIG. 3 by a processing module 102 as shown in FIG. 2, and then stored (e.g., refrigerated or frozen) prior to step 328 of FIG. 3. In this embodiment, the processing module 600 is used to perform step 328 of FIG. 3—that is, to transfer the processed samples from the tube strip holders 212 to output plates 242. The arrangement is expected to be helpful to schedule more efficient overall processing times where large volumes or interruptions (e.g., the end of a working shift) are expected to occur.

The embodiment of FIG. 2 may be configured as shown in FIG. 6 by removing all of the tube strip racks 208 (including the rack of empty tube strips 248) and reagent reservoirs 234, and installing two or more sliding racks 250 holding tube strip holders 212 and output plates 242. Alternatively, the tube strip racks 208, 248 and reagent reservoirs 234 may remain in place and left unused during processing.

Figure 7:
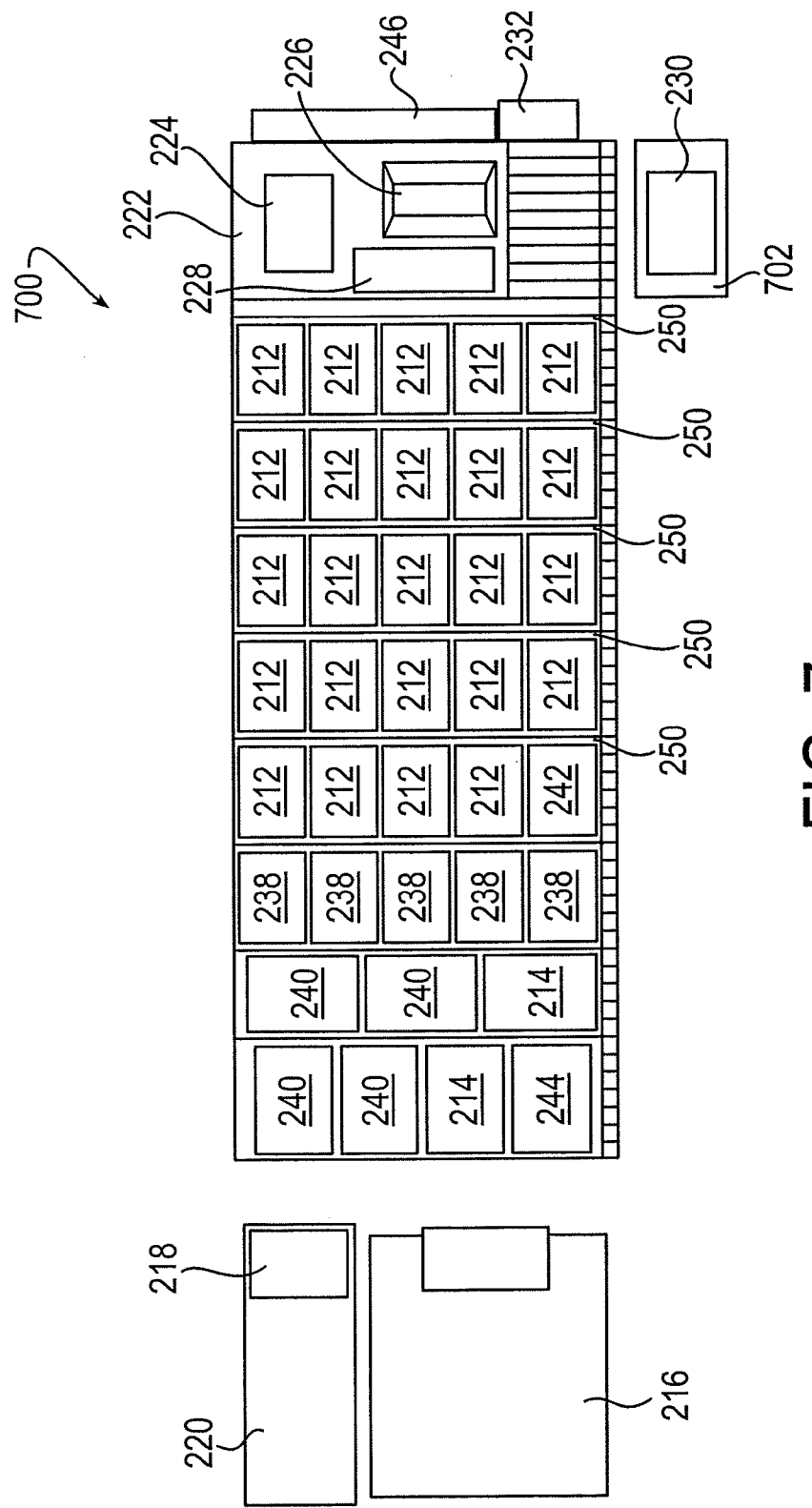
FIG. 7 is a schematic plan view of another exemplary processing module.

FIG. 7 shows another alternative embodiment of a processing module 700 that is set up for rapid retesting preparation. This embodiment also may be a permutation of the foregoing processing modules 102, 400, 600, or a separate construction.

Here, the reagent reservoirs 234, tube strip racks 208, 248 and vial racks 402 are omitted, and replaced by sliding racks 250. One sliding rack 250 holds an output plate 242 and four tube strip holders 212, and four additional sliding racks 250 hold more tube strip holders 212. This arrangements increases, and may maximize, the number of tube strip holders 212 that are held by the apparatus without requiring substantial modification. It may be necessary to remove other components, such as the tube strip lid holder 230, if access to the tube strip holders 212 is impeded. To this end, the tube strip lid holder 230 and other parts may be provided on one or more sliding racks 702.

The embodiment of FIG. 7 is operated to transfer specimens from samples that require retesting to one or more output plates 242. Since (at least in the case of HC2 testing) the percentage of samples requiring retesting can be very small, the retest candidates may be distributed among a large number of tube strip holders 212. As such, it may be helpful to provide a large number of tube strip holders 212 as compared to the number of output plates 242. In the shown example, twenty-four tube strip holders (up to 576 individual samples) are provided with as single 96-well output plate 242, but other arrangements may be used, as desired.

The embodiment of FIG. 7 is operated by providing the processing module 700 with an electronic record identifying which tubes on which tube strip holders 212 contain samples to be retested. The record may be linked to a barcode on each tube strip holder 212, or provided otherwise. As the sliding racks 250 are installed, a bar code reader (not shown) may read a barcode on each tube strip holder 212, providing the processing module 700 with sufficient information to identify the exact location of each sample requiring retesting. After the sliding rack 250 is installed, the processing module 700 transfers a specimen from each sample to be retested from the tube strip holder 212 to the output plate 242. To facilitate retesting a large number of samples, the processing module 700 may transfer samples from the tube strip holders 212 on the rightmost sliding rack 250, and progressively work left as each sliding rack 250 is completed. Using this method (or other methods in which each rack 250 is completely processed before moving to the next rack 250), the operator can remove sliding racks 250 that have completed processing, and replace them with unprocessed racks 250, even while the processing module continues to transfer samples from other racks 250 to the output plate 242. A suitable system of locks or indicator lights may be provided to indicate which racks 250 are complete and ready for replacement, and to prevent errant removable of racks 250 that have not been processed. Of course, the foregoing arrangement may be modified. For example, the individual tube strip holders 212 may be removed after all samples to be retested have been transferred to the output plate 242, and replaced with another tube strip holder 212.

Other variations on the layout and function of a processing module will be readily apparent from the foregoing disclosure. For example, the embodiment of FIG. 6 can be modified to start with tube strip holders 212 holding tube strips 210 that have been processed up through step 308 of FIG. 3, and then stored or briefly retained for later processing. In this modification, the empty lanes 202 may contain reagent racks 233 to provide the necessary reagents to complete the process of FIG. 3. Also in this modification, step 306 (dispensing SCB) may be performed as the first step, and step 308 would be omitted as being moot.

It will also be appreciated that any suitable sample tracking system may be used with embodiments of a processing module. For example, barcodes may be used to identify individual samples, associate groups of samples with particular tube strips 210, tube strip holders 212, and output plates 242, and so on. Processing errors and other information may be immediately associated with an electronic record for each sample by reference to the barcode-related information. Suitable barcode readers may be used throughout the processing module to track progress and confirm identity and process integrity at periodic intervals or locations. Radio-frequency identification devices and other indicia may also be used in other embodiments.

Exemplary Sample Adequacy Modules

As noted above, it may be desirable to include a sample adequacy evaluation system in a processing module, particularly where processing a sample that lacks sufficient cells to provide a meaningful result might be expensive or risk reporting an erroneous test result. For example, a sample adequacy evaluation system may be desirable to detect the presence of a sufficient number of epithelial cells to conduct meaningful tests for HPV. Sample adequacy evaluators, such as nephelometers and turbidity meters, have been used in a variety of clinical settings, and devices that are compatible with automated processing may be used with embodiments of the processing modules described herein. It has also been found that sample adequacy, and a variety of other sample properties, can be determined using sound waves, and particularly ultrasonic sound waves.

An exemplary embodiment of an ultrasonic sample adequacy detector is shown in FIG. 8. The detector includes a receptacle 800 having an ultrasonic emitter or transducer 802 mounted to the bottom of the receptacle 800. The transducer 802 is oriented to direct ultrasonic waves in a vertical direction, and may comprise a conventional flat or focused transducer. Any suitable transducer, such as a conventional piezoelectric transducer, that is capable of transmitting and detecting an ultrasonic wave may be used. Piezoelectric transducers are available from a variety of sources, such as Olympus NDT of Center Valley, Pa. Exemplary equipment for use in this application may include a Panametrics 10 MHz 0.25 inch diameter element, with input provided through a programmable pulse generator and output fed through a programmable amplifier/filter and displayed on an oscilloscope.

The illustrated transducer 802 is mounted in a port through the bottom of the receptacle 800, but it may be located inside or below the receptacle 800, or the bottom of the receptacle 800 may form a part of the transducer itself. If necessary, the exact location of the transducer 802 may be adjusted to provide clearer or more focused signals. It will be understood that transducers are a combined ultrasonic transmitter and ultrasonic receiver, and the transducers described herein may be replaced by separate transmitters and receivers. For brevity, references herein to a transducer will be understood to include an alternative transmitter/receiver pair.

The receptacle 800 is shaped and sized to receive one or more varieties of sample vials 404. The embodiment of FIG. 8 receives a conventional flat-bottomed vial 804, such as a PreservCyt® vial. If the transducer 802 does not contact the bottom of the vial 804 sufficiently to reliably conduct ultrasonic waves, it may be necessary to include a coupling medium 806 to form an ultrasonic-transmitting pathway. The coupling medium 806 may comprise a viscous or fluid compound, such as grease or a liquid bath, or a solid compound, such as an elastomeric compound. Combinations of the two may be used as well. To help ensure a proper sound-transmitting path is formed, the tube 804 may be pressed into the coupling medium 804. For example, a robotic arm that places the tube 804 in the receptacle 800 may press the tube down into the coupling medium 806 with a slight force during the sample adequacy testing process, or a separate press or clamp may be provided to press the tube 804 into place.

The transducer 802 is configured to produce an audio (compressed waive) signal preferably at ultrasonic frequencies (above about 20,000 Hz). The expected scattering signal can be modified by altering the signal frequency. For example, frequencies having a wavelength (the reciprocal of the frequency) that is much larger than the cell size are expected to produce so-called Rayleigh scattering, and frequencies with a wavelength that is much smaller than the cell size should produce specular scattering. Frequencies with wavelengths that are closer to the cell size should produce intermediate scattering signals. For cells having a size of 60-100 micrometers, a wavelength of about 100 micrometers may be used to obtain intermediate scattering. Increasing wavelength could provide more diffuse Rayleigh scattering, but at the expense of overall intensity. Where the volume of the scattering media (cells) is less than about 20% of the total volume of the substance being tested, the intensity of the scattered signals is expected to be approximately linearly proportional to the scattering concentration. This is the case in testing typical epithelial cell concentrations in the context of HPV test protocols, which often have a cell concentration of 1,000 cells per milliliter of preservative fluid, or less.

Any suitable control equipment may be used to operate the transducer to transmit and detect signals. Suitable devices and software programs are readily available from transducer suppliers.

FIG. 9 shows an alternative embodiment, in which the an ultrasonic sample adequacy test receptacle 900 is configured to receive a tapered tube 904, but the remaining components are essentially the same as the embodiment of FIG. 8. Where a tapered tube 904 is processed, the ultrasonic transducer 902 may be connected to the tube 904 by a contoured coupling medium 906 that cups the end of the tube 904 to provide a larger contact area.

The sample adequacy test is performed by placing the tube 804 in the receptacle 800, activating the transducer 802 to transmit a source ultrasonic signal, and using the transducer 802 to detect the reflected ultrasonic signals ("backscatter"). (This description references the embodiment of FIG. 8, but it is equally applicable to the embodiment of FIG. 9 and other embodiments.) The ultrasonic signal may comprise a single event, but more preferably is a series of pulsed signal events to provide better sampling data. The signal travels vertically through the coupling medium 806 and the bottom of the tube 804, and into the liquid media 808 inside the tube 804. As the signal propagates upwards through the media 808, any significant changes in density will reflect a portion of the signal, and such reflected signals may be detected by the transducer 802. For example changes in density may be caused when the signal passes from one medium to another (e.g., passing from the coupling medium 806 to the tube 804 and from the tube 804 to the liquid 808), when the signal contacts a cell, or when the signal reaches the upper extent of the liquid 808 and passes into the air. If the density of the cells are similar to the density of the liquid 808, it may be necessary to modify the density of one or the other to help generate reflected signals. The backscatter is also a function of the relationship between the sound wavelength and the particle (cell) diameter and an optimum frequency can be selected to maximize the return. The transducer 802 detects these reflected backscatter signals, and they are recorded by a computer operating the transducer 802.

Figure 10:
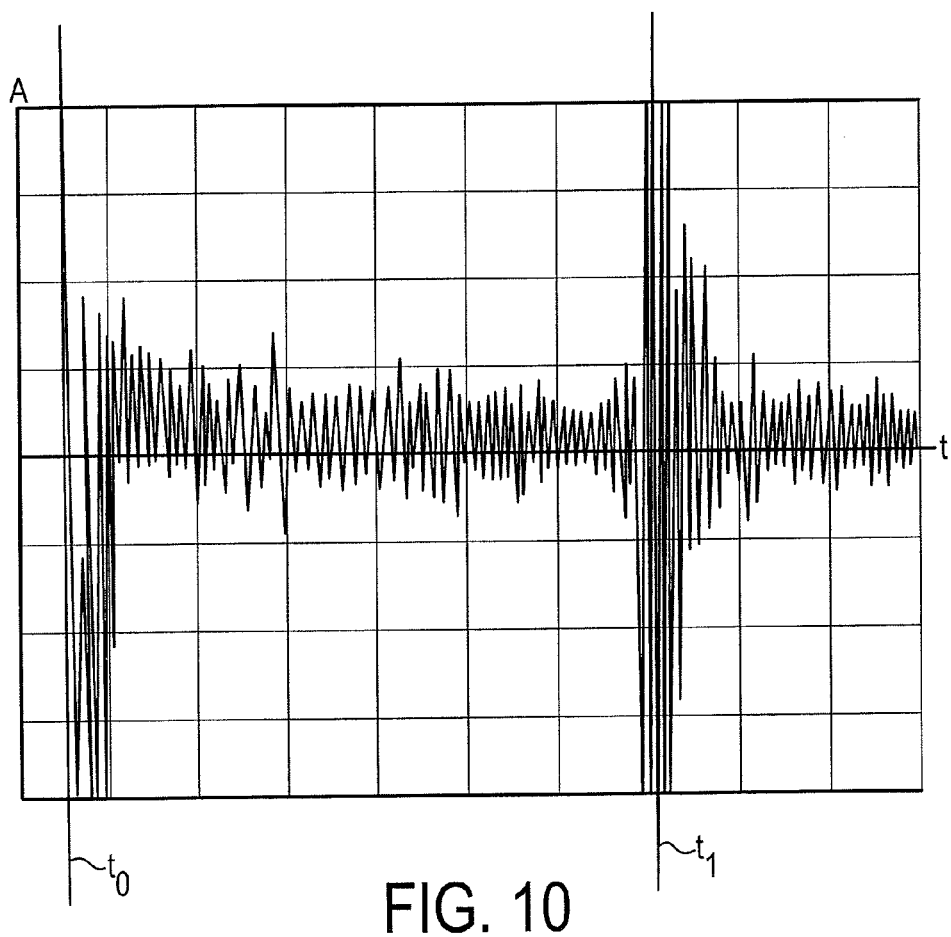
FIG. 10 is a schematic representation of a first ultrasonic backscatter signal.

A schematic representation of a backscatter signal is shown in FIG. 10, which is a plot of backscatter amplitude (A) versus time (t) for a single ultrasonic pulse. FIG. 10 shows the backscatter signal as it might appear. The transducer 802 begins recording at $t_0$, at which time the acoustic backscatter begins to reflect back to the transducer 802. Time $t_1$ represents the time at which the signal reflecting off the upper surface of the fluid reaches the transducer 802. The curve between $t_0$ and $t_1$ indicates the distribution of the amplitude of the backscatter signal. Repeated pulses can be overlaid over this curve to enhance sampling resolution. It is expected that this backscatter signal can be used to detect a variety of sample properties.

A first sample property that can be evaluated using the backscatter data is the liquid level. Typically, the last large backscatter signal will be generated as the ultrasonic signal reaches the meniscus of the liquid 808 in the tube 804 and propagates into the surrounding air. The signal rapidly degrades after it leaves the liquid 808, and little or none of the signal will reflect back into the liquid 808 to be detected by the transducer 802. The liquid level can be determined based on the total amount of time it takes for the backscatter signal to reach the transducer 802. For example, if $t_1$ is at or above a certain time value, then the liquid level may be considered a passing level. Such qualitative assessments can be calibrated to the particular kind of tube 804 and liquid media inside the tube, as well as other system properties, such as the type of coupling medium 806 and so on. Alternatively, the liquid level can be approximated numerically by considering the known dimensions of the different parts of the signal path (i.e., the coupling medium 806 and tube 804) and the speed of sound in these various parts of the path. If the speed of sound is known for all of the path elements (coupling medium 806, tube 804 and liquid 808), then the maximum signal reflection signal time can be used, along with the known dimensions, to calculate the depth of the liquid 808. The details of this calculation will be readily apparent to persons of ordinary skill in the art, and need not be discussed here.

If the ultrasonic test reveals that the liquid level (and hence volume) is insufficient to perform a meaningful test, the sample may be rejected and not subjected to further processing. Other variations on using the signal to evaluate the liquid level will be apparent to persons of ordinary skill in the art based on the present disclosure.

A second sample property that can be evaluated using the backscatter data is the cell concentration. Cells suspended in the liquid 808 will cause small backscatters at various times, depending on the height of the cell in the tube 804. Such backscattering typically appears (in high resolution plots and without smoothing), as grass-like noise between $t_0$ and $t_1$. As the cell concentration increases, the amplitude of this noise increases. If the cells are generally equally distributed throughout the liquid 808, the noise will be generally equally distributed throughout the backscatter plot. A schematic example of this kind of even distribution is shown in FIG. 10. The adequacy of the sample or an estimate of cellular concentration can be determined by comparing the properties (e.g., average amplitude) of the backscatter to known examples, and a plot of the same can be readily developed using empirical testing.

Figure 11:
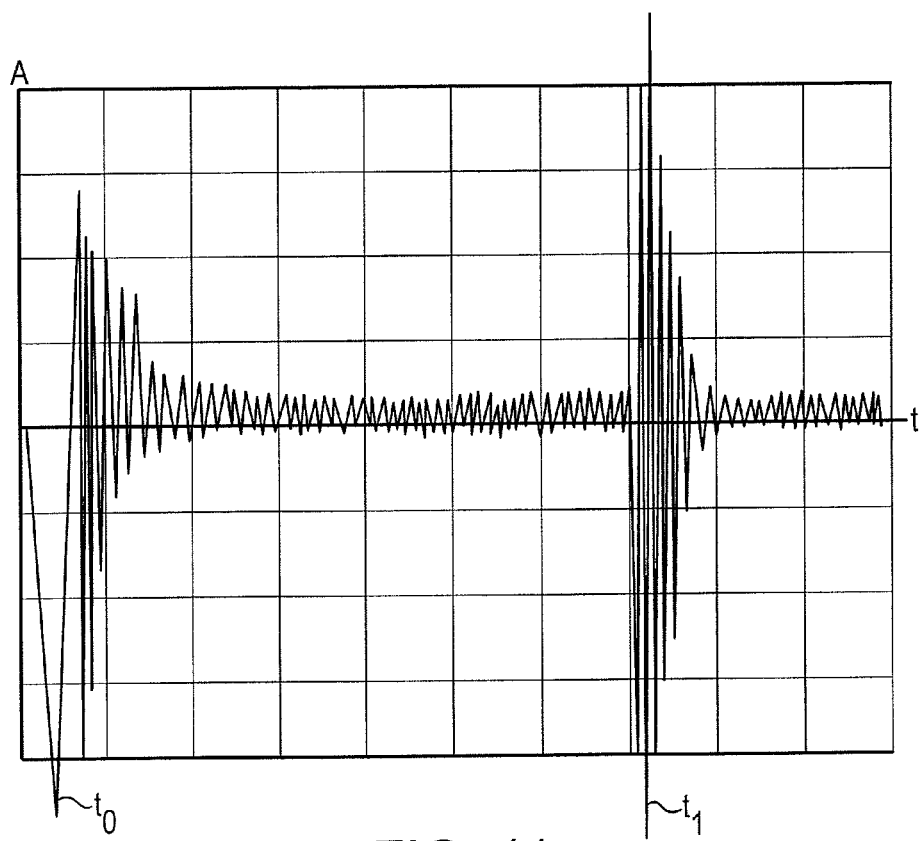
FIG. 11 is a schematic representation of a second ultrasonic backscatter signal.

In contrast, FIG. 11 shows a schematic representation of a sample having little or no cellular content, as indicated by the lack of scattered reflections before the signal reaches the meniscus at $t_1$. The sample generating the plot in FIG. 11 may have insufficient cellular content to be processed without risking a false negative result. In situations in which useful information about the cell concentration can be determined by evaluating the settling rate of the cells, the transducer can be operated multiple times (e.g., several times per second) to yield comparative backscatter data to indicate how rapidly the cells settle after being suspended in the liquid 808.

Figure 12:
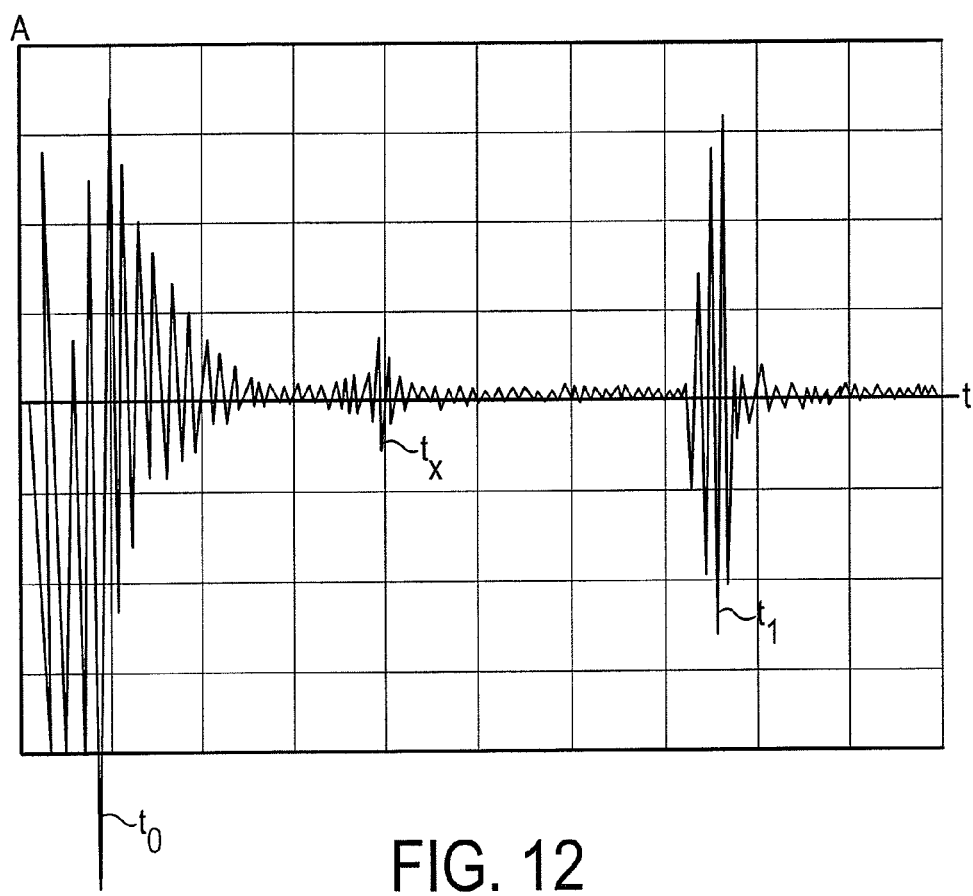
FIG. 12 is a schematic representation of a third ultrasonic backscatter signal.

A third sample property that may be evaluated from the backscatter data is the presence of foreign objects. Biological samples and other samples are often collected and placed into sample tubes using swabs, brushes, sponges, and other collection implements 810. In some cases, the implement or a portion of the collection implement may remain in the sample tube. A collision between the collection implement and a pipette or other processing equipment can cause damage, and may result in a spill or other contamination. Also, the sample may include large masses of material, such as large clots or volumes of blood, that may interfere with regular processing operations. Collection implements, large clots, and other foreign objects may appear on the backscatter data as significant reflections that do not follow the normal patterns of random scattering from distributed cells or reflection from the liquid meniscus. In addition, a foreign object is likely to be stationary, as opposed to the moving mass of cells, and its reflected signal should likewise remain stationary. FIG. 12 provides a schematic example of backscatter data that might be generated as the signal reflects off a collection implement 810, such as the one shown in FIG. 8. Here, the implement 810 causes a distinct peak at $t_x$ in the reflection amplitude at a relatively discrete location along the curve, indicating a possible foreign object.

The backscatter data may be processed in one or more ways to evaluate cell concentration, sample volume, and the presence of foreign objects. It will be appreciated that any number of algorithms or logical process may be used, ranging from simple point sampling to more complex waveform morphology interpretation using frequency spectrum analysis and the like. For example, Fourier analysis may be used to extract frequency information from the raw data to identify time-domain information such as the time of flight to the last large reflection to indicate the liquid depth. Another process may be to compare successive reflection patterns to identify reflections from stationary objects (e.g., a sample brush) that might be overlaid by reflections from moving cell, and remove such signals to enhance the perception of the reflections from the cells. Such algorithms are generally known in the art, and examples of processing methods are provided in U.S. Pat. Nos. 6,796,195; 7,523,649; 7,543,480; 7,739,911; and 7,838,296, which are incorporated herein by reference. Other variations will be apparent in view of the present disclosure. Such analyses can be used to determine numerical properties (e.g., volume or cell count), or to determine whether the samples fall without predetermined parameters (e.g., pass/fail analysis). Suitable parameters may be developed using routine empirical testing based on control samples, as commonly done in the art.

It has been found in practice, that ultrasonic sample adequacy systems can successfully identify fluid volume and the presence of foreign objects, but in some cases the cells themselves may remain essentially transparent to the ultrasonic signals. Even in this case the system still can provide a significant benefit. If it is necessary to also detect cell concentration, measures may be taken to differentiate the cells from their environment, such as by changing the composition of the fluid media, altering the processing temperature, and so on.

As will be apparent from the foregoing, an ultrasonic sample adequacy system, such as the examples described herein, can provide an advantage by evaluating multiple sample properties with a single, rapid test. Also, unlike nephelometer and turbidity meter equipment, ultrasonic testing does not require an optically clear tube. While the foregoing three sample properties may be determined essentially simultaneously in one embodiment, other embodiments may evaluate the sample for fewer or other properties. For example, in another embodiment, the ultrasonic sample adequacy system may be used to determine whether a pellet is present in a sample tube. In such a system, the backscatter data might be evaluated to identify a distinct scattering pattern at a location below the meniscus.

To provide greater versatility, the ultrasonic sample adequacy detector may be configured to receive tubes having a variety of shapes and sizes. If necessary, adaptors may be included to fit smaller tubes to larger receptacles. Also, the coupling medium may be generally flat to contact flat-bottomed tubes, but have a dimpled recess to contact tapered tubes. Still further, the detector may have multiple receptacles to facilitate simultaneous testing of a number of tubes, such as all of the tubes in an entire tube strip 210 or all of the tubes in an entire tube strip holder 212. In one embodiment, a processing module, such as processing module 400, may have two sample adequacy test stations: one for testing one kind of tube (e.g., a PreservCyt® tube), and another for testing another kind of tube (e.g., a SurePath™ secondary conical tube). The user may swap out stations depending on the type of tube being tested, or the processing module may direct the tubes to the appropriate test station automatically based on reading identifying marks on the tubes (e.g., barcodes and associated tube type data) or by following instructions provided by a user. Other variations will be apparent to persons of ordinary skill in the art in view of the present disclosure.

Depending on when the sample adequacy test is performed, it may be necessary to resuspend the cells in the sample prior to or during adequacy testing. For example, in the process described above with reference to FIG. 5, if the sample adequacy is determined shortly after step 506 (hydraulically mixing the sample), no further mixing may be required. In contrast, if the sample adequacy is measured before the tubes 404 are even decapped, such as before the process of FIG. 5 begins, mixing may be necessary. Testing prior to decapping may be favorable to forego the need to decap and expose the sample if testing would not be productive. If mixing is required, a conventional mixer may be used prior to placing the tube in the adequacy detector. Alternatively, the adequacy detector may be mounted on a platform that operates as a mixer, so that the adequacy detector receptacle can operate as a mixing device to resuspend the cells. Other variations will be apparent to persons of ordinary skill in the art in view of the present disclosure.

Exemplary Decanting Systems

The foregoing examples of processing modules also may include one or more devices for removing supernatant from a pelletized sample. Such a device may be configured to match a manual decanting process's mechanics, results, or both. One example of a device for removing supernatant is a decanting system that rotates the tubes to pour out the supernatant. A decanting system may decant the individual tubes, but more preferably simultaneously decants supernatant from all of the samples in a tube strip 210. An exemplary embodiment of a decanting system is now described with reference to the examples illustrated in FIG. 13A-16B.

In general terms, the decanting system 1300 comprises one or more decanting grippers 1302 that cooperate to rotate a tube strip 210 to decant the supernatant. In the shown exemplary embodiment, the tube strip 210 is rotated by moving the decanting grippers 1302 vertically along a gear rack 1304. It may be desirable to mount the gear rack 1304 and/or decanting grippers 1302 on resilient mounts to absorb impact that might occur as the decanting grippers 1302 move into engagement with the gear rack 1304. This shock absorption may be particularly helpful where the automated drive equipment is sensitive to impacts, or the parts are liable to be damaged or fatigued by repeated impact loads. Any form of flexible mount may be used. For example, the gear rack 1304 may be mounted on a base 1310 by pins 1312, with a slot 1314 surrounding one pin 1312 to allow some rotation about the other pin 1312. A spring 1316 is provided to bias the gear rack 1304 into the unflexed position. As another alternative, the gear rack 1304 may be cantilever mounted in a pocket formed of resilient material that allows some movement between the gear rack 1304 and the platform upon which they are mounted, or other arrangements may be used.

Figure 13A:
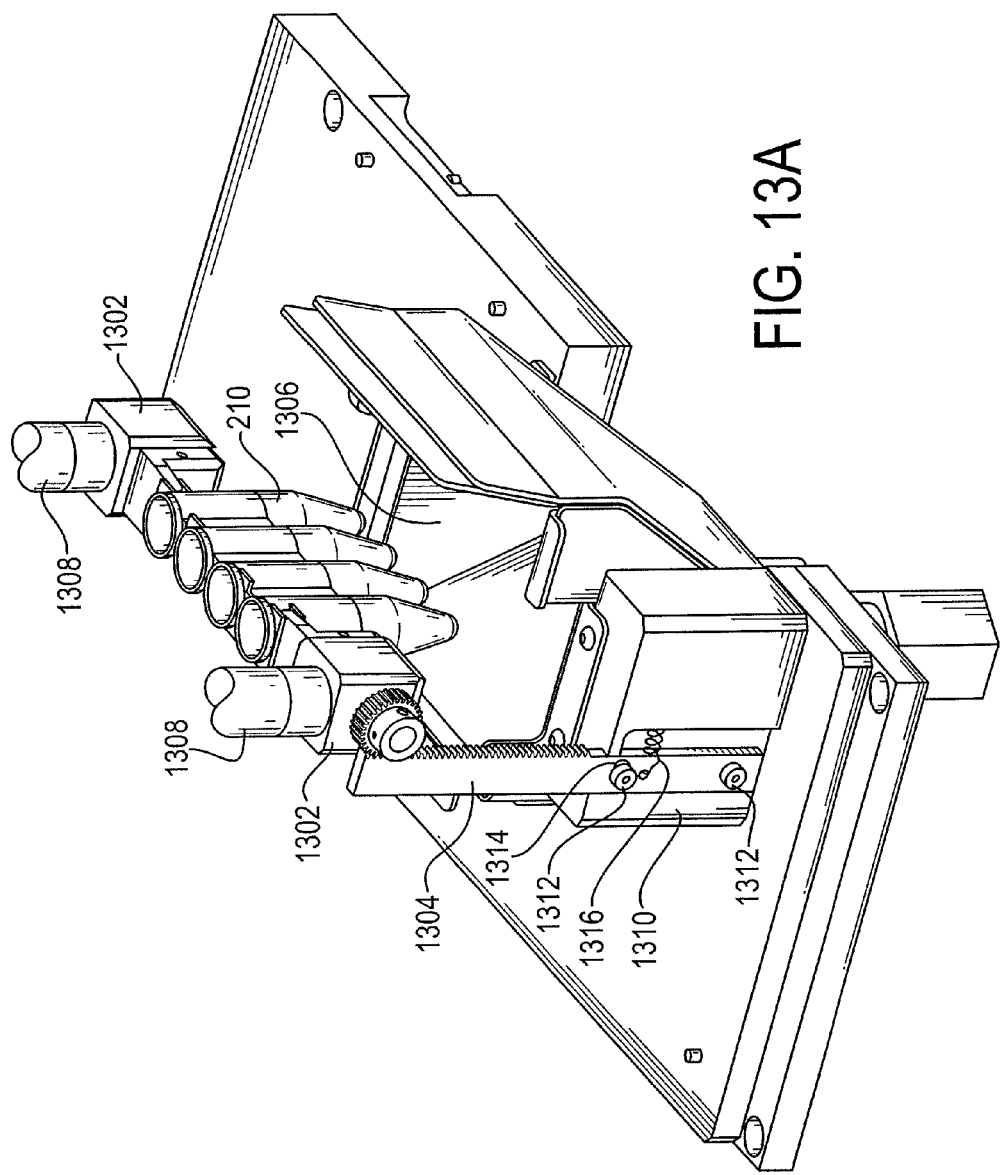
FIG. 13A illustrates an exemplary decanting system shown in the ready state prior to decanting.
Figure 13B:
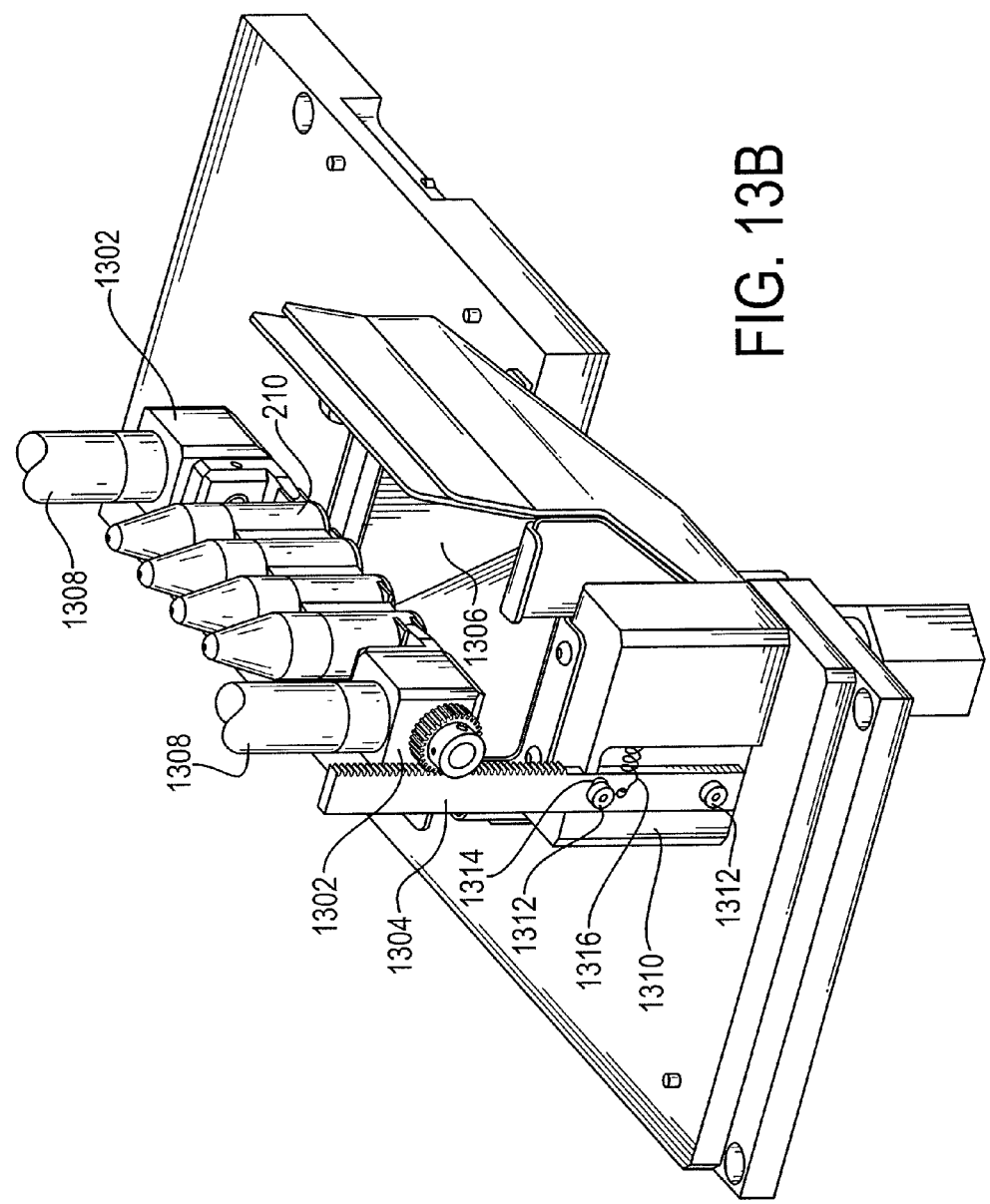
FIG. 13B illustrates an exemplary decanting system shown in the decanting position.

FIG. 13A illustrates the decanting system 1300 in the ready state prior to decanting. FIG. 13B illustrates the decanting system in the decanting position, in which the decanting grippers 1302 have been moved down along the gear rack 1304 to rotate the tube strip 210 to allow the liquid contents to flow out by gravity. An opening 1306 leading to a decant waste well 226 is located below the tube strip 210 to receive the decanted fluids. The decant waste well 226 may include suitable receptacles, pumps, hoses, or the like to remove and contain the decanted liquid.

The decanting grippers 1302 may be operated as a separate mechanism within the processing module, such as a dedicated robotic arm system. However, in a more preferred embodiment the decanting grippers 1302 are operated by pipette channels 1308 or other transport mechanisms already in the processing module. In addition to holding the tube strip 210 during decanting, the decanting grippers 1302 also may be configured to retrieve the tube strip 210 from a tube strip holder 212 or other holder before decanting, and return it to the holder after decanting.

Figure 14:
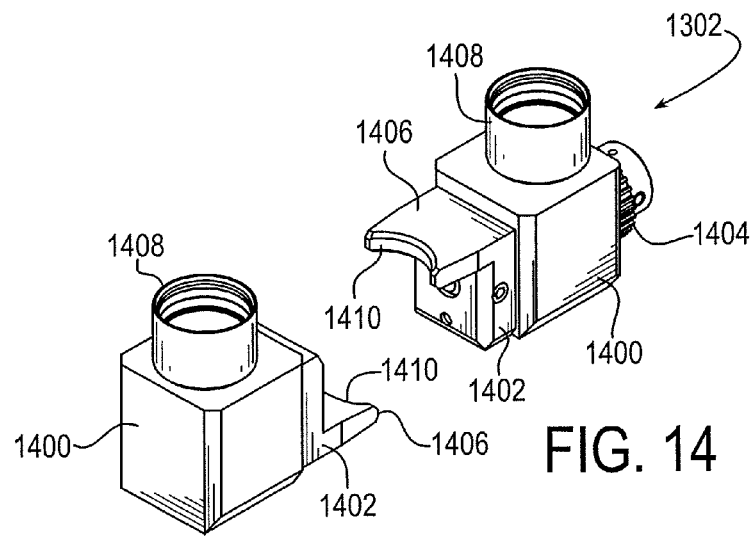
FIG. 14 illustrates a pair of exemplary decanting grippers, with one shown in the upright position and the other in the inverted position.
Figure 15:
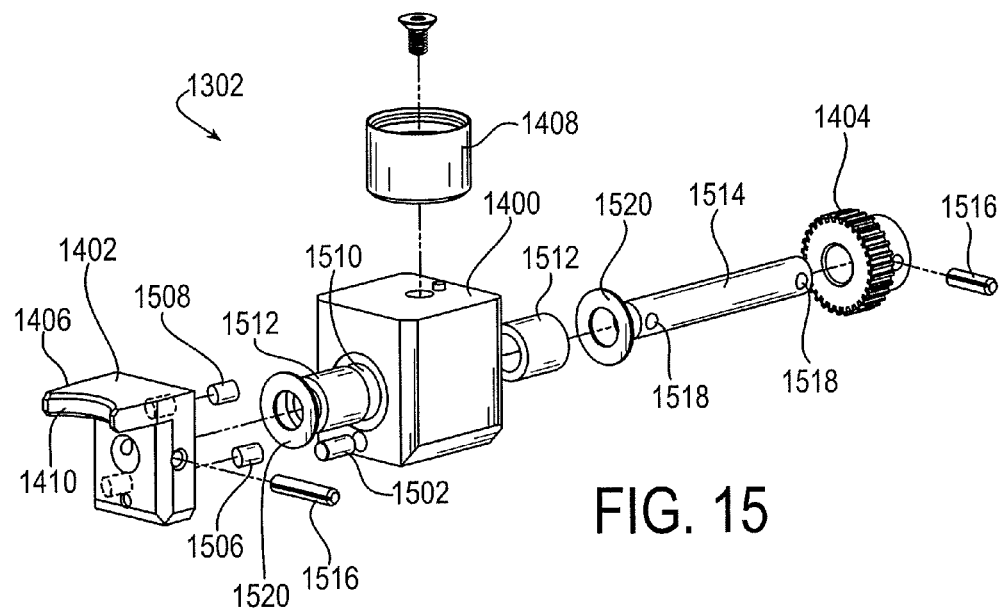
FIG. 15 is an exploded view of an exemplary decanting gripper of FIG. 14.

As shown in FIGS. 14 and 15, each decanting gripper 1302 has a base 1400 and a rotatable arm 1402. Any suitable arrangement of bearings, axles and the like may be used to connect each arm 1402 to the respective base 1400, to permit relative rotation through a limited or unlimited range of motion. One arm 1402 has a gear 1404, which may be a complete gear (i.e., a gear that has teeth around its entire perimeter, to allow full 360° motion) or a partial gear (i.e., a set of teeth that does not extend around the entire perimeter, to provide limited rotation). Each arm 1402 also includes a tube holder 1406 that is adapted to hold the tube strip 210 throughout the operating range of rotation. For illustration, FIG. 14 shows the tube holder 1406 on the left-hand decanting gripper 1302 in the inverted orientation, and the tube holder 1406 on the right-hand decanting gripper 1302 in the upright orientation.

Each decanting gripper 1302 also may include an attachment interface 1408 that can be engaged by a robotic pipettor channel or other mechanism. The attachment interface 1408 may comprise, for example, a cup-like receptacle having ribs or grooves on its inner wall that snap into or are locked into engagement with a pipettor channel's outer surface. Such attachment interfaces are known in the art, and available commercially from companies such as Hamilton Robotics of Reno, Nev. (e.g., the Hamilton CO-RE system).

The gear 1404 is selected to engage the gear rack 1304 to rotate the arms 1402 as the decanting grippers 1302 are moved vertically along the gear racks 1304. The shown embodiment uses conventional gear teeth, but these may be replaced by other kinds of teeth or surfaces. For example, the gear rack 1304 may comprise a simple metal post, and the gear 1404 may comprise a rubber traction wheel that can frictionally grip the post to provide the necessary rotational movement. Also, the gear 1404 may be directly mounted to the arm 1404 to directly rotate it, as shown in FIG. 15, or the gear 1404 may rotate the arm 1404 through one or more intermediate gears.

The decanting grippers 1302 also may include one or more features to resiliently hold the arm 1402 in one or more positions relative to the base 1400 when the decanting grippers 1302 are not engaged with the gear rack 1304. This may be desirable, for example, to hold the tube strip 210 upright before and after it is decanted, and to prevent the tube strip 210 from swinging during transport to and from the decanting system 1300. In one embodiment, a suitable retaining force may be provided by simple friction between the arm 1402 and the base 1400, but as the device wears is may be necessary to adjust the friction level to maintain the desired retention force. In another more preferred embodiment, a resilient holding force may be generated by magnets or other devices.

An example of a magnetic holding system is shown in FIG. 15. In this exemplary embodiment, the base 1400 may include a magnet 1502 that is retained in a bore 1504 in the base 1400, and the arm 1402 may include one or more magnets 1506, 1508 that face the base magnet 1502 at respective predetermined arm orientations. The magnets magnetically retain the arm 1402 with respect to the base 1400 at the predetermined arm orientations. The magnets should be oriented to establish the desired magnetic attraction or repulsion forces to provide the desired retaining force. The embodiment of FIG. 15 shows the arm 1402 having two magnets 1506 and 1508, which are located to hold the arm 1402 in the upright and inverted positions by magnetic attraction with the magnet 1502 in the base 1400. If desired, one of the magnets may be removed to provide a magnetic hold in only one orientation (e.g., the upright orientation), more magnets may be added, the magnets may be replaced by materials attracted to magnets, or both magnets may be removed if no magnetic holding is desired.

The arrangement of magnets in FIG. 15 is exemplary. It will be understood that other locations and numbers of magnets may be used in other embodiments. Furthermore, the magnets on either the arm 1402 or the base 1400 may be replaced by a ferromagnetic material (e.g., iron) or paramagnetic material that is attracted to the magnet(s) on the other part. For simplicity, the term "magnet" is intended to cover any kind of magnetic material or electromagnet, as well as any material (e.g., an iron slug) that is attracted to magnetic forces. Any combination of the foregoing may be used to provide a magnetic holding force between the arm 1402 and the base 1400.

It has been found that magnets are particularly useful to hold the tube strip 210 vertically before and after decanting, but allow some minor rotation as the decanting grippers 1302 are moved into initial engagement with the gear racks 1304. This rotation can account for any mismatch between the teeth on the gear 1404 and the rack 1304. Preferably, the magnets permit a mismatch of up to about one half of the gear pitch, so that the gear 1404 can rotate to engage the gear rack 1304 even if the teeth contact tip-to-tip as the decanting grippers 1302 are moved into initial engagement with the gear rack 1304.

Other embodiments may use other mechanisms to hold or bias the arm 1402 into predetermined orientations with respect to the base 1400. For example, a return spring may be used to urge the arm 1404 towards the upright position, but allow some rotation to permit initial engagement between the gear 1404 and gear rack 1304. Travel stops also may be used to prevent the arm 1402 from rotating past desired orientations.

FIG. 15 also shows various other exemplary details of a decanting gripper 1302 construction. In this case, the base 1400 has a bore 1510 that receives a pair of bushings 1512, and a shaft 1514 is rotatably mounted in the bushings 1512. The gear 1404 and arm 1402 are fixed to the shaft 1514 by respective pin 1516 that are pressed into respective bores 1518 in the shaft. The gear 1404 and arm 1402 are spaced from the base 1400 by washers 1520, to provide a low-friction contact at this location.

In use, the decanting grippers 1302 may be stored in a gripper parking location 228 until decanting is required. In preparation for decanting, a decanting grippers 1302 are mounted to respective pipette channels 1308 by moving the pipette channels 1308 into the grippers' respective attachment interfaces 1408. The pipette channels 1308 may lock into the attachment interfaces 1408 by snap fitment, mechanical locks, magnetic locks, or the like. Next, the pipette channels 1308 are operated to grasp a tube strip 210 with the decanting grippers 1302, and carry the tube strip 210 to a location adjacent the gear rack 1304. The pipette channels 1308 then move to engage the decanting gripper gear 1404 with the gear racks 1304. After engagement, pipette channels 1308 are moved downward to rotate and decant the tube strip 210 via driving engagement between the gear 1404 and the gear rack 1304. During decanting, the tube strip 210 rotates about a decanting axis defined by the rotation centers of the gear 1404. After all the tubes in the tube strip 210 are sufficiently decanted, the pipette channels 1308 move up or down to rotate the tube strip 210 to the upright position via driving engagement between the gear 1404 and the gear racks 1304. Alternatively, the decanting grippers 1302 may move out of engagement with the gear rack 1304 after decanting is complete, and some other mechanism or motion (e.g., contacting the tubes strips 210 with a fixed object) may be used to return the tube strip 210 to the upright position.

The operating parameters of the decanting process may be modified to provide the desired decanting properties or results. Parameters that may be modified include the rotation rate to invert the tube strip 210, the rotation rate to return the tube strip 210 to the upright position, the decanting angle at which the tube strip 210 is rotated in the inverted position, and the amount of time spent at the decanting angle. Complex decanting motions, such as stopping at various angles for various times, may also be used. Other factors that may be considered are the composition of the supernatant (e.g., buffers high in alcohol may sheet and not flow rapidly), the pellet properties (e.g., likelihood of sliding down the tube wall), the composition of the tubes (wetting angle and the like can affect decanting), the diameter and length of the tubes, and so on.

In an embodiment in which the decanting system 1300 is used to simulate manual decanting in the HC2 protocol, samples in a PreservCyt® buffer may be decanted by rotating the tube strip 210 to an angle of 150° from vertical, holding for approximately one second (or five seconds or less, in another exemplary embodiment), and returning the tube strip to vertical. To decant samples in a SurePath™ buffer, the tube strip 210 may be rotated through 360° with a pause of approximately 0.5 to 1 second at 210° from vertical. Other decanting processes may be used to simulate the performance or results of the HC2 manual decanting protocol, or to simulate the performance or results of other protocols.

In an alternative embodiment, both decanting grippers 1302 may have gears 1404, two engage two respective gear racks 1304. However, it has been found that embodiments having multiple gear racks 1304, may require particular attention to ensure that the gear racks 1304 simultaneously engage the gears 1404 on the two decanting grippers 1302. If both gears 1404 and both gear racks 1304 have meshing teeth, then any misalignment present at one gear/rack pair that is not also present at the other gear/rack pair can cause a problem with engagement. For example, if one gear 1404 must rotate to properly engage its respective gear rack 1304, but the other gear 1404 is aligned to mesh with its gear rack 1304 without rotating, it may be necessary to twist the tube strip to properly mesh both gears at the same time. In extreme cases, this kind of mismatch may prevent proper tube strip decanting. To prevent this issue, a one gear rack 1304 may have teeth, and the other gear rack 1304 may lack teeth. In this embodiment, only the toothed gear rack 1304 will mesh with its respective gear 1404, and the gear 1404 on the other decanting gripper 1302 will simply slide or roll along the toothless gear rack 1304. In this case, the gear 1404 on the decanting gripper 1302 that contacts the toothless gear rack 1304 may be replaced by a simple wheel.

Embodiments using a rack-and-pinion gear system, as described above, have been found to provide simple and accurate decanting, while avoiding the need for adding expensive additional equipment to the processing module. Nevertheless, it will be appreciated that, in other embodiments, any other mechanism may be used to rotate and decant the tube strip 210. For example, an electric motor (e.g., a servo motor) may be mounted on one or both of the decanting grippers 1302 to rotate the tube strip 210. In the shown embodiment, two decanting grippers 1302 are provided, with one decanting gripper 1302 holding each end of the tube strip 210, but it will also be understood that any other suitable arrangement of one or more decanting grippers 1302 may be used. For example, other embodiments may use a single decanting gripper located at the end or somewhere along the span of the tube strip 210.

Figure 16A:
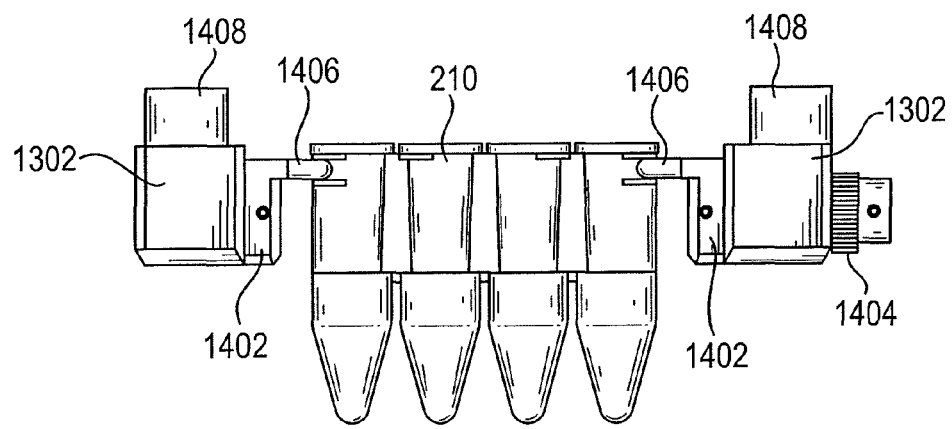
FIG. 16A illustrates an exemplary tube strip being held in an upright position by the decanting grippers of FIG. 14.
Figure 16B:
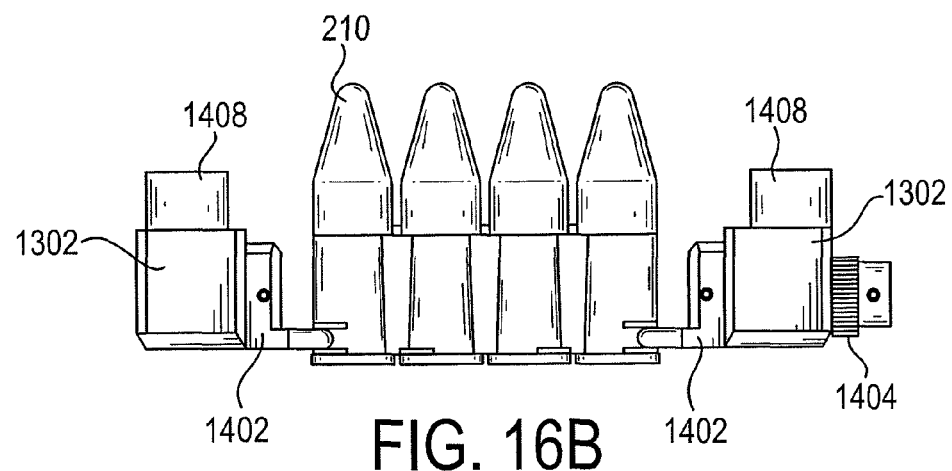
FIG. 16B illustrates an exemplary tube strip being held in an inverted position by the decanting grippers of FIG. 14.

As noted above, the decanting grippers 1302 hold the tube strip 210 throughout the range of rotation during the decanting process. FIGS. 16A and 16B illustrate the decanting grippers 1302 holding a tube strip 210 in the upright and inverted positions. The inverted position of FIG. 16B is fully inverted (i.e., 180° from upright), but the inverted position used during decanting may instead be at a lesser range of travel (e.g., 160° from upright).

Figure 17:
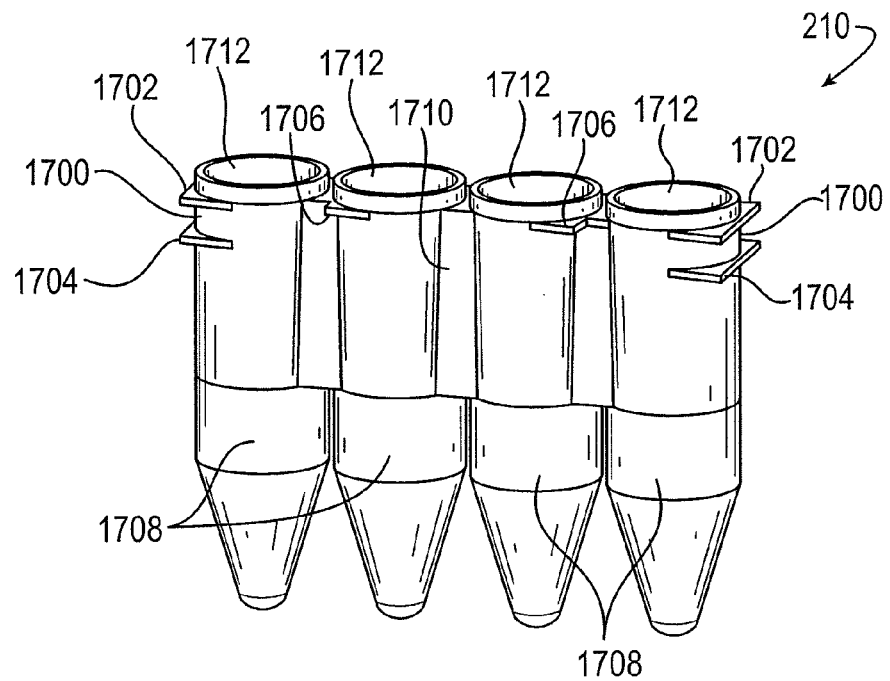
FIG. 17 illustrates an exemplary embodiment of a tube strip.

The tube holders 1406 and tube strip 210 may have any suitable arrangement of interacting features to provide the necessary grip to obtain the desired range of travel. In the exemplary embodiment of FIG. 17, the tube holders 1406 engage channels 1700 located at each end of the tube strip 210. Each channel 1700 may be formed between an upper rib 1702 and a lower rib 1704, but other structures may be used to form the channels 1700. The tube holders 1406 are shaped to fit in the channels 1700, and generally conform with the shapes of the channels 1700 to prevent shifting or other unregulated movement as the tube strip 210 is inverted. In this case, the tube holders 1406 have semicircular cutouts 1410 that match the semicircular inner wall of each channel 1700, but other shapes may be used in other embodiments.

While it is not required for the tube holders 1406 to hold the ends of the tube strip 210, doing so is expected to provide a convenient arrangement in which the decanting grippers 1302 do not interfere with the tube strip's path of rotation. However, it may not be possible to conveniently access channels 1700 that are located at the ends of the tube strip 210 when the tube strips 210 are placed in an end-to-end arrangement, such as when they are mounted on a tube strip rack 208 with little or no gap between adjacent tube strips 210. In this situation, it may be desirable to provide additional features on the tube strip 210 to allow manipulation if the tube strips 210 when the channels 1700 are blocked. For example, the tube strip 210 may include inboard tabs 1706 by which the tube strip 210 may be lifted and manipulated.

Figure 18:
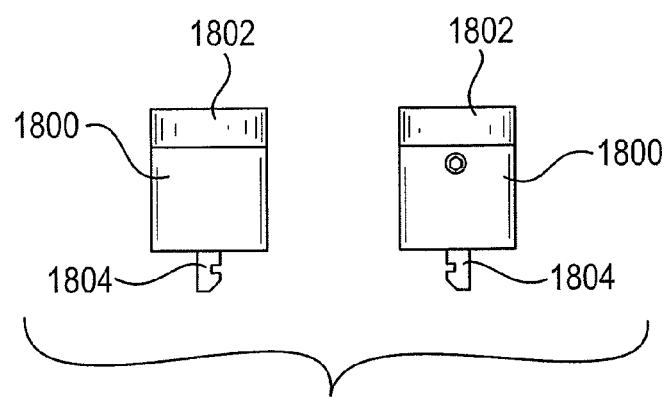
FIG. 18 illustrates a pair of exemplary transport grippers.
Figure 19:
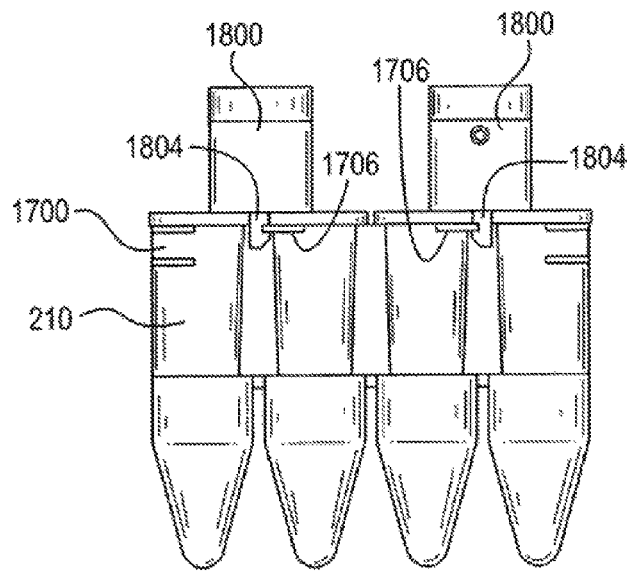
FIG. 19 illustrates the transport grippers of FIG. 18 holding the tube strip of FIG. 17.

FIG. 18 illustrates an example of transport grippers 1800 that may be used to grasp the inboard tabs 1706 to lift and move the tube strip 210. Each transport gripper 1800 includes an attachment interface 1802, such as described above, that engages with a pipettor channel or other movable mechanism, and one or more hooks 1804 shaped and sized to wrap around respective inboard tabs 1706. In the shown embodiment, each transport gripper 1800 has two hooks 1804 that straddle the top of the tube strip 210 and hold respective inboard tabs 1706 on either side of the tube strip 210. As shown in FIG. 19, the hooks 1804 on one transport gripper 1800 may face towards or away from the hooks 1804 on the other transport gripper 1800, so that the tube 210 cannot slide off the hooks 1804 during transport.

The transport gripper 1800 may be stored in a suitable gripper parking location 228 when they are not mounted for use. In other embodiments, the transport grippers 1800 may be replaced by other mechanisms, and may be provided as a separate robotic mechanism that is dedicated to transporting the tube strips 210.

The exemplary tube strip 210 may be modified in other ways to facilitate transport and decanting. For example, it will be readily appreciated that the foregoing channels 1700 may be placed on the tube holders 1406, and the tube strip 210 may have protrusions that fit into the channels. Similarly, the inboard tabs 1706 may be replaced with cavities into which the hooks 1804 fit. The channels 1700, tabs 1706, and corresponding features also may be replaced by other structures that facilitate lifting, moving and rotating the tube strip 210. For example, the tabs 1706 may be omitted and replaced with an attachment interface, such as those described above, that mates to a pipettor channel. These and other variations will be apparent to persons of ordinary skill in the art in view of the present disclosure.

Referring back to FIG. 17, other features of the exemplary tube strip 210 are described. The tube strip 210 is used to hold and move the samples, and may be the primary device for holding the samples generally throughout a processing module. The tube strips 210 may be made of any material that is suitable for the various processes, which may include transport, sample adequacy detection, mixing, centrifuging, incubating, decanting, chilling (for storage, if necessary), and other processes. In an exemplary embodiment, the tube strip 210 may be formed from a natural polypropylene homopolymer, which can be shaped to handle all of the required loads, and is thermally stable. Another suitable material may be a clarified random polypropylene copolymer, such as 5112C3 available from Pinnacle Polymers of Garyville, La.

The tube strips 210 may have any number or arrangement of individual tubes 1708. In this case, there are four tubes 1708, which conveniently matches the number of pipettors on a typical robotic four-channel pipettor system having variable spacing between adjacent channels. Such pipetting systems are available, for example, from Hamilton Robotics or Reno, Nev. Each individual tube 1708 may have any suitable shape, such as a conical bottom joined to a cylindrical sidewall. It will be understood that the cylindrical sidewall may not be perfectly cylindrical, and preferably has a slight conical shape (often referred to as a "draft angle") to facilitate a plastic molding process. For example, the cylindrical sidewall may have a 1° conical angle (i.e., the angle of the wall measured relative to the center axis of the tube 1708). The tubes 1708 are joined by a common central structure 1710 on which the channels 1700 and inboard tabs 1706 are formed. The entire tube strip 210 may be molded as a single part or assembled from various pieces.

The tubes 1708 may be constructed to help correlate the automated process with existing processing protocols. For example, where the automated process is intended to correlate to a manual HC2 protocol, the tubes' material and geometry (e.g., diameter and cone angle) may match tubes used in manual HC2 processing. Matching the material (e.g., using a natural polypropylene homopolymer) replicates the wetting and contact angle properties of such tubes, which may be helpful to correlate the automated decanting process with the manual decanting process. The diameter of the cylinder and shape of the conical bottom also may match conventional HC2 centrifuging tubes to produce known pellet formation and retention qualities during centrifuging. For example, it has been found that using tubes 1708 with the same material and cone geometry a conventional HC2 centrifuge tube provides suitable centrifuging and decanting results. Some modifications to the conventional tube shape may be made. For example, the decanting results may be improved by decreasing the height of the cylindrical sidewalls of the tubes in the tube strip 210, as compared to tubes used in a manual process, to permit fluid to decant more rapidly and reduce the likelihood of slinging fluid out of the tube in an uncontrolled manner. For example, the tubes in the tube strip may have an inner diameter of about 14.7 millimeters, a cone angle of about 30°, and a hemispherical tip having a radius of about 2.2 millimeters, which are all similar to conventional HC2 centrifuging tube dimensions, but an overall height of only about 58.2 millimeters, which is significantly shorter than a conventional HC2 centrifuging tube.

While the illustrated tube strip 210 is constructed with a material and shape to match an existing manual HC2 protocol, this is not necessary in all embodiments of tube strips 210 that are used to perform HC2 protocols. Deviations that do not affect the pellet formation results may be implemented as desired. Also, where the process is being performed is not a HC2 protocol, other constructions for the tubes 1708 may be used to conform with tube structures used in other protocols. It will also be appreciated that the shapes of the tubes may not correlated to other protocols, and may instead be designed to provide the results necessary for the particular application.

The tubes 210 preferably are arranged in a single row that extends linearly between the channels 1700, so that the tube strip axis (the direction in which the single row of tubes 1708 extends) is generally parallel with the decanting axis. The use of a single row of tubes 1708 with the tubes 1708 arranged along the decanting axis may be preferred over two-dimensional arrays of tubes or other orientations, because this arrangement helps reduce the possibility of one tube 1708 pouring into another tube 1708 during decanting. The lips 1712 of the tubes 1708 preferably are even with one another, and may be located at or near the decanting axis. Such placement may better simulate a manual decanting motion and avoid fluid slinging out of the tubes by centripetal force caused by the rotation. However, some offset between the decanting axis and the lips 1712 or the centerline of the row of tubes 1708 may be provided, if desired, to potentially benefit the decanting results.

Exemplary Blotting Systems

After decanting, it may be desirable to blot the tube strip 210 to help remove supernatant in the tubes, or to remove supernatant that might be clinging to the lips of the tubes. An example of a blotting system 2000 is shown in FIGS. 20-27C. The blotting system 2000 generally comprises a blotting sheet supply 2002, a disposal arm 2004, and a waste chute

2006. As shown here, the blotting system 2000 is integral with a decanting station 222 having a decant waste well 226 and a retainer 224 to hold a strip holder 212. The decanting station 222 also may have a gripper parking station 228 that holds decanting grippers 1302 and transport grippers 1800 when they are not in use. While these parts are conveniently integrated into a single unit, they may be provided as separate assemblies or remotely from one another. Where the blotting system 2000 is adjacent a decant waste well 226, the blotting system 2000 also may include a drip tray 2008 spanning the distance from the decant waste well 226 to the blotting sheet supply 2002 to catch any dripping liquid and convey such liquid to the decant waste well 226.

In general terms, the blotting system 2000 operates by contacting the lips 1712 of the inverted tube strips 210 with an absorbent material a sufficient number of times to remove any liquid clinging to the tube lips 1712. One or more contacts may be sufficient, and each successive contact preferably is on a clean part of the absorbent material. The contact duration may be modified, as necessary to obtain the desired results. Longer contact durations also may be used to potentially increase the volume of liquid that is absorbed by virtue of capillary flow or other fluid mechanics. The blotting parameters (number and duration of blots, orientation of the tubes, etc.) may be selected to simulate the process and/or results of a manual blotting process, such as the manual blotting process used in the HC2 protocol. Once blotting is complete for a tube strip 210, the absorbent material is replaced or moved so that the next tube strip 210 contacts uncontaminated material. Any suitable mechanism may be used to invert and blot the tube strips 210. Similarly, and suitable mechanism may be used to provide a clean supply of absorbent material. The absorbent material may be provided as a roll, individual sheets, or in other suitable forms.

Figure 21:
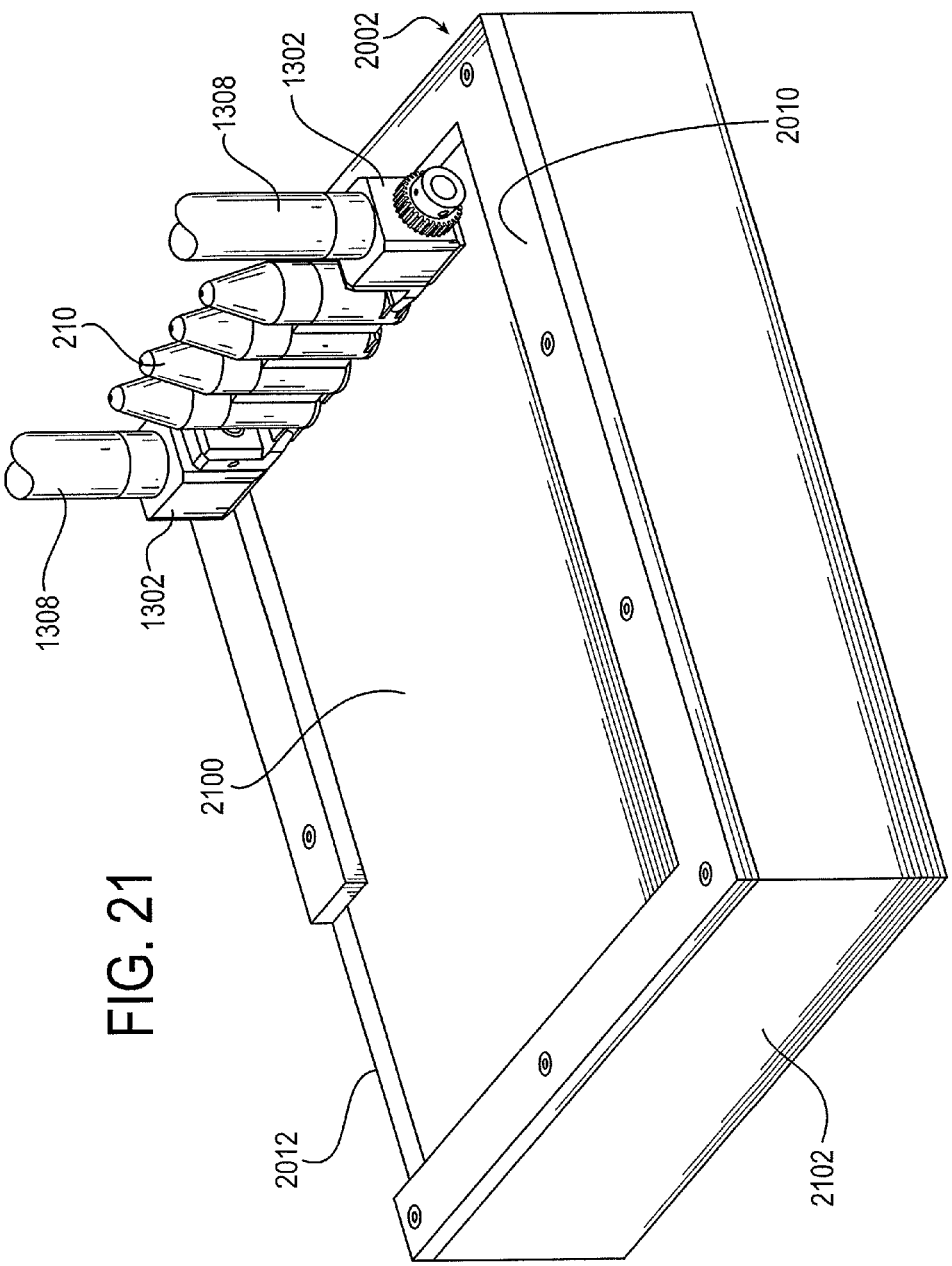
FIG. 21 illustrates an exemplary blotting system with an inverted tube strip prepared for blotting.
Figure 22:
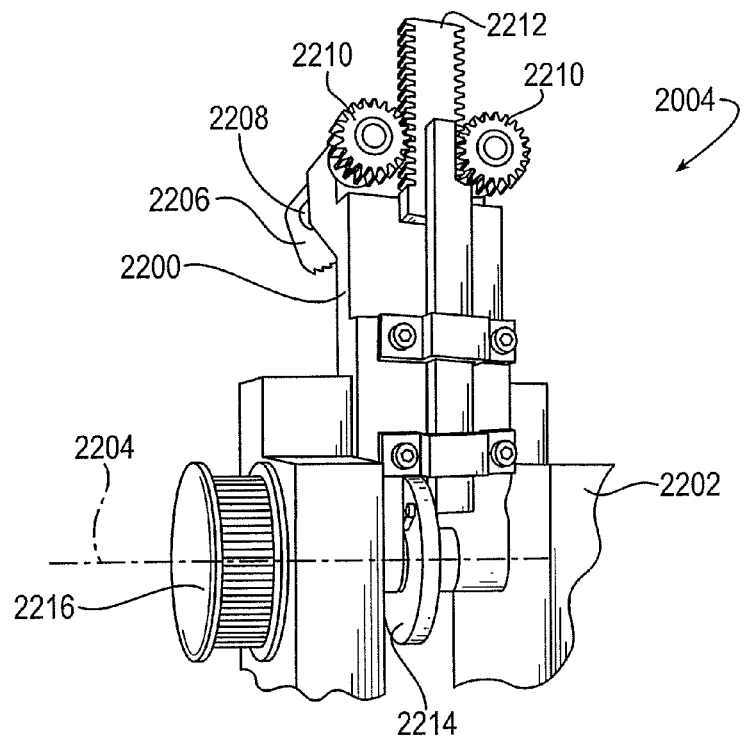
FIG. 22 is a view of an exemplary disposal arm.

Referring in particular to FIG. 21, an exemplary blotting system 2000 may use the previously-described decanting grippers 1302 mounted on respective pipette channels 1308 to hold and blot the inverted tube strip 210. The decanting grippers 1302 may include magnets or other retainers to hold the tube strip 210 in the desired inverted position throughout blotting. Magnets or other resilient holding mechanisms may be provided in the decanting grippers 1302 to allow some rotation to press the tube lips 1712 flat even on an uneven absorbent material surface. It will be appreciated that the orientation for blotting may be different than the orientation used for decanting, and, if this is the case, the tube strips 210 may be rotated to the desired decanting position using mechanisms described above or the like. Blotting may occur immediately after decanting to avoid keeping the tube strip 210 inverted longer any than necessary, and to prevent having to turn the tube strip 210 back to the upright position for storage before blotting.

In this embodiment, the paper supply 2002 comprises a renewable supply of absorbent sheets 2100 comprising paper or another absorbent material. Suitable absorbent sheets include conventional 4-ply low-lint absorbent paper towels used in the manual HC2 assay protocol and sheets made of other paper or nonwoven compositions. The sheet size may be selected to accommodate the number of blots, tube size, and other factors. Each sheet 2100 may have a liquid-impervious backing to prevent contamination of lower sheets, or an impenetrable barrier, such as a removable film, may be provided between sheets in the stack.

Figure 20:
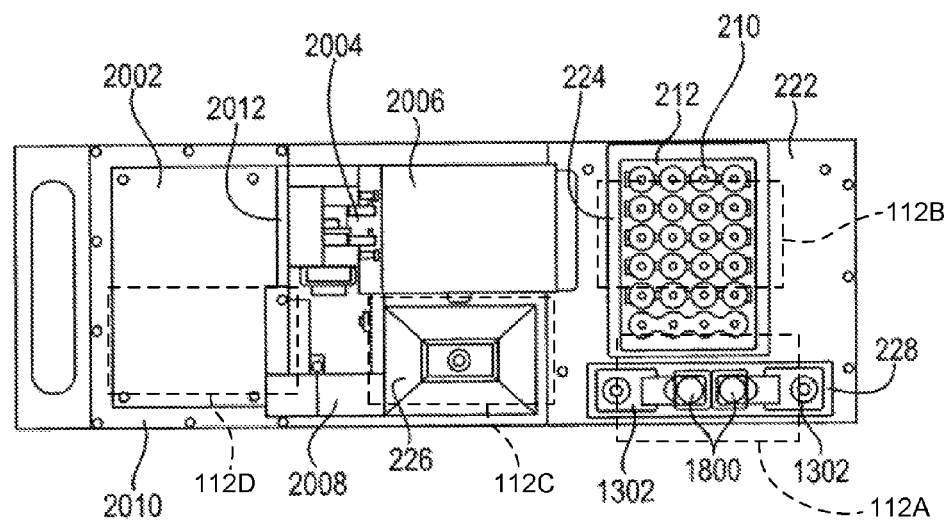
FIG. 20 is a schematic plan view of an exemplary blotting system.

The paper supply 2002 may comprise a box-like structure having sidewalls 2102, an open top, and a lip 2010 surrounding some or all of the open top to retain the sheets 2100. As shown in FIG. 20, the lip 2010 may have a gap 2012 to provide access for a paper disposal mechanism and to facilitate paper removal. A movable platform (not shown) is located inside the box to hold the sheets 2100, and the platform is biased upwards towards the open top by one or more springs, air pressure, or a suitable mechanism, to maintain a supply of sheets 2100 at the open top of the paper supply 2002. As this construction is generally in the form of a common spring-loaded paper dispenser, further explanation of the working parts is not necessary here.

A suitable monitoring system may be provided to detect and report the status of the paper supply 2002. For example, a vertical arrangement of optical detectors (e.g., infrared emitter/detector pairs or the like) may be provided to examine the paper supply 2002 through one or more openings in the sidewalls 2102. Any monitoring technique may be used. For example, the detectors may be used to determine when the sheets are no longer present at the particular level of the respective detector, or they may register the passing of a reference marker, such as a mark on the edge of the spring-loaded platform that holds the sheets 2100. In one exemplary embodiment, four detectors are provided in a vertical stack to evaluate whether the supply is sufficient for a desired number of samples to be processed, and also to indicate when the paper supply is nearing exhaustion. These detectors may be integrated into a control system, and monitored to prevent the module from undertaking automated processing until the supply is replenished to a level suitable to last throughout the processing run. Other detection systems and algorithms may alternatively be used (e.g., a variable resistor other mechanism to measure the height of the platform, or a counter to track the number of sheets used).

The blotting process may be conducted in a manner suitable to remove unwanted liquid clinging to the tubes. The exact requirements for the particular intended application may be established using empirical or other testing methods. In one embodiment, the blotting process may be conducted to replicate the results of a manual HC2 blotting process. In this case, the manual process calls for approximately six blots until liquid no longer drips from the tube. It has been found that an equivalent automated process may use fewer blots if the tubes are shorter than conventional tubes. For example, the tubes 1708 may have the same cone dimensions as a standard 10 milliliter Sarstedt tube, but have a sidewall that reduces the volume to 6 milliliters. In this configuration, it is expected that the liquid more readily flows to the bottom of the tube. For this reason, and possibly others, it has been found that four or fewer blots may be necessary. It will be understood that the embodiments are not intended to be restricted to any particular theory of operation.

In one exemplary embodiment, the tube strip 210 is decanted over the decant waste well 226 for at least one or two seconds, then moved axially (along the tube strip axis) across the drip tray 2008 and over the topmost sheet 2100. Liquid may continue dripping from the tubes as the tube strip 210 moves over the sheet 2100, which may cause cross-contamination if the tubes are blotted on that part of the sheet 2100. For this reason, before blotting begins, the tube strip 210 is moved laterally (perpendicular to the tube strip axis) a sufficient distance to clear the portion of the sheet 2100 that may have become contaminated. After this movement, the first blot is performed by using the pipettor channels 1308 to move the tube strip 210 into contact with the sheet 2100. Prior to each subsequent blot (if multiple blots are performed), the tube strip 210 is lifted and moved laterally a sufficient distance to clear any liquid deposited on the sheet 2100 during the prior blot. The lateral movement also ensures that no tube contacts a portion of the sheet 2100 that has passed under or contacted another tube, to minimize the chance of cross-contamination. The blotting process is repeated until the tubes are deemed, by results of empirical testing or by other means, to be clear of unwanted liquid. Afterwards, the tubes strip 210 is turned back to the upright orientation, by means such as described above, and returned to the tube strip holder 212.

Variations on the above exemplary blotting process will be readily apparent to persons of ordinary skill in the art in view of this disclosure. For example, the sheets 2100 may be traversed laterally between successive blots, instead of moving the tube strip 210.

FIG. 20 is a schematic plan view of an exemplary blotting system, showing the location of the pipettor as it moves the pipette channels 1308 to perform the various tasks described above. The pipettor is positioned at location 112A where the two pipette channels may be used to pick up decanting grippers from the gripper parking location 228. The pipettor is positioned at location 112B where the pipette channels remove a tube strip 210 from the tube strip holder 212. The pipettor is positioned at location 112C where the inverted tube strip is decanted into the waste well 226. The pipettor is positioned at location 112D wherein the tube strip is blotted on the blotting sheet supply 2002. The pipettor moves laterally between each of these locations.

After blotting, the contaminated sheet 2100 is removed to provide a new sheet 2100 for the next blotting procedure. Vacuum pickups, sheet-feeding rollers, and the like may be used to remove the contaminated sheets 2100. In the illustrated exemplary embodiment, the sheets may be removed by a disposal arm 2004 that lifts each contaminated sheet 2100 from the paper supply 2002, and deposits it in the waste chute 2006. The disposal arm 2004 generally includes a pinch mechanism to grasp the sheet 2100, and a transport mechanism to conveys the grasped sheet 2100 to the waste chute 2006.

An example of a disposal arm 2004 is shown in FIGS. 22-25. The disposal arm 2004 includes a rotating arm 2200 that is pivotally mounted to a support 2202 to rotate about an arm axis 2204. The pinch mechanism is located on the free end of the arm 2200, and comprises a pair of sheet grippers 2206 that are mounted on respective shafts 2208. The shafts 2208 are rotatably mounted to the arm 2200 on bushings, bearings, or the like. Each shaft 2208 includes a pinion gear 2210 adapted to rotate the shaft 2208. A central rack gear 2212 is slidably mounted to the arm 2100 and located to drive the pinion gears 2210 as it slides. The rack gear 2212 is between the two pinion gears 2210, and thus the sheet grippers 2206 are counter-rotated by sliding the rack gear 2212 along the arm 2100.

The sheet grippers 2206 may comprise any suitable structures for pinching and lifting a sheet 2100. Smooth or toothed rubber rollers, radial pins or fingers, and other structures may be suitable. Devices that rely on friction with the paper (e.g., rubber rollers) to initiate the pinching motion may require periodic servicing to remove paper dust and other contaminants that might reduce the amount of friction.

Figure 23A:
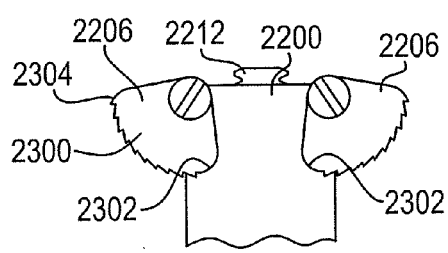
FIG. 23A is a front view of an exemplary sheet gripper, shown in the open position.
Figure 23B:
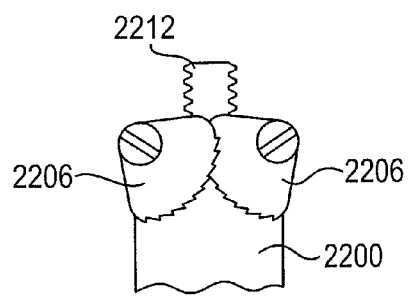
FIG. 23B is a front view of an exemplary sheet gripper, shown in the closed position.

One preferred embodiment for the sheet grippers 2206 is shown in FIGS. 23A and 23B. In this exemplary embodiment, the sheet grippers 2206 comprise toothed wheels. The shown wheels are metal, for durability, but plastic or other materials may be used in other embodiments. The circular perimeter of each wheel may have teeth to provide mechanical grip on the sheets 2100. FIG. 23A shows the wheels in the open position before being operated to grip a sheet 2100, and FIG. 23 shows the wheels in the closed position in which they grip a sheet 2100 (the sheet 2100 is omitted from FIGS. 23A and 23B for purposes of illustrating the parts). The wheels move from the open position to the closed position by counter-rotating, so that the adjacent portions of the wheels pinch and lift the sheet 2100 from the sheet's starting position. In this view, the wheel on the left is rotated counterclockwise, and the wheel on the right is rotated clockwise; thus, the facing portions of the wheels move upwards to pinch and lift the sheet 2100.

As shown, each wheel may comprise an outer perimeter 2300 that subtends an approximately 90° arc. The outer perimeter 2300 may comprise a circular shape with a center point that is located at or near the rotation axis of the shafts 2208, but other shapes (e.g., elliptical, cardioid, etc.) and/or an offset rotation axis may instead be used. The outer perimeter 2300 terminates at a leading edge 2302. As used herein, the leading edge 2302 refers to the end of the outer perimeter 2300 that is in a leading position when the wheel is rotated from the open position to the closed position. The leading edge 2302 may be a sharp corner, but it has been found that forming the leading edge 2302 as a rounded corner provides a less aggressive gripping motion that is less likely to penetrate the top sheet and pick up multiple sheets 2100, and releases the sheet 2100 more easily. One or more generally triangular or shark fin-shaped teeth 2304 are provided on the outer perimeter 2300, and the teeth may be inclined towards the leading edge 2302, such as shown. As shown in FIG. 23B, the wheels may overlap slightly when they are in the closed position. This overlap has been found to assist the process of removing the sheets 2100, but it is not required in all embodiments.

Various modifications may be made to the foregoing sheet gripper 2206 structures in alternative embodiments. For example, each wheel may comprise a continuous circular disc that may or may not have teeth, or the teeth may have different shapes (e.g., square or round).

The sheet grippers 2206 may be actuated by any suitable mechanism. Referring to FIGS. 22, 24A, 24B and 25, the exemplary embodiment includes a drive wheel 2214 that slides the gear rack 2212 to turn the pinion gears 2210. This motion opens or closes the sheet grippers 2206, depending on the direction in which the gear rack 2212 slides. The drive wheel 2214 is mounted on an axle 2500 (FIG. 25) that rotates on the arm axis 2204. A drive gear 2216 is also mounted on the axle 2500. The drive gear 2216 may comprise any driven structure, such as a motor output shaft or a driven pulley. In the shown example, the drive gear 2216 is a toothed gear that is driven by a motor 2502 (e.g., a stepper motor) via a toothed belt 2504 or other intermediate drive devices. Such motors and belts are conventional and need not be described further. The drive wheel 2214 and the drive gear 2216 are rigidly mounted to the axle 2500, so these three parts rotate together as a single unit. The axle 2500 is rotatably mounted to the support 2202, and the rotating arm 2200 is rotatably mounted on the axle 2500. The foregoing parts all rotate around the arm axis 2204.

Figure 24A:
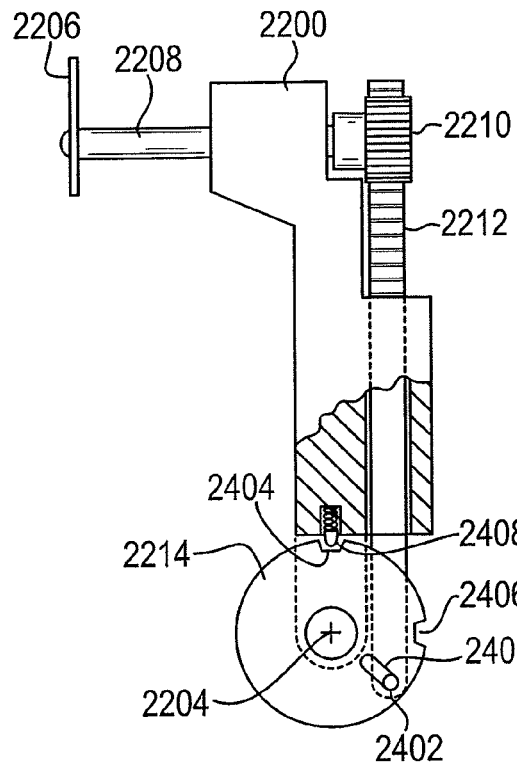
FIG. 24A is a partially cut away side view of an exemplary disposal arm, shown in the open position.
Figure 24B:
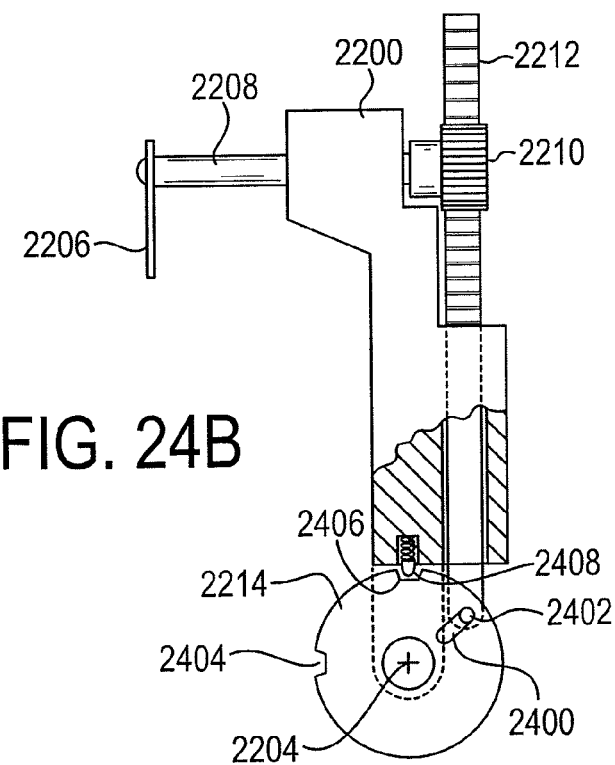
FIG. 24B is a partially cut away side view of the disposal arm of FIG. 24A, shown in the closed position.
Figure 25:
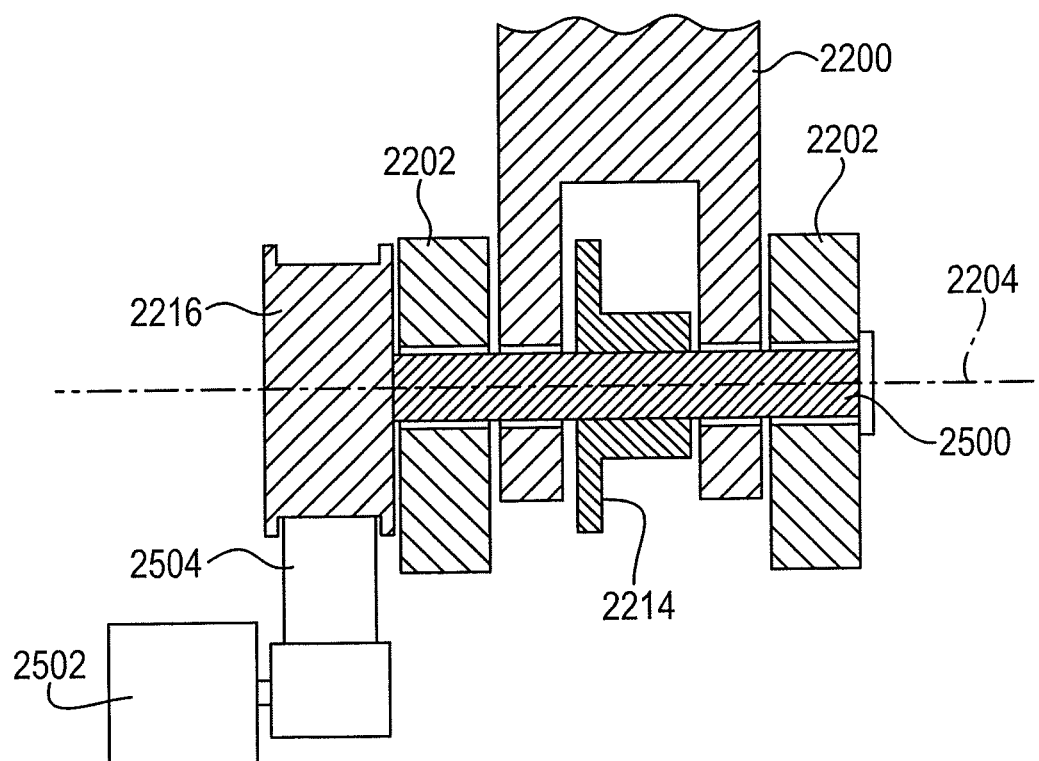
FIG. 25 is a cross sectional view of the lower end of the disposal arm of FIG. 24A, as viewed in the plane of the disposal arm's arm axis.
Figure 26A:
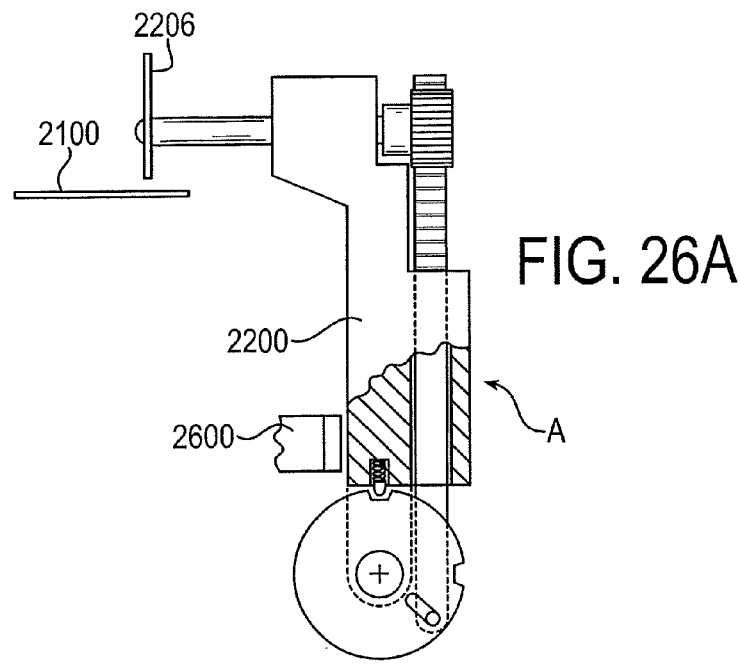
FIGS. 26A-D illustrate four operating positions of the disposal arm of FIG. 24A.
Figure 26B:
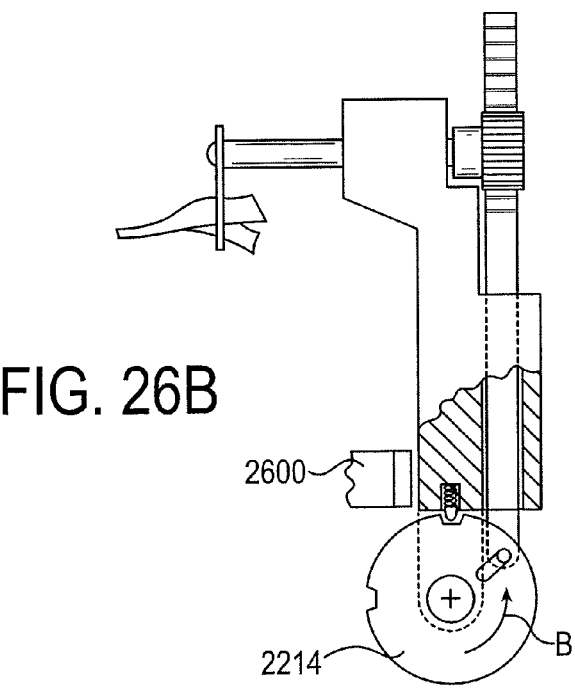
Figure 26C:
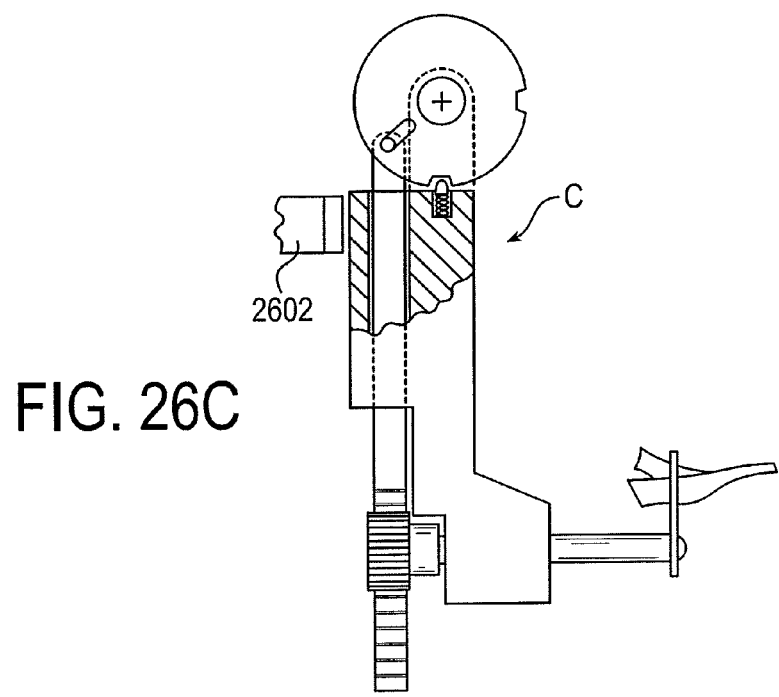
Figure 26D:
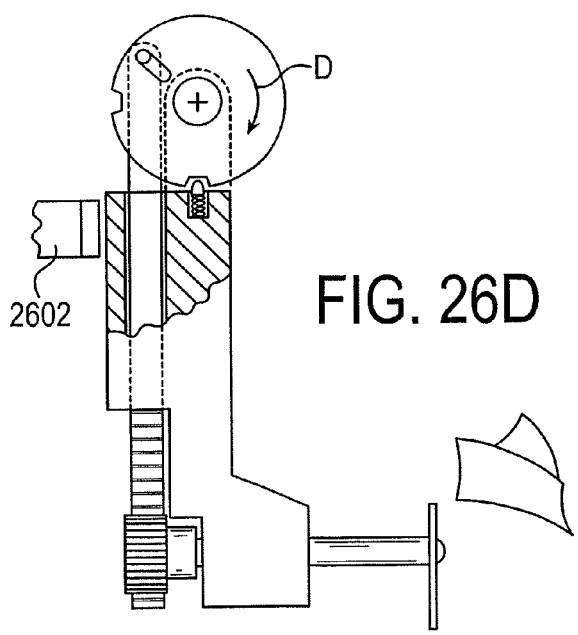

As best shown in FIGS. 24A and 24B, the drive wheel 2214 includes a slot 2400 that surrounds a pin 2402 protruding from the side of the gear rack 2212. Rotation of the drive wheel 2214 relative to the arm 2200 moves the slot 2400, and the slot 2400 drives the pin 2402 to thereby slide the gear rack 2212 along the arm 2200. FIG. 24A shows the drive wheel 2214 and the gear rack 2212 in a first position, in which the sheet grippers 2206 are in the open position as shown in FIG. 23A. FIG. 24B shows the drive wheel 2214 and the gear rack 2212 in a second position, in which the sheet grippers 2206 are in the closed position as shown in FIG. 23B.

The exemplary drive wheel 2214 also includes a first detent 2404 and a second detent 2406 located on the outer perimeter of the drive wheel 2214. The detents 2404, 2406 are separated by a predetermined angle, as measured relative to the arm axis 2204. In this case, the angle is approximately 90°, but other angles may be used in other embodiments. A spring-biased pin or ball 2408 is located in the rotating arm 2200. The ball 2408 is positioned to engage the first detent 2404 when the drive wheel 2214 is in the first position (FIG. 24A), and to engage the second detent 2406 when the drive wheel 2214 is in the second position (FIG. 24B). Engagement between the ball 2408 and either detent 2404, 2406 resiliently joins the arm 2200 to the drive wheel 2214, so that the drive wheel 2214 and arm 2200 rotate in unison. Any suitable ball and detent mechanism (or other resilient holding mechanism) may be used for this purpose, and the selection of the same will be within the ordinary skill in the art in view of the present disclosure.

FIG. 26 illustrates the operation of the disposal arm 2004. In step A, the disposal arm 2004 starts in the first position, with the sheet grippers 2206 open, and the first detent 2404 engaged with the ball 2408. With the assembly in this configuration, the motor 2502 rotates the entire disposal arm assembly in a first direction, as shown by arrow A, until the sheet grippers 2206 are located above a sheet 2100. At this point, the disposal arm assembly contacts a first travel stop 2600 that prevents further rotation of the arm 2200. In this orientation, the disposal arm 2004 is in the pickup position, and ready to pick up a sheet 2100.

In step B, the motor 2502 continues to rotate in the first direction to thereby turn the drive wheel 2214, as shown by arrow B. Torque generated by the motor 2502 overcomes the force holding ball 2408 in the first detent 2404 to allow the drive wheel 2214 to rotate independently of the arm 2200. This rotation continues until the assembly is in the second position with the sheet grippers 2206 closed and the second detent 2406 engaging the ball 2408. During this movement, the sheet grippers 2206 grasp the sheet 2100. A limit switch, position indicator, or other mechanism may be provided to indicate when the drive wheel 2214 is in the desired position, or such information may be obtained by analyzing the motor by a position sensor (e.g., encoder wheel), by a current-detection algorithm that detects increased current as the motor encounters resistance to rotation, or by other suitable mechanism.

In step C, the motor 2502 reverses direction to rotate the entire disposal arm assembly in the opposite direction, as shown by arrow C. Engagement between the ball 2408 and second detent 2406 causes the assembly to rotate as a unit until the assembly contacts a second travel stop 2602. In the shown embodiment, the second travel stop 2604 is located to allow the arm assembly to rotate about 180° from the position shown in steps A and B, but other ranges of travel may be provided. At this point, the second travel stop 2602 prevents the arm 2200 from rotating further in the second direction. In this position, the disposal arm 2004 is in the disposal position, and ready to deposit the sheet 2100.

In step D, the motor 2502 continues to rotate in the second direction to turn the drive wheel 2214 as shown by arrow D. The torque of the motor 2502 separates the second detent 2406 from the ball 2408 to rotate the drive wheel 2214 independently of the arm 2200. The drive wheel 2214 is rotated until the assembly is in the first position, with the sheet grippers 2206 open. The motor 2502 may use any suitable mechanism or control system to stop the rotation when the assembly is in the first position. At this point, the sheet 2100 is released and allowed to drop down the waste chute 2006, and the arm assembly is ready to be moved back to the pickup position shown in step A to remove the next sheet 2100.

Figure 27A:
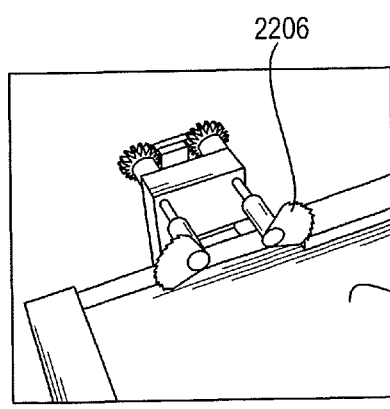
FIGS. 27A-C illustrate an exemplary process for picking up and removing used sheets from an exemplary blotting sheet supply.
Figure 27B:
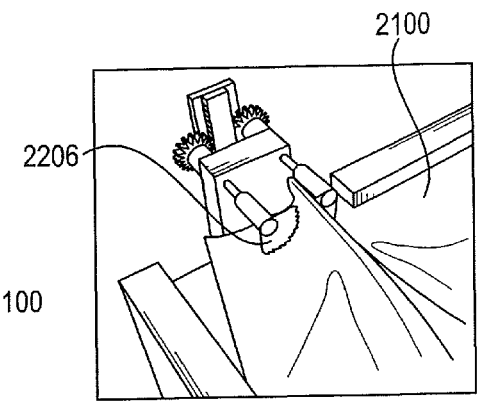
Figure 27C:
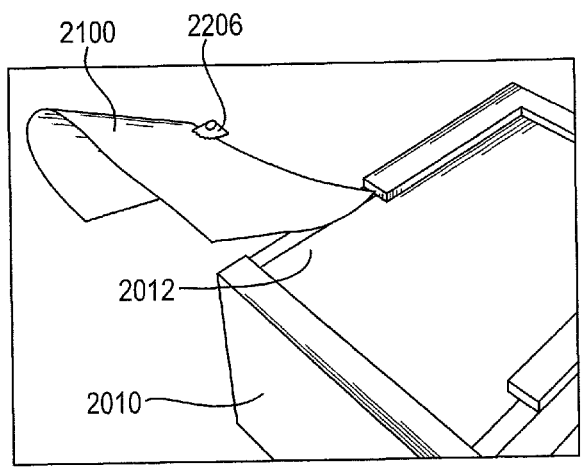

FIGS. 27A-C illustrate the manner in which the sheet grippers 2206 may grasp and retain the sheet. When the sheet grippers 2206 move from the open position (FIG. 27A) to the closed position (FIG. 27B), they pinch and begin to lift the sheet 2100. Rotating the disposal arm backwards (FIG. 27C) pulls the sheet 2100 free of the lip 2010. The gap 2012 in the lip 2010 may provide access for the sheet grippers 2206, and allow the sheet 2100 to release more easily.

If desired, sensors may be provided to detect whether the sheet 2100 has been picked up and properly deposited in the waste chute 2006. Such may be accomplished using conventional optical sensors located where the sheet 2100 is expected to pass, such as at various vertical locations along the waste chute 2006. Also, additional mechanisms may be provided to assist with disposing of the sheet 2100. For example, compressed air may be blown downward to move the sheet 2100, provided sufficient safeguards are provided to prevent the air from disturbing other processes or contaminating the other samples in the module. As another example, the disposal arm 2004 may be operated through one or more additional up and down motions (i.e., moving it back and forth partially or completely between the pickup and disposal positions as shown in FIG. 26) to force down sheets that are trapped in the waste chute 2006.

It will be appreciated that various modifications may be made to the foregoing embodiment. For example, the illustrated drive wheel 2214 has a complete circular shape, but it may comprise only a portion of a circle, or be formed as one or more rotating arms. As another example, the shown toothed pinion gears 2210 and rack gear 2212 also may be modified, such as by using smooth friction rollers, or by using different articulating mechanisms or linkages. Also, in other embodiments, the slot-and-pin arrangement may be replaced by other linkages, gears or other drive arrangements, and the ball-and-detent system may be replaced by other resilient holding mechanisms, such as simple protrusions and notches or magnets. Furthermore, the drive gear 2216 may be driven by any suitable alternative mechanism, such as a reversible DC or AC motor, a pneumatic or hydraulic cylinder, or the like. As another example, the drive gear 2216 is shown as a toothed gear that is driven by a belt 2504, but the drive gear 2216 may comprise a lever arm or other mechanism. In yet another alternative embodiment, the drive wheel 2214 and rotating arm 2200 may be separately operated be separate motors. Other modifications will be appreciated by persons of ordinary skill in the art in view of the present disclosure.

The operating movement also may be modified in other embodiments. For example, other gripping motions may be used, such as by orienting the sheet grippers to grasp the top and bottom surfaces of the sheets, instead of pinching only the top surface. The grippers may also be operated by linkages to provide an articulated non-circular motion. Also, the rotating arm 2200 may be oriented with its arm axis 2204 above the sheet 2100 or at other locations, and the rotating arm 2200 may have a different travel path instead of an arcuate motion as shown herein.

The foregoing blotting system 2000 and embodiments thereof have been found suitable for performing blotting processes, and simulating manual blotting protocols. However, it will be understood that blotting is not required in all embodiments, in which cases the blotting system 2000 is not required. For example, it has been found that blotting is not necessary at all if the decanting process is suitable to decant the liquid without leaving a substantial amount of liquid in the tubes or on the tube lip; and therefore blotting is not required in all embodiments that perform an automated HC2 protocol.

Exemplary Heating Systems

As explained above, a processing module may include one or more heating blocks, such as heater-shakers, to incubate the contents of the tube strips 210. While heating systems are well-known, it has been found that conventional heaters can yield inconsistent heat distribution among the tubes, and cause sample volume loss by evaporation or condensation. These phenomena can impair the reliability of a processing system.

Problems associated with incubation processes are particularly likely when samples are processed in conventional microtiter deep-well plates. Such plates typically have 24, 48 or 96 sample wells integrated into a single plate for simultaneous or essentially simultaneous processing. These plates are often made of molded polypropylene or polystyrene and dimensioned according to Society for Biomolecular Screening ("SBS") conventions for automated processing equipment. Conventional microtiter plates have several shortcomings when it comes to incubation processes. For example, the plastic material that may be selected for its non-reactive properties and low cost is not efficient at conducting heat, and the heat conduction path to the various sample wells can differ greatly. This can lead to the outer wells being heated significantly more or less rapidly than the inner wells. This problem can be mitigated, in some cases, by forming spaces between adjacent wells and using a heating block with metal protrusions that fit into these spaces (so-called "hedgehog" heaters). However, the protrusions on such devices can be complex and fragile, and it still may not be possible to fit the protrusions closely to the standard microtiter plate wells to provide efficient heat transfer. Such heating block systems also are not expected to operate well when the samples or sample containers have relatively large volumes. For example, such protrusions may not extend very far along the vertical extent of each well, leading to relatively little heating at the upper portion of each well. Still further, the protrusions may make it difficult to load the microtiter plate onto the heater, particularly if one were to try to make the protrusions conform closely to the shapes of the wells.

A further problem with conventional plates is that they typically are enclosed by simple flat polystyrene lids that do not seal the individual wells. Some devices have been provided to seal each individual well, such as elastomer plugs and adhesive-backed plastic or metal foils, but these have not been found to be amenable to removal by automated processing systems. In such cases, evaporation during incubation can be a significant problem. Finally, such plates comprise a two-dimensional array of wells, which cannot be decanted without risking cross-contamination caused by liquid passing from one well to another.

Figure 28:
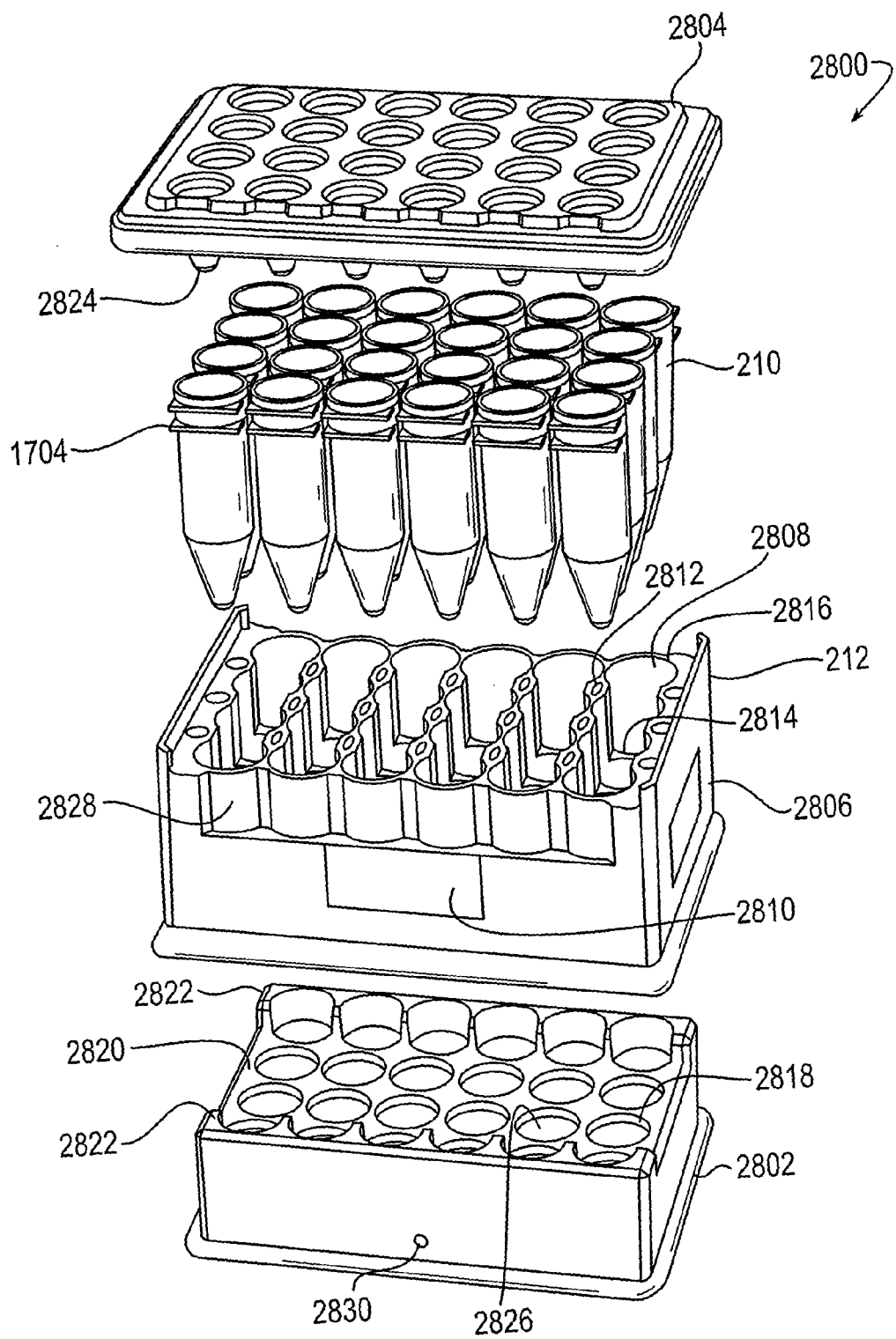
FIG. 28 is an exploded view of an exemplary heating assembly.

FIG. 28 illustrates an exemplary sample heating assembly 2800 that is expected to provide improved incubation performance, such as by providing consistent heating of all samples, and/or reducing losses attributable to condensation or evaporation. The heating assembly 2800 generally comprises a tube strip holder 212 that holds a number of tube strips 210 (such as those described previously herein), a heating block 2802, and a cover 2804. This embodiment is expected to have particular utility for an automated system performing an equivalent to the manual HC2 protocol, but also may be useful for other incubating processes.

The exemplary tube strip holder 212 conveniently is used throughout the processing module, including for general transport and holding, heating, and centrifuging. It will be appreciated, however, that the processing module may have multiple different tube strip holders 212 that are used for different processing steps. The tube strip holder 212 includes an outer frame 2806 that contains a plurality of tube strip wells 2808. The outer frame 2806 generally surrounds the tube strip wells 2808 and optionally may be shaped and sized to match the conventional SBS plate geometry. Features such as gripping surfaces 2810 (e.g., grooves or knurled surfaces) also may be provided to assist with positive gripping and preventing slippage during transport. The tube strip wells 2808 are configured to receive one or more tube strips 210. The tube strip wells 2808 terminate at an upper lip 2816, which may be positioned to vertically support the tube strips 210 during transport and certain processing steps. For example, the tube strips 210 may have lower ribs 1704 (FIG. 17) that rest on the lip 2816 to support the tube strips 210, while still providing access to the channels 1700 and inboard tabs 1706. Other arrangements of supporting structures may be used in other embodiments. For example, the tube strips 210 may be supported by longitudinal walls 2814 and/or other structures. In the shown embodiment, adjacent tube strip wells 2808 are separated by vertically-extending lateral walls 2812, and longitudinal walls 2814 may be located between adjacent tubes in each tube strip 210. The tube strip holder 212 preferably is made of magnesium or other materials having a high thermal conductivity and relatively high strength-to-weight properties. A magnesium tube strip holder 212 may be machined, molded, cast, or formed by any variety or combination of processing steps. Other suitable materials may include aluminum or other metals, plastic materials, or combinations of materials.

The heating block 2802 comprises a thermally-conductive material that may be mounted on a conventional heater-shaker or other heat source. Aluminum is a preferred material for the heating block 2802 because it has high thermal conductivity, and can convey heat from a heating device to the tube strips with relative speed, and it is relatively light and therefore can be operated as a shaker (e.g., an orbital shaker) with relatively little effort. Nevertheless, other materials may be used. For example, the heating block 2802 may be formed of steel, and maintained at an elevated temperature or pre-heated when it is desired to heat the tube strips 210. The exemplary heating block 2802 includes a plurality of heating wells 2818, each of which preferably receives a single tube 1780, as explained below. The heating block 2802 also may have a central region 2820 comprising a surface at a first height, and side regions 2822 comprising surfaces that are taller than the central region, the purpose of which is described below. A bore 2830 may be provided in the heating block 2802 for inserting a thermocouple to monitor the heating block's temperature. The heating block 2802 may be mounted on a conventional heater, such as an electric heater-shaker, or it may have its own dedicated heating element or elements.

The cover 2804 is configured to cover the tube strips 210. As shown, the cover 2804 may include a plurality of protrusions 2824 that are positioned to extend into each tubes of each tube strip 210. The cover 2804 may be made of clear polystyrene or other materials. Polystyrene is preferred in one embodiment, because it holds its manufacturing tolerances fairly well, and is hydrophobic. If hydrophilic materials are used in other embodiments, they may optionally be treated with hydrophobic coatings or the like. The cover 2804 may comprise multiple layers that are spaced apart, but joined at their perimeter or other locations, to form an insulating air or gas barrier within the cover itself. The cover 2804 also may be have structures on its upper surface to facilitate stacking of other covers 2804, tube strip holders 212, or other parts.

Figure 29:
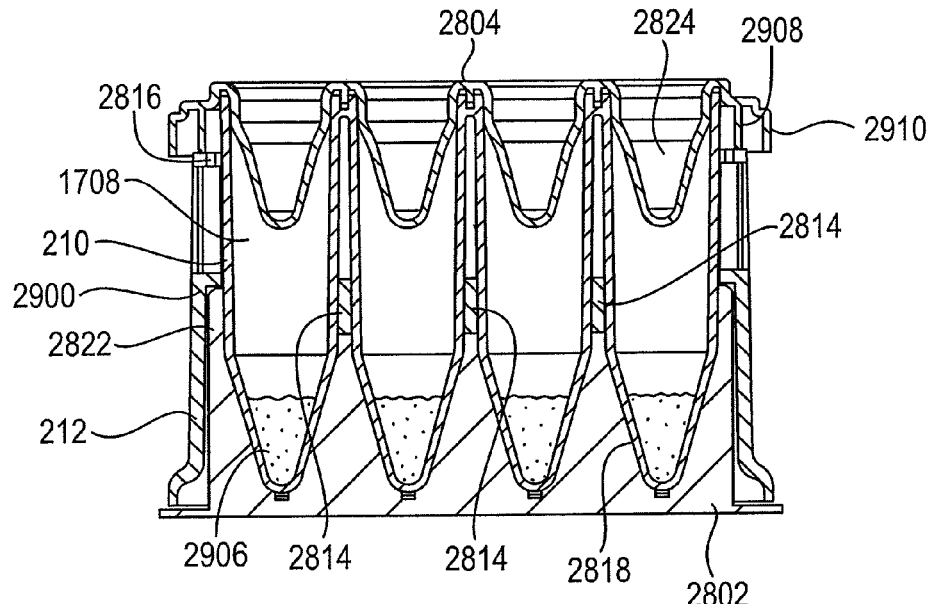
FIG. 29 is a lateral cross sectional view of the heating assembly of FIG. 28, shown in the fully-assembled configuration, and with the cross section taken through the axis of a tube strip.
Figure 30:
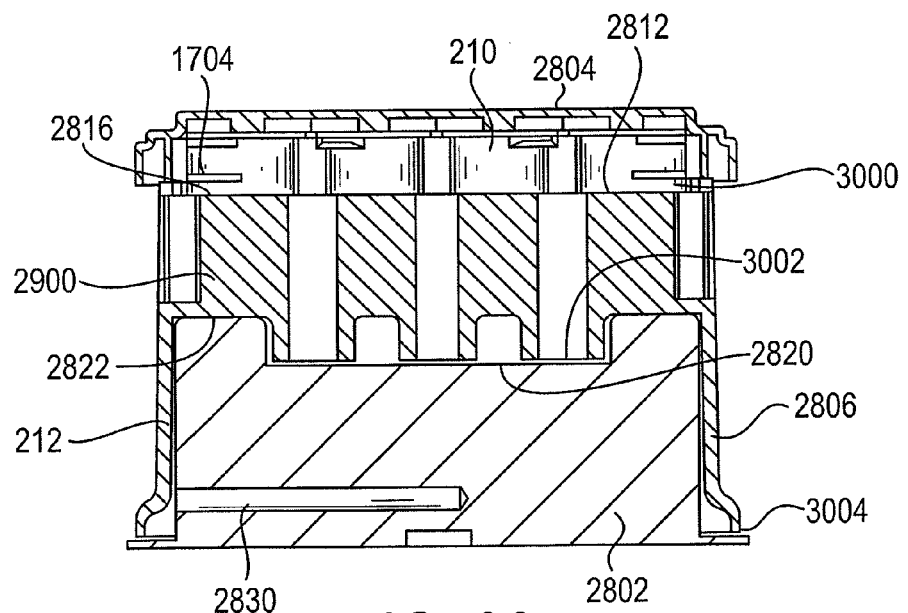
FIG. 30 is a lateral cross sectional view of the heating assembly of FIG. 28, shown in the fully-assembled configuration, and with the cross section taken through a lateral wall of the tube strip holder.
Figure 31:
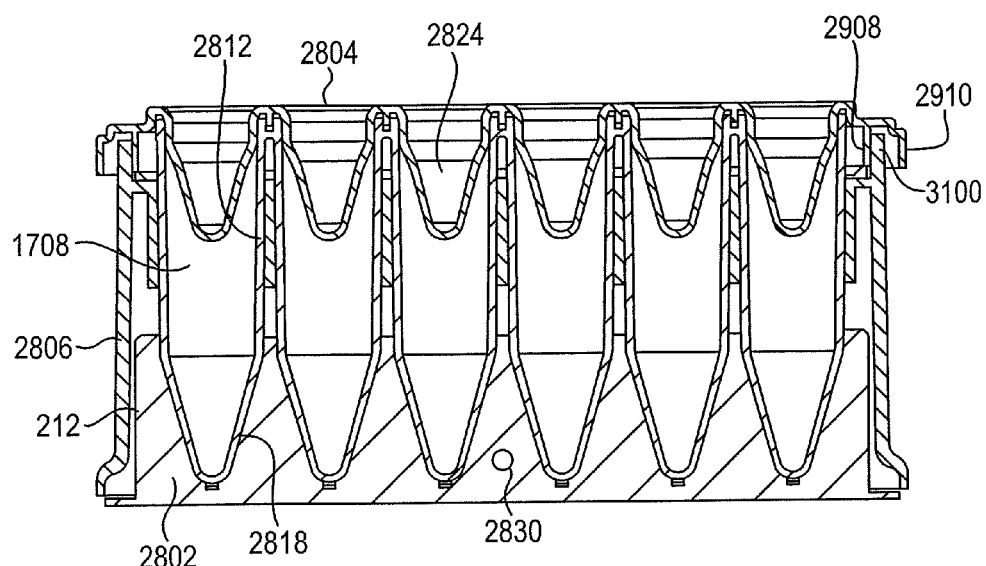
FIG. 31 is a longitudinal cross sectional view of the heating assembly of FIG. 28, shown in the fully-assembled configuration.

FIGS. 29-31 illustrate the manner in which the exemplary heating assembly 2800 parts may fit together. FIG. 29 is a lateral cross section through the centerline of one of the tube strips 210. FIG. 30 is a lateral cross section through one of the lateral walls 2812 adjoining two tube strip wells 2808. FIG. 31 is a longitudinal cross section through all of the tube strips 210.

When the parts are fully-assembled, each tube 1708 is located within a respective heating well 2818, and both the tube strips 210 and the tube strip holder 212 are supported in the vertical direction by the heating block 2802. In the exemplary embodiment, the heating wells 2818 support the tubes 1708, and the tube strip holder 212 has an internal shelf 2900 that rests on the side regions 2822 of the heating block 2802. When the tube strip holder 212 is raised off the heating block 2802, it may move vertically a short distance before it begins to lift the tube strips 210. This helps ensure that the tube strips 210 are in close contact with the heating block 2802, and not held out of contact with the heating block 2802 by the tube strip holder 212. For example, lower ribs 1704 at each end of each tube strip 210 may rest on the upper lip 2816 of the tube strip holder 212 when the tube strip holder 212 is not mounted on the heating block 2802. But when the parts are assembled to the heating block 2802, the heating wells 2818 may support the bottoms of the tubes 1708 to leave a small gap 3000 between the lower ribs 1704 and the upper lip 2816. In this case, the tube strip holder 212 can move vertically by the distance of the gap 3000 before it contacts and lifts the tube strips 210 out of contact with the heating block 2802. The gap 3000 preferably is equal to or greater than the expected stacked manufacturing tolerances of the relevant dimensions.

The heating wells 2818 surround a predetermined amount of each tube 1708. Preferably, the heating wells 2818 are shaped to closely match the outer surface of each tube 1708, in order to maximize contact between the two and provide the most efficient heat transfer. To provide predictable and uniform heating, the surfaces of the tubes 1708 and heating wells 2818 that are intended to contact one another may be made with relatively high manufacturing tolerances, or otherwise designed to provide repeatable contact with one another. In the shown embodiment, the wells 2818 closely fit the conical bottom portion of each tube 1708, and are formed with a conical wall 2826 that diverges at a slightly greater angle than the outer wall of the tube 1708. With these generally matching geometries, the tubes 1708 are likely to contact the heating wells 2818 at or near the lowermost portion of each heating well 2818, and the slightly greater conic angle of the heating wells 2818 ensures that the tubes 1708 can easily fall into place without undue dragging on the heating well 2818 walls. In other embodiments, alternative matching geometries may be provided to form a contact area between each tube 1708 and each heating well 2818. For example, the heating wells 2818 may extend above the conical portion of each tube 1708, or, if the tubes 1708 are cylindrical, each heating well 2818 may have a flat bottom that closely matches the bottom of each tube 1708.

As noted above, the tube strip holder 212 may comprise magnesium or another material having high thermal conductivity properties, to thermally couple the tube strip holder 212 to the heating block 2802 and turn it into an effective part of the heating assembly 2800. Heat is transferred from the heating block 2802 to the tube strip holder 212 primarily by conduction at the locations where the tube strip holder 212 rests on the heating block 2802. As shown in FIG. 30, the internal shelf 2900 on the tube strip holder 212 may contact a relatively large portion of the heating block side regions 2822 to provide a heat transfer surface. To ensure that these parts are in proper contact, gaps may be provided at other locations where tube strip holder 212 is in close proximity to the heating block 2802 to prevent those regions from abutting one another and preventing contact at the desired heat transfer surface. For example, a first gap 3002 may be provided between the lateral wall 2812 and the central region 2820 of the heating block 2802, and a second gap 3004 may be located between a bottom edge of the outer frame 2806 and the heating block 2802. These gaps 3002, 3004 preferably are equal to or larger than the stacked manufacturing tolerances of the relevant parts.

To increase heat transfer to the individual tubes 1807, the tube strip wells 2808 may closely match the shape of the tube strip 210. For example, the gap between the tube strip wells 2808 and tubes 1708 may be only large enough to ensure consistent loading and unloading of the tube strips 210. Variations in the gap size may be provided to regulate heat transfer to particular tubes 1708 along each tube strip 210 (e.g., end tubes may have smaller gaps for greater heat transfer). In the exemplary embodiment, the tube strip wells 2808 comprise a series of conjoined semicircular walls that closely surround the tube strip 210 and partially wrap around the upper portion of each individual tube 1708. As shown in FIG. 28, the ends 2828 of the tube strip wells 2808 may form portions of the outer frame 2806. In this case, the outer frame 2808 may be contoured to ensure that the ends 2828 of the tube strip wells 2808 have a generally consistent thickness to provide more uniform heating in this region. As shown in FIG. 29, the longitudinal walls 2814 are located between adjacent tubes 1708 to help surround the tubes 1708. FIG. 31 illustrates how the lateral walls 2812 also surround portions of each tube 1708.

The outer frame 2806 of the tube strip holder 212 may form an enclosure that generally surrounds the heating block 2802 and tube strips 210. With this configuration, the outer frame 2806 provides a heat-containing enclosure that holds heated air in proximity to the tubes 1708. Thus, any parts of the tubes 1708 that are not closely surrounded by either the heating wells 2818 or the tube strip wells 2808 are surrounded by heated air captured within the outer frame 2806. This may form a beneficial heat convection path to convey heat from the heating block 2802 to the rest of the heating assembly 2800, and help isolate the tubes 1708 from irregular cooling patterns that might be caused by the ambient environment (e.g., breezes, nearby heat sources, or the like).

The heating block 2802 and tube strip holder 212 preferably are configured to provide consistent heating throughout the upper and lower portions of the tubes 1708. To this end, the heating block 2802 may be configured to contact and conduct heat to the outer perimeter of the tube strip holder 212, because the outer walls have a higher heat transfer rate to the ambient environment and may otherwise remain at a lower temperature than the interior portions of the tube strip holder 212. For example, as explained above, the heat conduction surface from the heating block 2802 to the tube strip holder 212 may be formed as a pair of raised side regions 2822 on either side of the heating block 2802. In this arrangement, heat transfers by conduction to the outer sides of the tube strip holder 212 and then conducts inward through the lateral walls 2812 and longitudinal walls 2814 to heat the inner portions of the tube strip holder 212. At the same time, ambient air surrounding the heating assembly 2800 may continuously remove heat from the outer portions of the tube strip holder 212. When these heat transfers reach equilibrium, the tube strip holder 212 preferably heats the upper portions of all of the tubes 1708 at approximately the same rate.

Other embodiments may use other arrangements of heat conducting surfaces between the heating block 2802 and the tube strip holder 212. For example, the two raised side regions 2822 may be omitted, and replaced by a cutout on the bottom of the tube strip holder 212 that limits contact with the heating block 2802 to the outer perimeter of the tube strip holder 212. As another example, the raised side regions 2822 may be joined at their ends to form a raised wall that extends continuously around the perimeter of the heating block 2802. This may be beneficial if the heating assembly 2800 has a square or circular shape instead of the shown rectangular shape. As still another example, the raised side regions 2822 may be replaced by a plurality of pedestals or other surfaces of various shapes and sizes that contact the tube strip holder 212 at various locations to distribute heat throughout the tube strip holder 212, while preferably also accounting for expected heat loss to the ambient air, to thereby provide uniform heating. Other variations and modifications will be apparent to persons of ordinary skill in the art in view of the present disclosure.

The cover 2804 also may form a functional part of the heating assembly 2800. A unitary cover 2804 that extends over all of the tubes 1708 and intervening spaces acts as a heat trap that inhibits heated air from leaving the proximity of the tubes 1708. To improve this heat trap, the cover 2804 may comprise one or more downward-extending skirts to retain heated air under the cover 2804. For example, the shown embodiment has an inner skirt 2908 and an outer skirt 2910 that extend downward towards the heating block 2802. The skirts 2908, 2910 are located around the perimeter of the cover 2804 to help trap heated air under the cover 2804. The skirts 2908, 2910 may extend entirely or only partially around the perimeter of the cover 2804. As shown in FIG. 31, the skirts 2908, 2910 optionally may straddle a wall 3100 that extends upward from the tube strip holder 212 to form a labyrinthine path to impede the escape of heated air. The wall 3100 may extend all the way around the perimeter of the tube strip holder 212, or only portions thereof. In the shown embodiment, the wall 3100 is provided only along the longitudinal ends of the tube strip holder 212. The cover 2804 also may assist with uniform heating by effectively sealing each tube 1708, as well as by preventing condensation or evaporation, as discussed below.

Various aspects of the foregoing exemplary embodiments and variations thereof are expected to assist with providing particularly beneficial heating performance. For example, the heating wells 2818 provide close contact with the bottom of each tube 1708, and thus provide efficient heating of the samples contained therein. This is particularly true where the entire volume of the liquid sample 2906 is located within the vertical extent of the heating well 2818, as may be the case when processing a sample for HPV testing according to the HC2 protocol. Another benefit is that the tube strip holder 212 provides an efficient heat conduction path to heat the upper portions of the tubes 1708. In a preferred embodiment used for HPV testing according to the HC2 protocol, the upper portion of each tube 1708 contains only air and possibly trace amounts of liquid. Using normal heating systems, the upper portion of each tube 1708 and the air within may be heated only incidentally, or not at all, which may be intentional to prevent unwanted evaporation. However, the lack of heating may contribute to condensation forming within the tube, which causes a different kind of sample loss. In contrast, the exemplary embodiment uses the tube strip holder 212 to heat the upper portion of each tube 1708 (and thus the air, liquid and water vapor within) to help prevent the formation of condensation. Other benefits may be realized and obtained in these and other embodiments.

Figure 32:
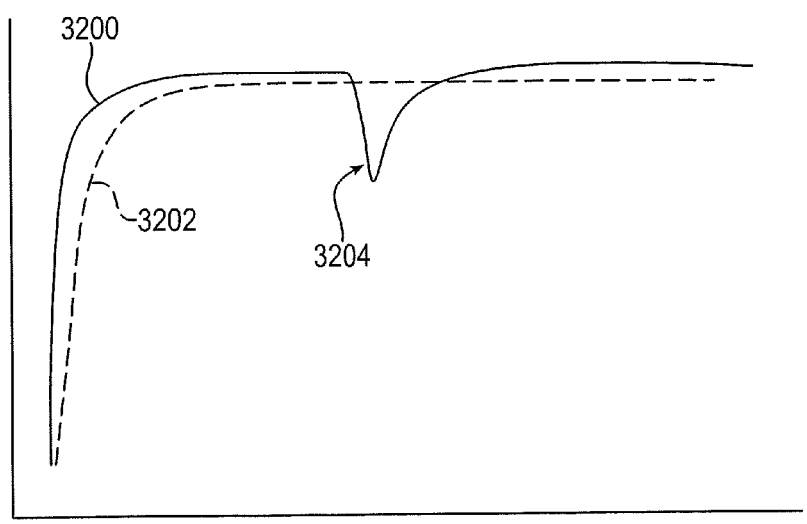
FIG. 32 is a schematic temperature versus time plot comparing a manual heating process to an automated heating process.

FIG. 32 is a temperature ("T") versus time ("t") plot comparing the performance of an exemplary heating system as described above with a conventional water bath heating system used in the manual HC2 protocol. A solid line 3200 illustrates the temperature of a sample processed according to the manual HC2 protocol. In the manual HC2 protocol, the sample is placed in a 65° (±2°) Celsius water bath 15 (±2) minutes, removed from the water bath and vortexed for 15-30 seconds, and replaced in the 65° (±2°) Celsius water bath for 30 (±3) minutes. Line 3200 shows that the sample temperature raises relatively quickly when it is placed in the water bath, but the temperature experiences a significant drop 3204 during the vortexing step. A dashed line 3202 illustrates the temperature profile of a sample heated using a heating assembly 2800 such as described above. The sample temperature rises marginally more slowly than the sample processed in a water bath, but the temperature does not drop during the vortexing step because vortexing is performed without removing the samples from the heating assembly 2800 by mounting the heating assembly 2800 on a conventional electric heater-shaker. The resulting time at temperature is similar in both scenarios. As a result, the total incubation time and final results for both samples are approximately the same.

As noted above, the cover 2804 may be configured to help reduce undesirable sample evaporation and condensation. This benefit may be particularly desirable when the incubation temperature is high, the incubation time is long, the sample volume is relatively small, or the tube volume is relatively large. For example, in the case of an automated equivalent to the manual HC2 protocol, all of these conditions may exist. In this case, the incubation time may be at 65° Celsius for 45 minutes, the sample volume may be approximately 200 microliters, and the tubes may have a diameter of approximately 14 millimeters. For this protocol, it may be desirable to limit losses due to evaporation and condensation to 30 microliters or less.

Figure 33:
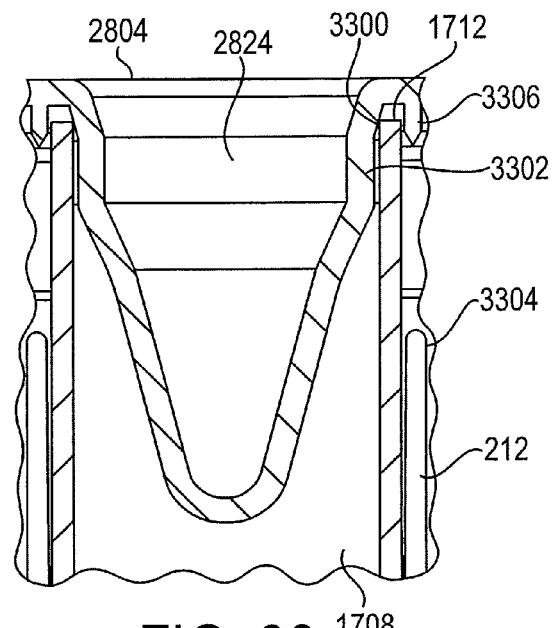
FIG. 33 is a cross sectional view of an exemplary cover, tube and tube strip holder, as viewed through a downwardly-extending protrusion.

FIG. 33 is a cross section of an exemplary cover 2804, shown installed on a tube 1708 mounted in a tube strip holder 212. The cover 2804 may include features intended to limit condensation and evaporation during incubation. The shape of the cover 2804 is intended for an automated equivalent to the manual HC2 protocol, but it may be used in other applications with or without modification. The cover 2804 comprises a plurality of protrusions 2824 that each fit into a respective tube 1708. Each protrusion 2824 preferably includes an upper seal 3300, a lower seal 3302, and a lower conic section 3304, as described below.

The upper seal 3300 is formed as a first conical wall that seats against the upper lip 1712 of the tube 1708. The first conical wall starts at a first diameter that is larger than the diameter of the upper lip 1712, and tapers in the downward direction to a second diameter that is smaller than the diameter of the upper lip 1712. The angle of the first conical wall may be in the range of approximately 15° to 20°, and preferably is approximately 15°, but other angles may be used as desired. Direct contact between the first conical wall and the upper lip 1712 seals the tube 1708.

The lower seal 3302 is located below the upper seal 3300, and is formed as a second conical wall that approximately matches the draft angle (e.g., approximately 1°) of the adjacent inner wall of the tube 1708. Thus, the second conical wall is approximately parallel to the tube 1708. The second conical wall has a diameter that is slightly less than the inner diameter of the adjacent tube wall, in order to create a capillary seal upon contact with liquid that remains at or near the tube's lip 1712 after the decanting process. For example, a gap of approximately 0.2 mm to 0.3 mm may be used to form a capillary seal using the supernatant liquid in the HC2 protocol. Where more or less viscous fluids are in the tube 1708, the gap may be adjusted accordingly to provide the desired capillary seal.

The vertical height of the lower seal 3302 may be selected to enhance the likelihood that a complete capillary seal will be formed, and a taller wall may be likely to contact more residual fluid and thus be more likely to form a complete capillary seal around the entire wall. A taller seal also helps isolate the tube contents, even without a capillary seal. However, a taller seal may seal too tightly for reliable automated processing, and therefore the wall should not be so long as to interfere with the automated process. In a preferred embodiment, the second conical wall that forms the second seal 3302 has a vertical length of approximately 2.5 mm to 3.0 mm.

Is has also been found that the lower seal 3302 may help resist or prevent the cover 2804 from shaking off during mixing operations. A conical protrusion into a tube 1708 is likely to climb upwards during rapid shaking, and particularly orbital shaking. The parallel wall of the lower seal 3302 does not exhibit this phenomenon, and therefore helps to hold the cover 2804 in place during mixing.

The use of the foregoing two seals is expected to provide more consistent sealing results for all of the tubes 1708 held in a single tube strip holder 212. While the upper seal 3300 may effectively seal the tube 1708, variations in the flatness of the cover 2804 may cause a gap between some of the upper seals 3300 and their respective tubes 1708. In those cases, the lower seal 3302 provides a capillary seal that helps isolate the contents of the tubes 1708 from the ambient environment. The foregoing seals also do not require supplemental sealing devices, such as O-rings or the like, and are readily formed using conventional processing techniques.

It will be appreciated that the foregoing upper and lower seals 3300, 3302 may be modified in various ways. For example, the upper seal 3300 may be made of a wall that is not conical (e.g., a series of stepped square ridges or a curves wall). As another example, there may be a gap between the upper seal 3300 and the lower seal 3302. Other variations and modifications will be apparent to persons of ordinary skill in the art in view of the present disclosure.

The cover 2804 also may include additional features to help seal the tubes 1708. For example, each protrusion 2824 may be surrounded by an outer ring 3306 that extends downward from the cover 2804. The outer ring 3306 preferably extends below the upper lip 1712 of the tube 1708 to provide a tortuous path between the interior of the tube 1708 and the ambient environment. Thus, the outer ring 3306 helps isolate the contents of the tubes 1708 if the upper and lower seals 3300, 3302 do not form complete seals.

The lower conic section 3304 extends below the lower seal 3302 and into the tube 1708. The illustrated exemplary lower conic section 3304 has two regions having different conical taper angles, and a rounded tip, but these particular features are not required in all embodiments, and the lower conic section 3304 may be modified or omitted in other embodiments. As shown in FIG. 33, the lower conic section 3304 also may extend below the top of the tube strip holder 212. The lower conic section 3304 may help suppress the formation of condensation as it is heated by the tube strip holder 212, by providing a heated mass within the tube 1708 and displacing some volume of air in the tube 1708. It has been found that a protrusion 2824 into the tube 1708 transfers more heat to the tube's contents than a flat cover. It may be desirable to locate the tube strip holder 212 close to the bottom of the cover 1804 to enhance heat transfer to the lower conic section 3304. Such close placement also may help provide a mass of warmed air surrounding the tubes 1708 to prevent local cool spots at which condensation might form.

It has been found that a cover 2804 constructed substantially as described above and shown in FIG. 33 helps reduce evaporation and condensation. Testing indicates that a relatively minor amount of condensation forms on the lower conic section 3304 and inner wall of the tube 1708. The condensation forms at a slightly cooler region located above the level of the tube strip holder 212, and primarily on the lower conic section 3304 of the protrusion 2824. In these tests, the amount of liquid lost to condensation and evaporation in the tube 1708 did not exceed the maximum limit for the particular HC2 test protocol. It is expected that even lower condensation may be obtained by more directly heating the lid 2804 and protrusions 2824. For example, the lid 2804 and protrusions 2824 may be heated by a radiant heater or convection heater, or by an upper heating block that contacts the cover 2804 (e.g. heated prongs that extend down into the protrusions 2824). Other variations and modifications will be apparent to persons of ordinary skill in the art in view of the present disclosure.

The foregoing arrangement is expected to reduce or minimize air exchange between the interior of the tube, with its saturated water vapor, and the ambient environment. In alternative embodiments, the features of the cover 2804 may be used separately or in combination with other structures. Also, the cover 2804 may be divided into separate units, such as units that cover individual tubes 1708 or tube strips 210. The cover 2804 preferably is formed as a stackable shape, and may include features (e.g., tabs, grooves, opposed surfaces or the like) to permit robotic manipulation using mechanical grippers, vacuum handlers, or the like.

It will be appreciated that the various features of a heating system 2800 that are described herein may be used collectively, separately, or in various combinations. For example a tube strip holder 212 having heat conducting features may be used in conjunction with a heating block 2802, but without a cover 2804. As another example, a cover 2804 having some or all of the features described herein may be used with conventional deep well plates or other heating systems. In addition various additions may be made to the foregoing embodiments. For example, the heating wells 2802 may include a water supply to enhance heat transfer to the tubes 1708.

Exemplary Tube Strip Holder Features

As noted above, the tube strip holder 212 may be used for a variety of operations in addition to heating. As explained previously, the tube strip holder 212 may be used to hold the tube strips 210 for transportation throughout a processing module, and may be configured to facilitate decanting and blotting operations by permitting access by decanting grippers and the like. Where the tube strip holder 212 is used in a processing module that performs an automated equivalent of a manual HC2 protocol, it also may be desirable to use the tube strip holder 212 during machine vision inspection of the tube contents or during centrifuging operations.

Figure 34:
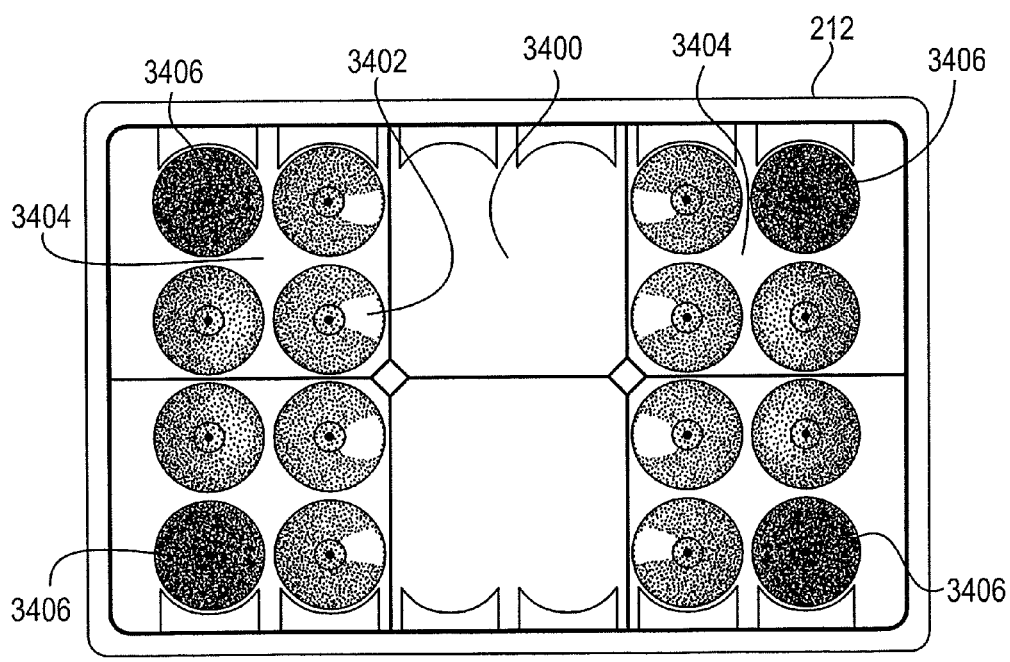
FIG. 34 is an exemplary light exposure of one embodiment of a tube strip holder.
Figure 35:
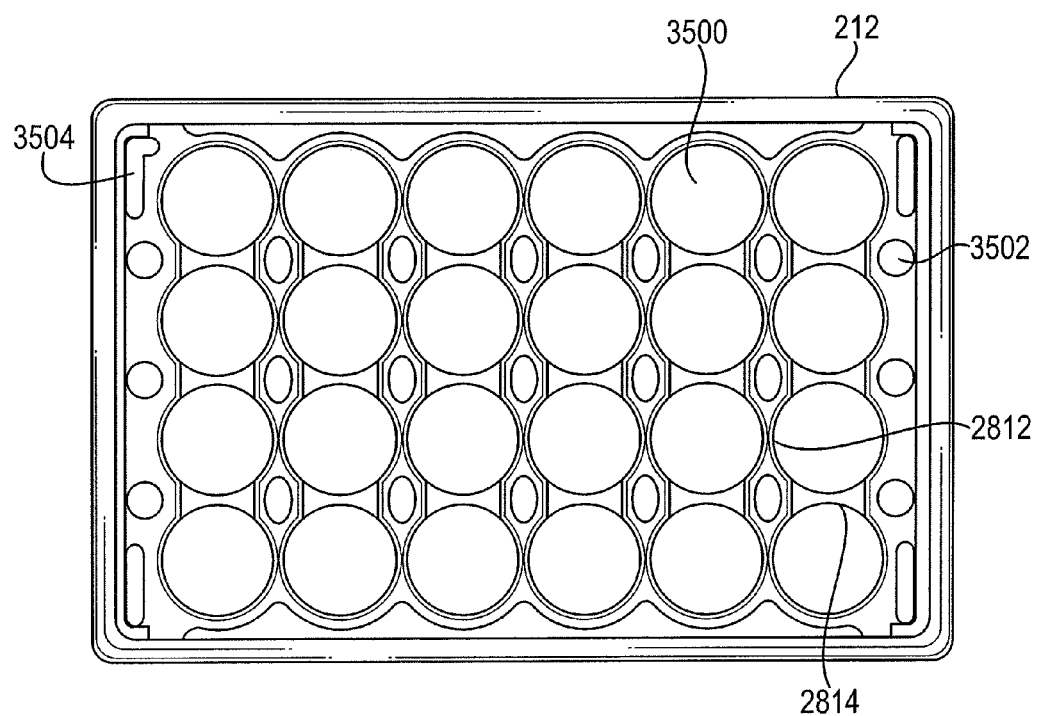
FIG. 35 is an exemplary embodiment of a tube strip holder formed as an optical mask.

Referring to FIGS. 34 and 35, the tube strip holder 212 may be used as an optical mask for a machine vision inspection, such as may be performed by a vision inspection station 218. During vision inspection, a light source is activated to illuminate the contents of the tubes and one or more cameras or other sensors are used to evaluate the light pattern to determine whether the tubes contain pelletized samples. Typical optical analysis equipment for conventional multi-well plates use a light source such as an array of light-emitting diodes passing through a diffuser, or other diffuse sources intended to provide uniform illumination to all of the wells. It has been found, however, that optical testing of an array of tube strips 210 held by a tube strip holder 212 can cause problems unique to this arrangement. In particular, light passing through the tube strip holder 212, but not through the tube strips 210, can overexpose the sensor, or provide properly-exposed images of the tubes in the center of the tube strip holder 212 but underexposed images of the tubes around the perimeter. It has also been found that removing one or more tube strips 210 from the tube strip holder 212 causes even more severe overexposure, and may allow light to reflect off the tubes adjacent the missing tube strips 210, causing glare that inhibits proper optical testing.

FIG. 34 illustrates an example of a tube strip holder 212 that experiences significant exposure problems during optical testing. This tube strip holder 212 is formed as a simple rectangle having one longitudinal cross-wall 3408 and two lateral cross-walls 3410. The design of this tube strip holder 212 is intended to minimize weight (and thus centrifuging loads), and have low material and manufacturing costs. Despite these benefits, the tube strip holder of FIG. 34 has been found to have problems during optical testing. For example, there is an overexposed region 3200 where tube strips 210 have been removed, glare 3202 caused by the large overexposed region 3200, smaller overexposed regions 3404 between adjacent tube strips 210, and underexposed tube images 3406 at the perimeter of the tube strip holder 212.

It has been found that these problems may be overcome by forming the tube strip holder 212 as an optical mask that substantially blocks light from bypassing the tubes, and reduces or prevents glare from reflecting off tubes when a tube strip 210 is removed. As shown in FIG. 35, the tube strip holder 212 is formed with lateral walls 2812 and longitudinal walls 2814 that form a separate opening 3500 for each tube. During exposure, these walls 2812, 2814 form an optical mask to block a large portion of the light that would otherwise bypass the tubes and directly strike the detector, thus reducing the possibility of overexposure. The walls 2812, 2814 also isolate the individual tubes openings 3500 to inhibit glare that might otherwise be present when the optical analysis is performed with one more tube strips missing from the tube strip holder 212.

As shown in FIG. 35, the tube strip holder 212 also may include additional openings 3502 located between the individual tube openings 3500 and around the outer perimeter. Such openings 3502 may be provided to reduce the weight of the tube strip holder 212, and preferably are not large enough to affect the optical testing results. Such openings 3502 also may serve other purposes. For example, one or more openings may comprise a registration opening 3504 (e.g., an asymmetric or unique shape or pattern of shapes) that indicates the orientation of the tube strip holder 212. This feature may be particularly helpful when the image is analyzed during later automated or manual processing steps to quickly and accurately determine the identity of each individual sample.

Figure 36:
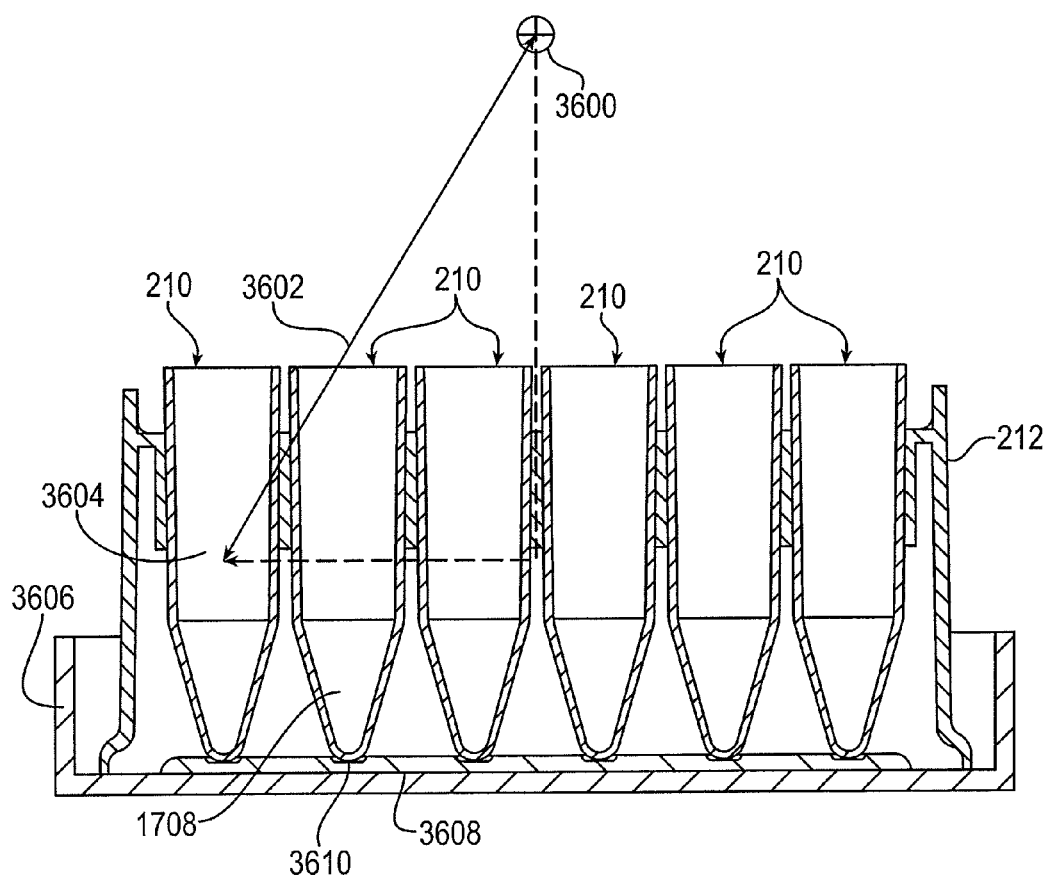
FIG. 36 illustrates exemplary centrifuge loads on an exemplary tube strip holder, tube strips and centrifuge bucket.

Referring now to FIG. 36, the tube strip holder 212 may also be configured for use in a centrifuge. Centrifuging can generate tremendous loads. For example, a 300 gram object centrifuged at 2,900 gravities generates a load of 870 kilograms. A tube strip holder weighing 130 grams would effectively weigh 377 kilograms, and a loaded tube strip weighing 25 grams would effectively weigh 72.5 kilograms. The effective mass can be reduced by minimizing the weights of the tube strip holder 212, tube strips 210 and samples, but the tube strip holder 212 and tube strip 210 must be strong enough to remain intact throughout centrifuging.

The forces generated by the centrifuge are oriented in a radial direction from the spin center 3600 to the center of mass of each centrifuged object, and masses that are further from the spin center 3600 will experience proportionately larger loads. In the case of a tube strip holder 212 loaded with tube strips, the tube strip holder 212 preferably is mounted with the center of the base perpendicular to the spin center, and the mass of the tube strip holder 212 and its contents positioned between the center of the base and the spin center, such as shown in FIG. 36. This arrangement prevents the creation of unbalanced centrifuge forces. However, this arrangement does lead to the generation of tangential forces (forces tangential to the rotation path) on the parts. For example, the centrifuge forces 3602 on the tubes and tube strips 3604 that are offset in the tangential direction from the center of the tube strip holder 212 will include a tangential component that will be exerted against the side of the tube strip holder 212. Similar tangential forces would be present at other locations, such as the lateral walls 2812 and longitudinal walls 2814. As will be understood from a simple vector analysis, the magnitude of these tangential forces increases as the spin radius decreases.

The tube strip holder 212 preferably is designed to withstand loads as high as 2,900 gravities for 15 minutes or more, in a centrifuge having a relatively small spin radius (e.g., less than about 200 mm). To this end, the tube strip holder 212 may comprise magnesium or other material having a relatively high strength-to-weight ratio. The tube strip holder 212 may be constructed to carry all of the forces generated by the tube strips 210 and samples therein, but in a more preferred embodiment, the tube strip holder 212 cooperates with the centrifuge bucket 3606 to distribute and collectively carry the centrifuge loads generated by the tube strips 210. For example, in the embodiment of FIG. 36, the centrifuge bucket 3606 includes a base 3608 in which a plurality of recesses 3610 are formed. Each recess 3610 receives the bottom of a respective tube 1708, such as shown in FIG. 36. The recesses 3610 are positioned to hold the tube strips 210 out of vertical supporting contact with the tube strip holder 212 (such as described above with reference to the heating block). In doing so, the centrifuge 3606 directly bears the tube strip's centrifuge loads in the vertical direction (i.e., the vertical direction of the tube strips 210 and tube strip holder 212). The bucket 3606 also may directly carry a portion of the tangential loads, such as those discussed above, by interaction between the recesses 3610 and the bottom tip of each tube 1708. The remaining tangential loads will be directly applied to the tube strip holder 212, and particularly to the lateral walls 2812. As such, the tube strip holder 212 preferably has sufficient strength to bear such loads. In the illustrated embodiment, the tube strip holder 212 is mounted in the centrifuge bucket 3606 with its long axis oriented in the tangential direction. As such, the lateral walls 2812 and end walls of the tube strip holder 212 should be strong enough to bear the tangential centrifuge loads. In this arrangement, using the centrifuge bucket 3606 to directly carry a large portion of the centrifuging loads allows the tube strip holder 212 to be lighter and potentially less complicated and expensive to manufacture.

In alternative embodiments, different load-bearing arrangements may be used. For example, the tube strips 210 may be mounted to swing within their respective tube strip wells 2808 to align with the direction of the centrifugal forces, which may alleviate the need for the tube strip holder 212 to bear tangential forces.

As will be appreciated from the foregoing description, the exemplary tube strip holder 212 may be constructed to provide a number of functional features and conveniences that are not found in conventional sample plates. The tube strip holder 212 holds a number of tubes in removable strips, and does so in a manner that allows automated removal and replacement of the tube strips 210 for processes such as decanting and blotting. To this end, the tube strips 210 may be provided as single rows of tubes 1708, which helps prevent cross-contamination during decanting, blotting, and other processes. The tube strip holder 212 also is configured to thermally couple to a heating block to distribute heat to the upper portions of the tubes 1708 during incubation, to help prevent condensation and ensure even heating of all of the tubes 1708. The tube strip holder 212 is also designed to form an optical mask to improve the vision inspection process, and to cooperate with the centrifuge bucket 3606 to contain the tubes 1708 during high-gravity centrifuging operations. In addition to all of these features, the tube strip holder 212 may be formed as a reusable part, to thereby save processing expenses.

The combination of the foregoing features in a single tube strip holder 212 is particularly beneficial to simplify the operation of automated processing modules, because it may minimize the need to transfer the samples from one holding device to another during processing. It will be appreciated, however, that it is not necessary in all embodiments to include or combine all of the foregoing features into a single tube strip holder 212, and the various features of the tube strip holder 212 may find separate utility in other applications.

Exemplary Vision Inspection Systems

Figure 37:
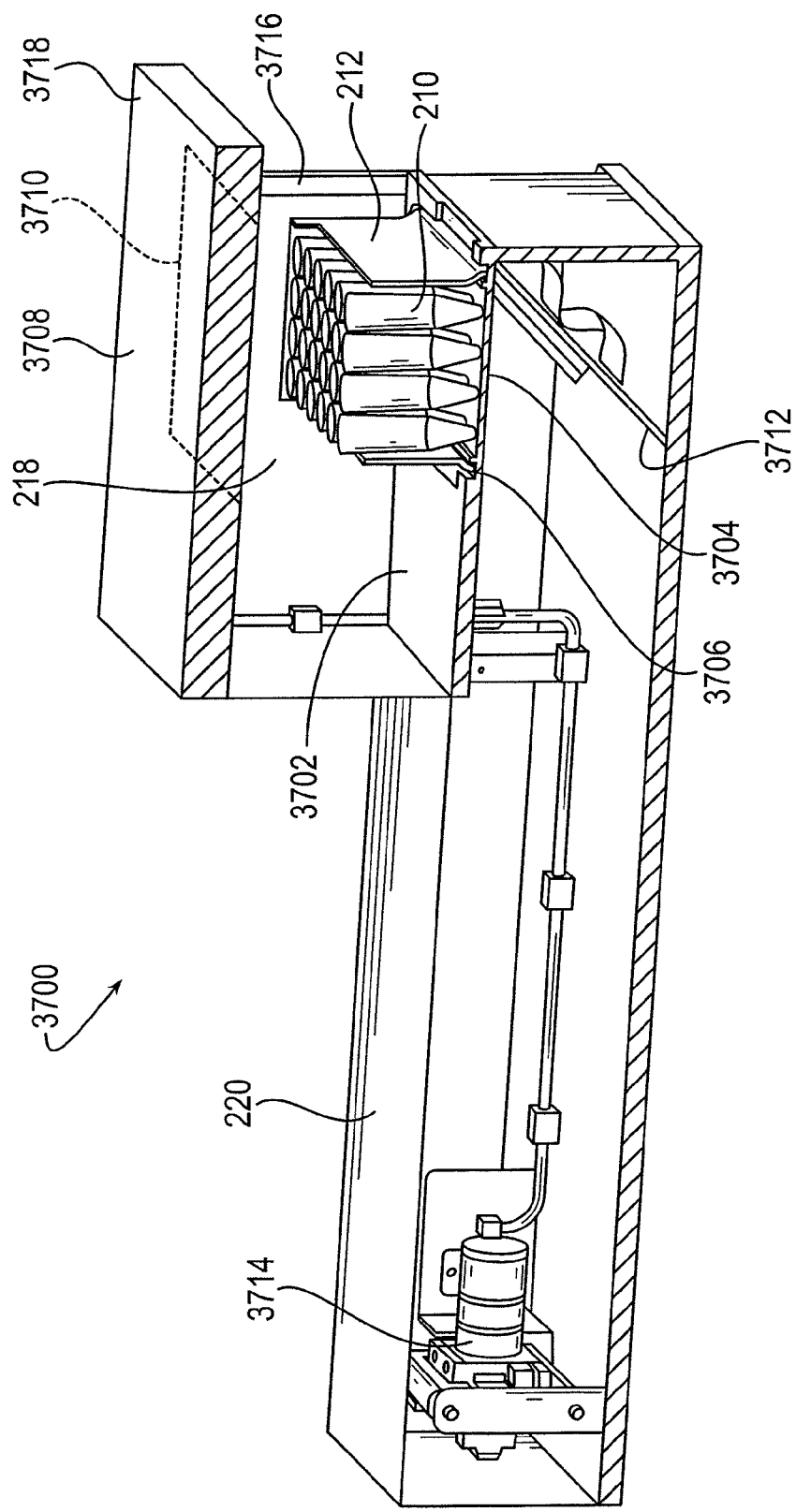
FIG. 37 is a cut away isometric view of an exemplary vision inspection system.
Figure 38:
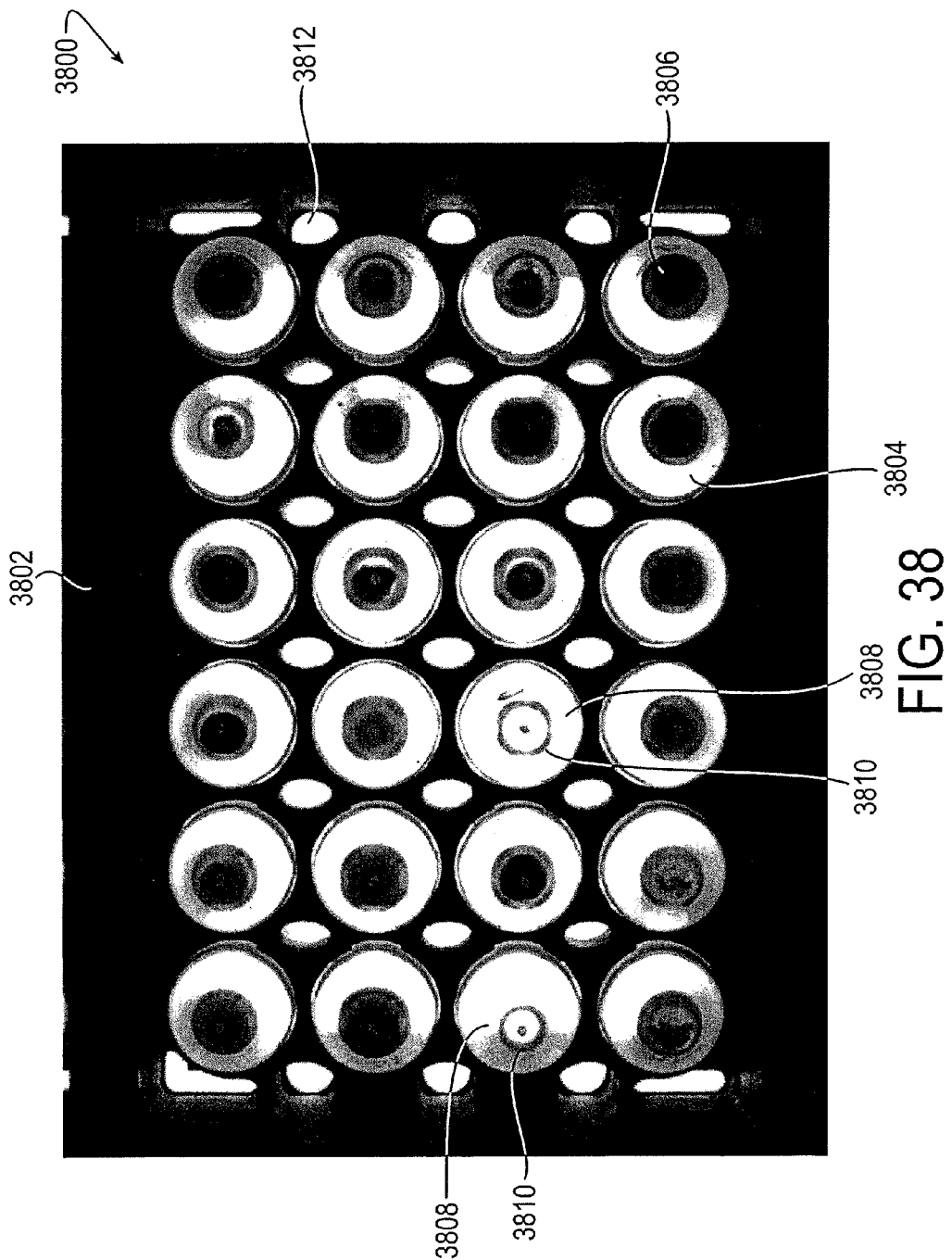
FIG. 38 is a perspective silhouette image of a tube strip holder, tube strips and samples, as viewed from the bottom.

Referring now to FIGS. 37 and 38, examples of exemplary vision inspection systems for detecting the presence of a pellet in a tube are described.

FIG. 37 shows a vision inspection system 3700 having a vision inspection station 218 and a camera enclosure 220. The vision inspection station 218 includes a platform 3702 configured to hold a tube strip holder 212 and its associated tube strips 210. The platform 3702 includes a transparent (e.g., glass, plastic or open) window 3704 through which the bottom of the tube trips 210 are visible. The window 3704 may be surrounded by a groove 3706 in which a lower lip of the tube strip holder 212 rests to ensure proper positioning. If it is determined that the inner lip of the groove 3706 blocks the view through the window 3704 to the tube strip holder 212, the tube strip holder 212 may be held within a retaining wall to allow a greater view of the parts. For example, the window 3704 may be surrounded by a beveled wall into which the tube strip holder 212 can be lowered to hold only the outer edge of the tube strip holder 212 and allow full viewing of the inner regions of the tube strip holder 212. This may be desirable when the tube strip holder includes features such as a registration opening 3504 near the outer perimeter.

The vision inspection station 218 is covered by an upper panel 3708 that contains one or more light-emitting diodes ("LEDs") or other light source 3710. The light source 3710 preferably is distributed over an area and includes a diffuser or other means to distribute the light source. In a preferred embodiment, the light source 3710 is a diffuse light that is distributed over an area larger than the area of tube strip holder 212, to minimize light falloff or dark areas around the edges of the tube strip holder 212. The light source 3710 may emit light having any monochromatic color or polychromatic color range, such as a warm white color.

A mirror 3712 is mounted below the window 3704 to reflect light from the light source 3710 that passes through the tube strips 210 and tube strip holder 212. The mirror preferably comprises a first surface mirror in which the front surface is the reflector, instead of the back surface. This prevents the creation, as typically happens in back surface mirrors, of a separate "ghost" image reflecting off the front surface. The mirror 3712 preferably is sized to reflect the entire image of the tube strip holder 212 and its tube strips 210 to allow simultaneous inspection of all of the tubes. A camera 3714 is located to view the light reflected by the mirror 3712. The camera 3714 may comprise any suitable visual inspection camera, such as a 5 megapixel color detector coupled to a 23 millimeter high-resolution lens. In the exemplary embodiment, the mirror 3712 is inclined at 45° angle to redirect the vertical light along a horizontal path. This provides a convenient configuration for the various parts, but other angles may be used in other embodiments. Also, if the camera 3714 is mounted with a direct view of the tube strips 210 (e.g., directly below the window 3704 and pointing up), the mirror 3712 may be omitted.

The parts of the vision inspection system 3700 are generally enclosed in a housing that blocks in the ingress of ambient light that might otherwise affect the test results. The tube strip holder 212 is placed in the vision inspection station 218 through an opening 3716, and the cover 3708 has an overhang 3718 that helps shade the interior of the housing. If desired, a closable door or other access port may be provided to more fully block ambient light.

The light source generates a silhouette image of the tube strips 210 and tube strip holder 212, such as the inspection image shown in FIG. 38. As explained above with reference to FIG. 35, the tube strip holder 212 may form a generally opaque light mask, which creates a large black or nearly black masked area 3802 in the inspection image 3800. The tubes 1708 of each tube strip 210 generate somewhat shaded circular tube images 3804. The sample pellets generate dark pellet images 3806. The inspection image 3800 also may include a number of bright through-hole images 3812, where light passes through through-holes formed in the tube strip holder 212.

The inspection image 3800 of this exemplary embodiment also exhibits two other notable features. First, it has been found that empty tubes 1708 generate empty tube images 3808 having a dark "sphere-cone" ring 3810 caused by light bending through the transition between the conical lower wall and hemispherical tip of the tube 1708. Other tube shapes may not exhibit this property.

In addition, the camera's location and lens type can result in a parallax effect. Parallax is an angular variation in the line of sight that depends on the distance to the viewed objects. Parallax causes equally-spaced objects to appear further apart when they are closer to the viewer, and closer together when they are further from the viewer (i.e., perspective). In the case of the tubes 1708 mounted in a tube strip holder 212 and viewed from the bottom, the bottom ends of the tubes 1708 (where the sample pellets are likely to be located) will appear on a slightly larger grid pattern than the openings through which the upper parts of the tubes pass. This makes the outer rows of tubes appear to spread outward. As shown in FIG. 38, this causes the pellet images 3806 to appear be displaced from the centers of their respective tube images 3804. The offset is greater for tubes that are further from the viewing axis of the camera 3714, which, in this case, is pointed directly at the geometric center of the tube strip holder 212. Such parallax can be mitigated by moving the camera further from the image, or using a telecentric lens.

The vision inspection system 3700 evaluates the inspection image 3800 to determine whether each tube includes a respective sample pellet. This analysis may be performed on samples with or without the presence of a supernatant liquid (e.g., before or after decanting). In the context of a HC2 process, the samples may comprise a transport stabilization medium liquid containing a small percentage of cellular, blood, mucous and/or other materials obtained with a cervical sample. The sample is centrifuged to compress the denser, and in this case more opaque, material into a pellet form. In other contexts and embodiments, the tube may contain other kinds of samples.

In some cases, a sample tube may not appear to include a sample pellet, either because the sample simply was not taken, or because the sample was not adequate to form a pellet. In these cases, the contents of the tube may still be processed to determine whether they include HPV or other condition. If the results come back positive (i.e., HPV or another condition is detected in the sample), then the test results may be sufficient despite the lack of a visible pellet. However, if the results of the assay are negative (i.e., no HPV or other condition is detected), then the test will be ruled indeterminate because it cannot be determined whether it was due to a lack of the condition, or the insufficiency of the sample. In these cases, a supplemental test may be performed or another effort may be made to obtain an adequate sample from the patient.

Any suitable algorithm may be used to determine the presence of a sample pellet in each tube. In one example, described in detail below, the image processing algorithm performs two main steps. First, it analyzes the inspection image 3800 to locate the tubes within the image and create respective regions of interest. Second, the algorithm separately analyzes each region of interest to determine whether it contains a pellet image. In the following example, there are 24 tubes and 24 associated regions of interest, but other quantities may be used instead.

Figure 39:
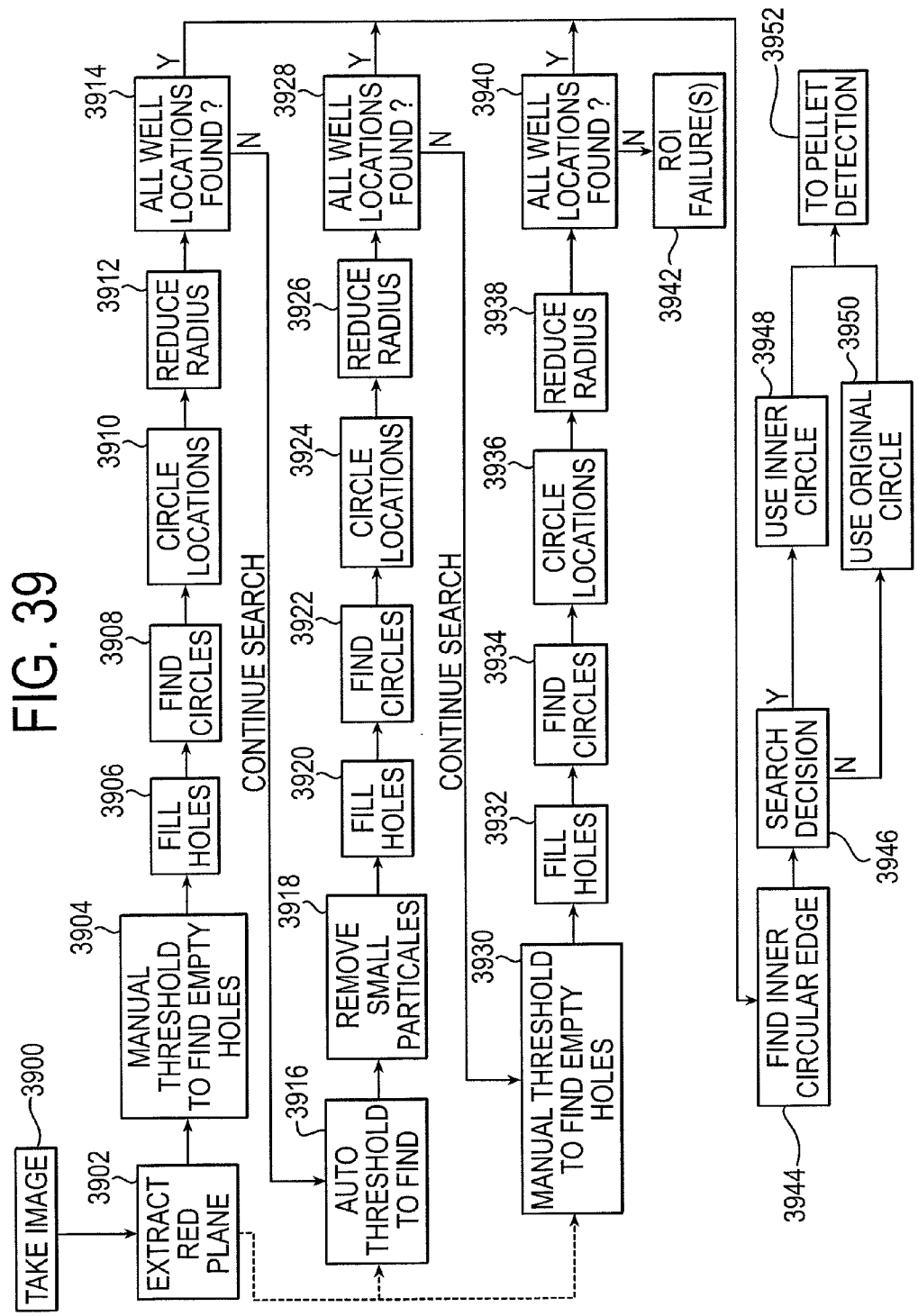
FIG. 39 is a flowchart of an exemplary process for identifying regions of interest in an image such as shown in FIG. 38.

The first step of the exemplary process—identifying regions of interest (hereinafter, the "ROI process")—is detailed in FIG. 39. In general terms, the purpose of the ROI process is to identify and isolate the twenty-four tube locations in the image, and remove the data representing the dark masked area 3802 and the bright through-hole images 3812.

The ROI process begins at step 3900 when the camera 3714 takes the inspection image 3800 of the tube strip frame, tubes and samples. The signal gain (light "amplification") of the camera 3714 may be set at a predetermined level based on an initialization process, or actively controlled based on other criteria or feedback, in order to provide contrast levels that are expected to facilitate the remaining processing steps. If the camera 3714 uses a color sensor (i.e., one that detects separate red, green and blue channels or equivalents thereof), the signal may be processed to extract the red image data as intensity values and discard the remaining data (green and blue) for some or all of the remaining process steps. By separating out only one color channel, the image data becomes a monochromatic image with intensity being measured on a conventional 0-255 scale, with 0 being no intensity (black), and 255 being the maximum intensity (pure red). Intermediate values represent different intensities of the light (different darker shades of red). The red channel is selected in this example because it provides the greatest contrast range for the particular subject matter of the HC2 protocol being performed. The HC2 protocol uses a Sample Conversion Buffer that makes the liquid clear red, and the pellet a brownish-red, and thus the variations in the contrast are most visible in the red color range (blue and green channels would make the contents darker and more confusing to distinguish details). Other processes may use other color channels, composite colors, greyscale data, or the like.

Once the red channel is extracted, the ROI process may use one or more search techniques to search for regions of interest. In this example, three techniques are performed sequentially or in parallel.

The first search technique begins at step 3904. In this step, the ROI process filters the image data to find all data points having an intensity of 253 to 255 on the 0-255 scale. This step identifies "holes" where the light passes through the tubes and through-holes without losing much intensity. It will be appreciated that the data points that form the image each may represent the image data detected by a single point detector (sometimes called a "pixel") on the camera's image sensor. However other groupings may be used to identify discrete data points (e.g., each point may be the average value detected by multiple adjacent point detectors), and filtering algorithms such as conventional sharpening masks may be applied before or during the ROI process.

In step 3906, the ROI process "fills" the holes found in step 3904 to generate solid regions. In step 3908, the ROI process searches the solid regions to find circular areas having a radius between 145 and 200 pixels. These circular areas are identified as regions of interest, and areas smaller than this are removed from further consideration. The 145-200 pixel range is selected in this embodiment because it is larger than the sizes of the through-hole images 3812, but smaller than the tube images 3804. Thus, in effect, step 3908 removes the through-holes images 3812 from further consideration. In other embodiments having different pixel scales, other dimensions may be used.

In step 3910, the ROI process matches the regions of interest to a default grid of twenty-four predetermined locations. For example, the ROI process may find the center of each circular region of interest, and compares these centers to points or areas on the grid. This prevents badly misaligned tube strip holders from being processed incorrectly. Minor deviations may be processed as normal, and larger deviations may generate an error signal indicating the need to realign the tube strip holder. It also may be possible to correct deviations by orienting and/or scaling the image to position the regions of interest to match the default grid.

Next, in step 3912, the ROI process crops the radius of each region of interest by 25 pixels to remove any dark shadows caused by the masked area 2809 that might appear in the regions of interest. This is most important in the outer rows of tubes (those furthest from the viewing axis) because the walls of the tube frame holder 212 appear to overlap portions of the tubes due to the parallax view, and cast shadows over the outer edges of the tubes. Again, the 25 pixel value is based on the pixel scale of the particular embodiment, and other values may be used in other embodiments.

In the final step 3914 of the first search technique, the ROI process determines whether a region of interest has been identified for each tube well. If all twenty-four tube wells are imaged, then the process continues to step 3944, which is described below. If the tube well locations are not all found, then processing continues to the second search technique, which begins at step 3916.

Step 3916 begins with the monochromatic image generated in step 3902, and uses an automatic threshold evaluation routine to find regions of interest for any of the remaining tube wells. This process may be performed on the entire image, or just in particular areas corresponding to tube well locations where no region of interest was found using the first search technique. The automatic threshold evaluation routine 3916 uses an entropy method or other automatic method to identify and extract more intense regions from an image containing a mixture of more and less intense (i.e., lighter and darker) regions. The starting parameters (if any) and exact entropy model may be selected according to well-known image processing techniques, and such methods and the details of such algorithms need not be described here.

After step 3916 extracts the more intense regions, the second search technique applies a filter in step 3918 to remove extracted intense regions having an area of less than 2000 pixels. This filter removes image "static" and any small specular reflections or through-hole images 3812 from further consideration.

The remaining areas identified in step 3916 are then "filled" in step 3920 to generate solid regions, and filtered in step 3922 to identify circular regions of interest comprising circular areas having a radius between 160 and 200 pixels, and remove any other areas from further consideration. In step 3924, the centers of the circular regions of interest are matched to the default grid, as described above in step 3910. Next, in step 3926, the regions of interest are cropped by 25 pixels, as described above in step 3912.

At the end of the second search technique, the ROI process determines whether a region of interest has now been identified for each of the expected tube well locations. If so, the process continues at step 3944, described below. If not, the ROI process continues to a third search technique starting at step 3930.

The third search technique comprises a series of steps, starting at step 3930 and concluding at step 3940, that generally match steps 3904 through 3914 described above. The only difference is that the third search begins in step 3930 by filtering the image data to find all data points having an intensity of 85 to 255 on the 0-255 scale. Thus, the third search technique uses a lower intensity cutoff threshold to identify regions of interest. This technique is expected to identify tube images 3804 that are darker and have less contrast than those identified by the first two techniques. At the end of the third search technique, the ROI process once again determines whether a region of interest has been identified for each expected tube well location. If so, the process continues to step 3944. If not, the ROI process continues to step 3942, where it generates an error signal indicating that the ROI process was unable to identify a region of interest for each tube well location. In this case, the entire vision inspection process may cease for the particular tube strip holder, or it may continue for any tube well locations that are successfully identified by a region of interest.

Figure 40:
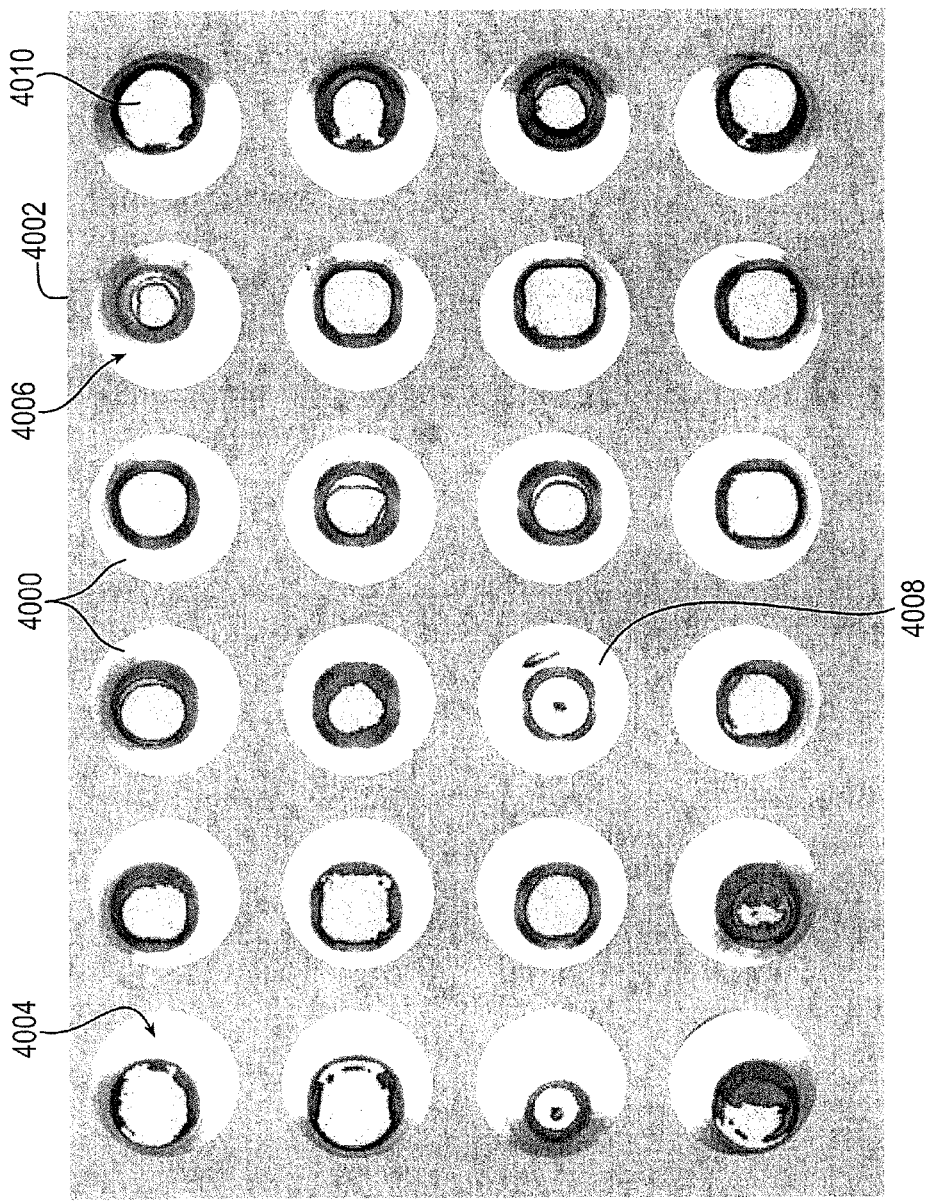
FIG. 40 is a representative image of the regions of interest and other information extracted from the image shown in FIG. 38, using the process of FIG. 39.

FIG. 40 is an exemplary output image generated by performing the image processing algorithm on the inspection image 3800 of FIG. 38. The twenty-four circles indicate the regions of interest 4000. Area 4002 indicates the portion of the original inspection image 3800 that has been excluded from further analysis. Additional details of the image are discussed below.

Once all (or as many as possible) of the regions of interest have been identified, the ROI process may terminate and the pellet detection process may begin. However, as noted above, it has been found that certain tubes having a conical section that transitions to a hemispherical tip may generate a sphere-cone ring 3810. In some cases, the sphere-cone ring 3810 may blend continuously with or be smaller than the pellet image 3806 (see, e.g., tube image 4004 in FIG. 40), in which case the sphere-cone ring 3810 will not be mistakenly identified as a pellet image 3806. In other cases, the pellet image 3806 may be smaller than the sphere-cone ring 3810 (see, e.g., tube image 4006 in FIG. 40). In still other cases (see, e.g., tube image 4008 in FIG. 40), the tube image may include only the sphere-cone ring 3810. The existence of the sphere-cone ring 3810 may make it necessary to further narrow the region of interest to prevent the sphere-cone ring 3810 from being erroneously identified as a pellet image. Any suitable method may be used to find the sphere-cone ring 3810, and to determine whether the pellet is inside the sphere-cone ring 3810.

An exemplary process for accounting for the sphere-cone ring 3810 is to determine whether the inner boundary of the sphere-cone ring 3810 are visible, and, if so, reduce the region of interest to cover only portion of the tube image 3804 that is inside the sphere-cone ring 3810. In doing so, the process excludes the sphere-cone ring 3810 from being considered a pellet. This exemplary process begins at step 3944, in which the ROI process searches each region of interest (as identified in the previous steps) for the presence of an inner ring. The presence of parallax in the image will cause the sphere-cone rings 3810 to appear at different locations with respect to the center of each tube image 3804, as shown in FIGS. 38 and 40. More specifically, the sphere-cone rings 3810 of the tube images 3804 that are farther from the viewing axis of the camera 3714 will be more offset relative from the center of the tube image 3804. If parallax is not accounted for, the process may mistake a portion of the sphere-cone ring 3810 for a pellet. As such, the ROI process accounts for this by searching at the appropriate expected location of each sphere-cone ring 3810 based on the location of the tube in the array. The expected size and location of the sphere-cone rings 3810 for each tube in the twenty-four tube array can be readily determined by testing or other means, and the location within each tube should remain approximately the same in each test unless there is a severe misplacement or manufacturing variance.

Figure 41:
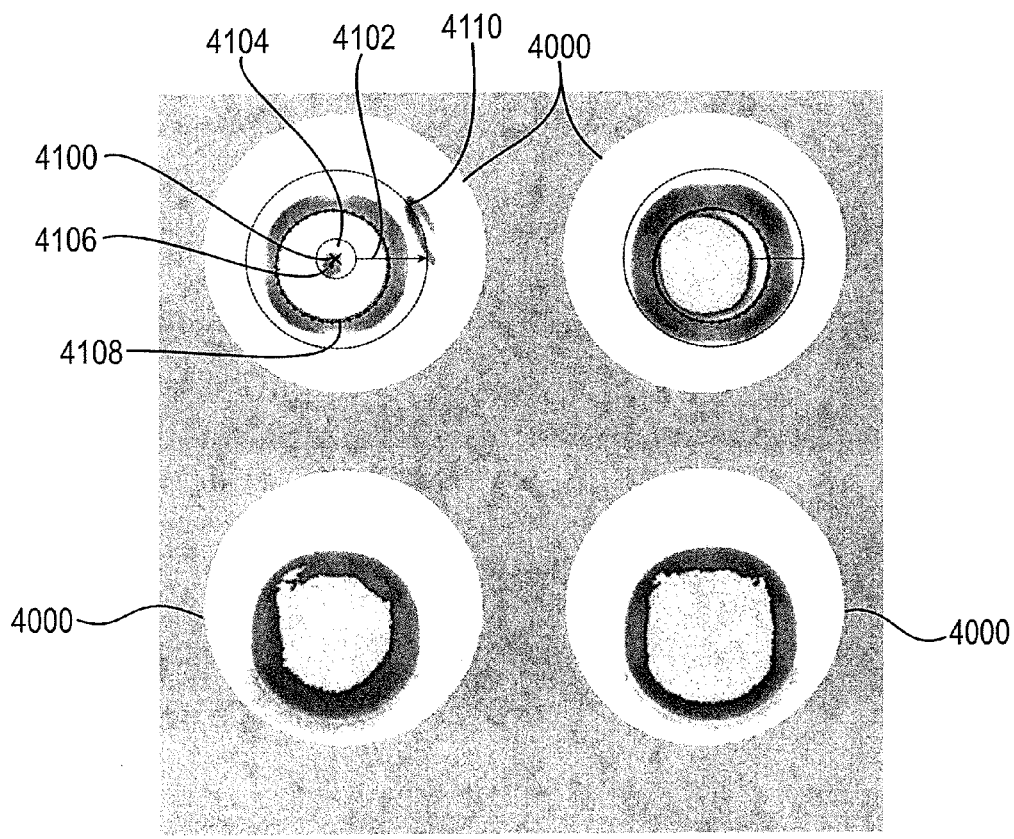
FIG. 41 is an enlarged view of the four tubes located at the center of the bottom two rows of tubes shown in FIG. 40.

Referring now to FIG. 41, the ring detection process uses a radial test pattern centered at the expected center 4100 of the tube. The expected center 4100 is the center is based on the known parallax relationship of the tube with respect to the viewing axis, and is offset from the geometric center of the circular region of interest 4000 unless the tube is on or nearly on the viewing axis. The radial test pattern analyzes a series of radial traces 4102 that start a short distance 4104 from the expected center 4100 and move in the outward radial direction. The traces start at a distance 4104 from the expected center 4100 because, in this embodiment, the tube images 3804 are known to include a small dark spot 4106 caused by the gate recess of the tube (the point where the material passes into the injection mold during the forming process). Thus, the trace excludes the region where the gate recess spot 4106 might appear. In other embodiments that lack a recess spot 4106, this offset may be eliminated. Any number of traces 4102 may be used. In this case, the radial test pattern uses thirty-six traces 4102 that are spaced at 10° angles around the expected center 4100. Also in this embodiment, each trace starts 20 pixels from the expected center 4100 (the inner dashed line in FIG. 41), and ends 90 pixels from the expected center 4100 (the outer dashed line in FIG. 41). These pixel dimensions may, of course, be modified in other embodiments, to account for other pixel densities and geometries.

Each trace 4102 is analyzed in the outward direction using a conventional falling edge analysis to detect a transition from a high-intensity region to a low-intensity region. If the entire region inside the sphere-cone ring 3810 is filled with a pellet image 3806, then there will be no falling edges (transitions from light to dark). If there is a pellet image 3806 located entirely inside the sphere-cone ring 3810, or no pellet image 3806 at all, then the process will detect a falling edge at the inner edge of the sphere-cone ring 3810. The first time the ring detection process detects an falling edge, it records the location as an edge point 4108. By using only the first falling edge, the trace ignores additional falling edges that might occur as the trace crosses objects outside the sphere-cone ring 3810, such as the image of a water drop 4110 shown in FIG. 41. After analyzing all of the traces, the ring detection process fits a circle inside the identified edge points to delineate the expected location of the inner ring of the sphere-cone ring 3810.

In step 3946, the ROI process evaluates the size of the detected circle to confirm that it is within the expected size of a sphere-cone ring 3810. In this example, if the detected circle has a radius of 40 pixels to 65 pixels, then it is considered to be a valid detection of a sphere-cone ring 3810. In this case, the ROI process proceeds to step 3948, in which the region of interest 4000 for the tube image in question is cropped to the size of the circle identified by the ring detection process. In the example shown in FIG. 41, the two top tube images 4000 were determined to have a qualifying sphere-cone ring 3810, and their regions of interest were cropped to the size of the circle generated during the ring detection process.

If no ring is detected, or if a detected ring is larger or smaller than the expected valid sphere-cone ring 3810 size, the ROI process moves to step 3950 and uses the original region of interest for the tube image in question. In the example of FIG. 41, the two bottom tube images 4000 were determined to not have a qualifying sphere-cone ring 3810, and their regions of interest were not cropped.

Finally, after the ROI process determines whether to use the original region of interest in step 3950, or the reduced region of interest in step 3948, the process continues in step 3952 to the pellet detection process. The pellet detection process may use any suitable algorithm to evaluate the tube image 3804 or region of interest to determine whether it includes a pellet image 3806 that corresponds to a sample pellet.

An example of a pellet detection process is illustrated in the flowchart of FIG. 42. The process begins in step 4200 by receiving the region of interest information from the ROI process. This information is used to "mask" the original image data to narrow the areas in which the pellets are sought during the pellet detection process.

Before checking for the presence of pellets, the pellet detection process scans the image to determine whether any tubes are missing altogether. To do so, the process the process extracts the intensity data from the original image, in step 4202, and then evaluates and reports the average intensity for each region of interest in step 4204. This process may use a simple average of the intensity value of each point in each region, or other algorithms. Next, in step 4206, the process evaluates whether the intensity of the image in any region is greater than would be expected if a tube was present. In this embodiment, step 4206 determines whether any region has more than 95% of its pixels at an intensity of 254 or greater on the 0-255 intensity scale. Any qualifying region is labeled as lacking a tube. Since the tubes in the shown embodiment are provided on tube strips 210, that should mean that the other three tubes on the strip are missing, and those regions also should be identified, using the algorithm of step 4206, as lacking a tube. If this is not the case, then a separate error may be generated to indicate that the tube strip 210 is defective (e.g., missing one tube), or that the system is not functioning properly.

After identifying any missing tubes, the process moves to step 4208 and optionally extracts the red plane data from the original inspection image 3800. This may be done to change the contrast properties of the image as described above. Alternatively, the pellet detection process may use the full-color image, a greyscale image formed as a composite of one or more color channels (e.g., red, green and/or blue), or other permutations of the original image data. As noted above, sharpening and other algorithms such as noise reduction and the like, may be performed on the image data before or during the pellet detection process.

Next, in step 4210, the process performs a threshold algorithm, such as the conventional Niblack local thresholding algorithm, to identify darker areas—referred to herein as "particles"—within the regions of interest. In step 4212, thin connections between particles are excluded to separate the particles from one another, and in step 4214 an automatic median process is used to smooth and simplify the contours of the particles, and close small gaps and holes.

Figure 43:
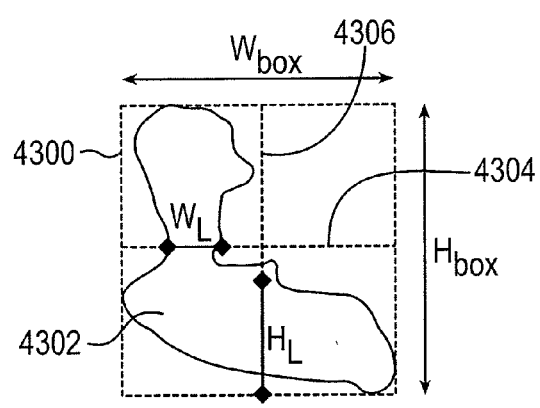
FIG. 43 is a graphic illustration of steps in an exemplary process for analyzing the dimensional properties of a particle to determine whether it represents a sample pellet.

Starting in step 4216, various geometric criteria may be applied to determine whether a particle is a pellet image 3806. In step 4216, a bounding box 4300 is generate around each particle, such as shown in FIG. 43. The bounding box 4300 has a width $W_{box}$, and a height $H_{box}$ that are just large enough to enclose the particle 4302. In step 4218, the process plots the intensity of a horizontal line 4304 and a vertical line 4306 passing through the center of the bounding box 4300. The intensity of each plot will have one value where the particle 4302 is absent, and another value where the particle 4302 is present, as shown by segments $W_L$ and $H_L$. In step 4220, the process determines the ratio of the intensity portion ($W_L$, $H_L$) of each line to the overall length of each trace (equal to $W_{box}$, $H_{box}$). If the value of $W_L/W_{box}$ or $H_L/H_{box}$ is less than 50%, then the particle is determined not to be a pellet and excluded from further consideration. This step eliminates hollow particles, crescent-shaped particles, and other particles that would not have an expected pellet shape. It will be appreciated that this step, and others described herein that rely on intensity variations to delineate objects, can be performed by rendering the particle as a high-intensity region and the background as a low-intensity region (or simply deleting the background intensity value), or in the opposite manner by rendering the particles as a low-intensity region and the background as a high-intensity region—in short, the processes and analyses described can be performed on a "negative" image or "positive" image. Thus, if the particle is rendered as a high-intensity region and the rest of the space as a low-intensity region, then step 4220 will operate by dividing the length of the high intensity portion of the trace by the overall width, and rejecting the particle if the value is less than 0.5.

Next, in step 4222, the process performs a size threshold rejection by excluding particles having an area of less than 700 pixels. Of course, in embodiments having other pixel densities and dimensional properties, different area values may be used. This step excludes the dark spot 4106 caused by the gate recess, small scuffs, and other particles that are too small to be a likely pellet.

In step 4224, the process analyzes the ellipse ratio of each remaining particle by dividing the length of its longest axis to the length of the axis perpendicular to the longest axis. If the ratio of the ellipse major axis length to the ellipse minor axis length is greater than 9:1, then the particle is rejected from further consideration. This step eliminates particles that are not generally round like a pellet should be. This step has been found to be helpful to eliminate particles generated by drops of transport media hanging on the tube walls after decanting in the HC2 protocol. The water drop 4110 in FIG. 41 would likely be excluded in this step, if it was not excluded in step 4220 or 4226 as being a hollow particle or having a large hole.

Next, in step 4226, the process eliminates particles with significant holes in them. To do so, step 4226 evaluates the bounding box image as shown in FIG. 43 and calculates the ratio of the high-intensity (particle) region to the total area (the particle region plus the hole region), and rejects the particle from further consideration if this value is less than 0.80. This step eliminates thin-walled hollow particles.

If any of the regions of interest still includes a particle after the elimination processes described above, that particle is deemed to qualify as a genuine pellet. In step 4228, the process labels any region of interest that passes the above criteria as having a pellet, and any region of interest that does not pass any one of the above criteria as having no pellet. FIG. 40 graphically illustrates the particles that have passed the pellet criteria, and are deemed to be pellets 4010, in cross-hatched lines. The remaining part of each tube image 4000 is not considered to be part of the pellet, however the particles that do not pass all of the criteria may also be represented in the image, and identified by a different color or shading pattern. In this example, all but two of the tubes have been found to include a pellet.

Finally, in step 4230, the process generates a data record indicating the status of each tube well location (and thus each corresponding sample) as lacking a tube (step 4206), having a pellet (step 4228), lacking a pellet (step 4228), or failing due to not identifying a region of interest (step 3942).

The foregoing image processing system may be used in embodiments of a processing module, or as a separate stand-along processing device. However, it will be appreciated that alternative image processing equipment and methods may be used in other processing modules. Other variations and modifications will be apparent to persons of ordinary skill in the art in view of the present disclosure.

First Processing Example

An embodiment of a sample processing module assembled according to the embodiment of FIG. 2 was used to process human tissue samples according to the process described with reference to FIG. 3. Specifically, samples in vials of Preserv-Cyt® media were manually mixed and dispensed into separate tubes of a four-tube tube strip. Each tube in the strip was a 6 milliliter tubes with conventional Sarstedt cone geometry. The tube strips were manually loaded into the processing module. At this point, automated processing began. First, the processing module loaded each tube strip into a tube strip holder that holds six tube strips. A Hamilton pipettor loaded with 5 milliliter tips dispensed 400 micro-liters of HC2 Sample Conversion Buffer into each tube. Next, the tube strip holder (including the tube strips and samples) was mixed on a Hamilton orbital shaker operated for 30 seconds at 800 rpm on a 3 millimeter orbit. The tube strip holder (and strips and samples) was then loaded into a BioNex centrifuge using a Hamilton iSwap transporter, and centrifuged at 2,900 gravities for 15 minutes. After centrifuging, a vision system was used to confirm that a pellet was in each tube. The tube strip holder was then conveyed to a decanting station, where each tube strip was removed, decanted and placed back in the tube strip holder. The tube strips were decanted by rotating them in a first direction to a 150° angle (measured downwards from vertical), holding them in this position for one second, then slowly rotating them back (opposite to the first direction) to the upright starting position. Next, the tube strip holder was again placed in the vision system to confirm that a pellet remained in each tube after decanting. The tube strip holder was then placed on a platform and a Hamilton pipettor was used to dispense 100 microliters of standard HC2 Specimen Transport Medium, and then 50 microliters of standard HC2 Denaturation Reagent, into each tube. Next, a cover was placed on the tube strip holder, and the tube strip holder was placed in a Hamilton shaker and mixed for two minutes at 1,250 rpm on a 3 millimeter orbit at room temperature. The tube strip holder was next placed on a Hamilton heater/shaker and heated to 65° (±2°) Celsius. Fifteen minutes into heating, the heater/shaker was operated for 30 seconds at 1,250 rpm on a 3 millimeter orbit, while heating continued. After shaking, the tube strip holder remained on the heater/shaker and continued to incubate at 65° (±2°) for another 30 minutes. At the end of the second heat cycle, the heater/shaker was operated at 1,250 rpm on a 3 millimeter orbit for 10 seconds, while continuing to apply heat. The total incubation time, including incubation during the mixing cycles, was 45 minutes and 40 seconds. Next, the tube strip holder was moved to a platform, and a Hamilton pipettor was used to transfer a 75 microliter specimen from each sample tube to a respective well on a hybridization plate. Calibrators or controls may be processed and dispensed on the hybridization plate along with the samples, or processed added to the hybridization plate manually.

Second Processing Example

The process and apparatus described in the First Processing Example were modified by making the following changes. First, the samples were originally provided in Sure-Path™ media, rather than PreservCyt®. Second, SCB was not dispensed into the tube strip. Third, the pre-centrifuge mixing step (step 310) was not performed. Fourth, the centrifuge step (step 312) was conducted at a somewhat lower gravitational load, and for approximately ten minutes. Fifth, the samples were decanted by rotating the tube strip in a first direction to an angle of 210° (measured downwards from vertical), pausing for approximately 0.5 to 1 second, and then continuing to rotate the tube strip in the first direction until the tube strip was upright (i.e., a full 360° rotation with a 0.5 to 1 second pause at 210°). And sixth, the incubation step (step 326) was conducted for approximately 90 minutes, with some variation in the mixing process. The remaining steps and procedures were identical to those described in the First Processing Example.

Third Processing Example

An embodiment of a sample processing module assembled according to the embodiment of FIG. 4 was used to process human tissue samples according to the process described with reference to FIGS. 5 and 3. In this example, individual samples in PreservCyt® vials were vortexed according to the conventional manual HC2 procedure, and then manually loaded into vial racks. The loaded vial racks were loaded into the processing module, and automated processing began. The automated process began by operating Hamilton pipettors loaded with 5 milliliter pipette tips to hydraulically mix the contents of each sample vial, and pipette 4 milliliters of each mixed sample solution to a respective tube in a four-tube tube strip, such as the tube strip described in the First Processing Example. From here, the processing module continued processing the samples as described above in the automated processing steps of the First Processing Example.

Fourth Processing Example

The process and apparatus described in the Third Processing Example were modified by starting with samples in Sure-Path™ media and vials, rather than PreservCyt® media and vials. Additional changes to the process are described above in the Second Processing Example. The remaining steps and procedures were identical to those described in the Third Processing Example.

Unless otherwise indicated herein, the volumes and other measurements identified and claimed herein are intended to cover the stated measurement and deviations from the stated measurement that would not be expected by persons of ordinary skill in the art to materially alter the performance of the processes described herein, or that are generally accepted by the relevant persons to be an acceptable error range for the measurement in question. Such deviations would be considered approximations of the stated measurement (e.g., such expected or accepted deviations for a value of "400 microliters" would be considered approximately 400 microliters). Furthermore, where one value in a range is specifically identified as being an approximate value, it will be understood that the other value in the range also is an approximate value unless indicated otherwise.

The present disclosure describes a number of new, useful and nonobvious features and/or combinations of features that may be used alone or together. For example, the exemplary processing modules and processing methods may be used independently of the sample adequacy system, tube strips, decanting systems, blotters, and heating systems described herein, and vice versa. The multiple separate inventions stand alone and are not intended to require combination with other inventions. Furthermore, the embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

The invention claimed is:

1. An automated sample tube blotting system comprising:
a processing module;
a pair of rotary grippers, each rotary gripper having a respective tube strip holder, the pair of rotary grippers being rotatable between a first position in which the respective tube strip holder is upright and a second position in which the respective tube strip holder is inverted;
a tube strip comprising one or more connected sample tubes, the tube strip being configured to be held by the respective tube strip holder of each of the pair of rotary grippers; wherein the pair of rotary grippers are located at respective opposite ends of the tube strip when the tube strip is held by the pair of rotary grippers;
a supply of absorbent material connected to the processing module;
a transport mechanism movably connecting the pair of rotary grippers to the processing module and configured to move the pair of rotary grippers in a lateral direction from a starting location to a location above the absorbent material, and in a vertical direction towards and away from the absorbent material; and
an absorbent material removal mechanism connected to the processing module.

2. The automated sample tube blotting system of claim 1, wherein the supply of absorbent material comprises a supply of absorbent sheets.

3. The automated sample tube blotting system of claim 2, wherein the supply of absorbent sheets comprises a stack of overlaid absorbent sheets.

4. The automated sample tube blotting system of claim 1, further comprising a waste well adjacent the supply of absorbent material, and a drip tray extending between the waste well and the supply of absorbent material.

5. The automated sample tube blotting system of claim 4, wherein the starting location of the pair of rotary grippers is above the waste well, and the transport mechanism is configured to move the pair of rotary grippers in a lateral direction directly above the drip tray from the starting location to the location above the absorbent material.

6. An automated sample tube blotting system comprising:
a processing module;
one or more rotary grippers, each rotary gripper having a respective tube strip holder, the one or more rotary grippers being rotatable between a first position in which the respective tube strip holder is upright and a second position in which the respective tube strip holder is inverted;
a supply of absorbent material connected to the processing module;
a transport mechanism movably connecting the one or more rotary grippers to the processing module and configured to move the one or more rotary grippers in a lateral direction from a starting location to a location above the absorbent material, and in a vertical direction towards and away from the absorbent material; and
an absorbent material removal mechanism connected to the processing module;
wherein the transport mechanism comprises one or more pipette channels selectively connected to a respective one of the one or more rotary grippers.

7. An automated sample tube blotting system comprising:
a processing module;
one or more rotary grippers, each rotary gripper having a respective tube strip holder, the one or more rotary grippers being rotatable between a first position in which the respective tube strip holder is upright and a second position in which the respective tube strip holder is inverted;
a supply of absorbent material connected to the processing module;
a transport mechanism movably connecting the one or more rotary grippers to the processing module and configured to move the one or more rotary grippers in a lateral direction from a starting location to a location above the absorbent material, and in a vertical direction towards and away from the absorbent material; and
an absorbent material removal mechanism connected to the processing module;
wherein the absorbent material removal mechanism comprises a movable arm having counter-rotating grippers.

8. An automated sample tube blotting system comprising:
a processing module;
one or more rotary grippers, each rotary gripper having a respective tube strip holder, the one or more rotary grippers being rotatable between a first position in which the respective tube strip holder is upright and a second position in which the respective tube strip holder is inverted;
a supply of absorbent material connected to the processing module;
a transport mechanism movably connecting the one or more rotary grippers to the processing module and configured to move the one or more rotary grippers in a lateral direction from a starting location to a location above the absorbent material, and in a vertical direction towards and away from the absorbent material;
an absorbent material removal mechanism connected to the processing module; and
a paper supply container connected to the processing module and the holding the supply of absorbent material, the paper supply container comprising a box having an open top, a lip surrounding a portion of the open top, and a gap in the lip, the gap being adjacent the absorbent material removal mechanism to facilitate removal of individual sheets of absorbent material from the box.

* * * * *